United States Patent
Hilpert et al.

(10) Patent No.: US 9,115,098 B2
(45) Date of Patent: *Aug. 25, 2015

(54) 1,3-OXAZINES AS BACE1 AND/OR BACE2 INHIBITORS

(71) Applicant: Hoffmann-La Roche Inc., Nutley, NJ (US)

(72) Inventors: Hans Hilpert, Muenchenstein (CH); Wolfgang Wostl, Grenzach-Wyhlen (DE)

(73) Assignee: HOFFMAN-LA ROCHE INC., Nutley, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 14/268,085

(22) Filed: May 2, 2014

(65) Prior Publication Data

US 2014/0243325 A1 Aug. 28, 2014

Related U.S. Application Data

(63) Continuation of application No. 13/439,893, filed on Apr. 5, 2012, now Pat. No. 8,754,075.

(30) Foreign Application Priority Data

Apr. 11, 2011 (EP) .................................... 11161803

(51) Int. Cl.
*C07D 265/08* (2006.01)
*C07D 413/12* (2006.01)
*C07D 417/12* (2006.01)
*C07D 265/10* (2006.01)

(52) U.S. Cl.
CPC ............ *C07D 265/10* (2013.01); *C07D 265/08* (2013.01); *C07D 413/12* (2013.01); *C07D 417/12* (2013.01)

(58) Field of Classification Search
CPC .. C07D 265/08; C07D 265/10; C07D 413/12; C07D 417/12

USPC .................................... 544/88, 96; 514/228.8
See application file for complete search history.

(56) References Cited

U.S. PATENT DOCUMENTS 7,964,594 B1 * 6/2011 Banner et al. .............. 514/228.8
8,754,075 B2 * 6/2014 Hilpert et al. .............. 514/228.8

FOREIGN PATENT DOCUMENTS

EP 2511268 10/2012
WO 2011/069934 6/2011

OTHER PUBLICATIONS

The English translation of the Japanese Office Action, issued on Oct. 7, 2014, in related Japanese Application No. 2014-504274.
The English translation of Chinese Office Action, issued on Oct. 11, 2014, in Chinese Application No. 201280017754.7.

* cited by examiner

*Primary Examiner* — Kahsay Habte

(57) ABSTRACT

The present invention provides 4-(3-Amino-phenyl)-5,6-dihydro-4H-[1,3]oxazin-2-ylamines of formula I

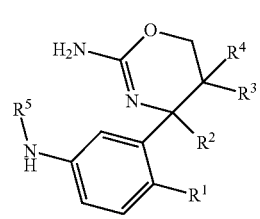

having BACE1 and/or BACE2 inhibitory activity, their manufacture, pharmaceutical compositions containing them and their use as therapeutically active substances. The active compounds of the present invention are useful in the therapeutic and/or prophylactic treatment of e.g. Alzheimer's disease and type 2 diabetes.

26 Claims, No Drawings

1,3-OXAZINES AS BACE1 AND/OR BACE2 INHIBITORS

PRIORITY TO RELATED APPLICATION(S)

This application claims priority to and is a continuation of pending U.S. application Ser. No. 13/439,893, filed Apr. 5, 2012, which in turn claims the benefit of European Patent Application No. 111618019, filed Apr. 11, 2011 both of which are hereby incorporated by reference in its entirety.

BACKGROUND OF THE INVENTION

Alzheimer's disease (AD) is a neurodegenerative disorder of the central nervous system and the leading cause of a progressive dementia in the elderly population. Its clinical symptoms are impairment of memory, cognition, temporal and local orientation, judgment and reasoning but also severe emotional disturbances. There are currently no treatments available which can prevent the disease or its progression or stably reverse its clinical symptoms. AD has become a major health problem in all societies with high life expectancies and also a significant economic burden for their health systems.

AD is characterized by 2 major pathologies in the central nervous system (CNS), the occurrence of amyloid plaques and neurofibrillar tangles (Hardy et al., The amyloid hypothesis of Alzheimer's disease: progress and problems on the road to therapeutics, *Science*. 2002 Jul. 19; 297(5580):353-6, Selkoe, Cell biology of the amyloid beta-protein precursor and the mechanism of Alzheimer's disease, *Annu Rev Cell Biol.* 1994; 10:373-403). Both pathologies are also commonly observed in patients with Down's syndrome (trisomy 21), which also develop AD-like symptoms in early life. Neurofibrillar tangles are intracellular aggregates of the microtubule-associated protein tau (MAPT). Amyloid plaques occur in the extracellular space; their principal components are Aβ-peptides. The latter are a group of proteolytic fragments derived from the β-amyloid precursor protein (APP) by a series of proteolytic cleavage steps. Several forms of APP have been identified of which the most abundant are proteins of 695, 751 and 770 amino acids length. They all arise from a single gene through differential splicing. The Aβ-peptides are derived from the same domain of the APP but differ at their N- and C-termini, the main species are of 40 and 42 amino-acid length. There are several lines of evidence which strongly suggest that aggregated Aβ-peptides are the essential molecules in the pathogenesis of AD: 1) amyloid plaques formed of Aβ-peptides are invariably part of the AD pathology; 2) Aβ-peptides are toxic for neurons; 3) in Familial Alzheimer's Disease (FAD) the mutations in the disease genes APP, PSN1, PSN2 lead to increased levels of Aβ-peptides and early brain amyloidosis; 4) transgenic mice which express such FAD genes develop a pathology which bears many resemblances to the human disease. Aβ-peptides are produced from APP through the sequential action of 2 proteolytic enzymes termed β- and γ-secretase. β-Secretase cleaves first in the extracellular domain of APP approximately 28 amino acids outside of the trans-membrane domain (TM) to produce a C-terminal fragment of APP containing the TM and the cytoplasmatic domain (CTFβ). CTFβ is the substrate for γ-secretase which cleaves at several adjacent positions within the TM to produce the Aβ peptides and the cytoplasmic fragment. The γ-secretase is a complex of at least 4 different proteins, its catalytic subunit is very likely a presenilin protein (PSEN1, PSEN2). The β-secretase (BACE1, Asp2; BACE stands for β-site APP-cleaving enzyme) is an aspartyl protease which is anchored into the membrane by a transmembrane domain (Vassar et al., Beta-secretase cleavage of Alzheimer's amyloid precursor protein by the transmembrane aspartic protease BACE, *Science*. 1999 Oct. 22; 286(5440): 735). It is expressed in many tissues of the human organism but its level is especially high in the CNS. Genetic ablation of the BACE1 gene in mice has clearly shown that its activity is essential for the processing of APP which leads to the generation of Aβ-peptides, in the absence of BACE1 no Aβ-peptides are produced (Luo et al., Mice deficient in BACE1, the Alzheimer's beta-secretase, have normal phenotype and abolished beta-amyloid generation, *Nat Neurosci*. 2001 March; 4(3):231-2, Roberds et al., BACE knockout mice are healthy despite lacking the primary beta-secretase activity in brain: implications for Alzheimer's disease therapeutics, *Hum Mol Genet.* 2001 Jun. 1; 10(12):1317-24). Mice which have been genetically engineered to express the human APP gene and which form extensive amyloid plaques and Alzheimer's disease like pathologies during aging fail to do so when β-secretase activity is reduced by genetic ablation of one of the BACE1 alleles (McConlogue et al., Partial reduction of BACE1 has dramatic effects on Alzheimer plaque and synaptic pathology in APP Transgenic Mice. *J Biol Chem*. 2007 Sep. 7; 282(36):26326). It is thus presumed that inhibitors of BACE1 activity can be useful agents for therapeutic intervention in Alzheimer's disease (AD).

Type 2 diabetes (T2D) is caused by insulin resistance and inadequate insulin secretion from pancreatic β-cells leading to poor blood-glucose control and hyperglycemia (M Prentki & C J Nolan, "Islet beta-cell failure in type 2 diabetes." J. Clin. Investig. 2006, 116(7), 1802-1812). Patients with T2D have an increased risk of microvascular and macrovascular disease and a range of related complications including diabetic nephropathy, retinopathy and cardiovascular disease. In 2000, an estimated 171 million people had the condition with the expectation that this FIGURE will double by 2030 (S Wild, G Roglic, A Green, R. Sicree & H King, "Global prevalence of diabetes", Diabetes Care 2004, 27(5), 1047-1053), making the disease a major healthcare problem. The rise in prevalence of T2D is associated with an increasingly sedentary lifestyle and high-energy food intake of the world's population (P Zimmet, K G M M Alberti & J Shaw, "Global and societal implications of the diabetes epidemic" Nature 2001, 414, 782-787). β-Cell failure and consequent dramatic decline in insulin secretion and hyperglycemia marks the onset of T2D. Most current treatments do not prevent the loss of β-cell mass characterizing overt T2D. However, recent developments with GLP-1 analogues, gastrin and other agents show that preservation and proliferation of β-cells is possible to achieve, leading to an improved glucose tolerance and slower progression to overt T2D (L L Baggio & D J Drucker, "Therapeutic approaches to preserve islet mass in type 2 diabetes", Annu. Rev. Med. 2006, 57, 265-281).

Tmem27 has been identified as a protein promoting beta-cell proliferation (P Akpinar, S Kuwajima, J Krützfeldt, M Stoffel, "Tmem27: A cleaved and shed plasma membrane protein that stimulates pancreatic β cell proliferation", Cell Metab. 2005, 2, 385-397) and insulin secretion (K Fukui, Q Yang, Y Cao, N Takahashi et al., "The HNF-1 target Collectrin controls insulin exocytosis by SNARE complex formation", Cell Metab. 2005, 2, 373-384). Tmem27 is a 42 kDa membrane glycoprotein which is constitutively shed from the surface of β-cells, resulting from a degradation of the full-length cellular Tmem27. Overexpression of Tmem27 in a transgenic mouse increases β-cell mass and improves glucose tolerance in a diet-induced obesity DIO model of diabetes. Furthermore, siRNA knockout of Tmem27 in a rodent β-cell proliferation assay (e.g. using INS1e cells) reduces the proliferation rate, indicating a role for Tmem27 in control of β-cell mass.

In the same proliferation assay, BACE2 inhibitors also increase proliferation. However, BACE2 inhibition combined with Tmem27 siRNA knockdown results in low proliferation rates. Therefore, it is concluded that BACE2 is the protease responsible for the degradation of Tmem27. Furthermore, in vitro, BACE2 cleaves a peptide based on the sequence of Tmem27. The closely related protease BACE1 does not cleave this peptide and selective inhibition of BACE1 alone does not enhance proliferation of β-cells.

The close homolog BACE2 is a membrane-bound aspartyl protease and is co-localized with Tmem27 in human pancreatic β-cells (G Finzi, F Franzi, C Placidi, F Acquati et al., "BACE2 is stored in secretory granules of mouse and rat pancreatic beta cells", Ultrastruct Pathol. 2008, 32(6), 246-251). It is also known to be capable of degrading APP (I Hussain, D Powell, D Howlett, G Chapman et al., "ASP1 (BACE2) cleaves the amyloid precursor protein at the β-secretase site" Mol Cell Neurosci. 2000, 16, 609-619), IL-1R2 (P Kuhn, E Marjaux, A Imhof, B De Strooper et al., "Regulated intramembrane proteolysis of the interleukin-1 receptor II by alpha-, beta-, and gamma-secretase" J. Biol. Chem. 2007, 282(16), 11982-11995) and ACE2. The capability to degrade ACE2 indicates a possible role of BACE2 in the control of hypertension.

Inhibition of BACE2 is therefore proposed as a treatment for T2D with the potential to preserve and restore β-cell mass and stimulate insulin secretion in pre-diabetic and diabetic patients. It is therefore an object of the present invention to provide selective BACE2 inhibitors. Such compounds are useful as therapeutically active substances, particularly in the treatment and/or prevention of diseases which are associated with the inhibition of BACE2.

Furthermore, the formation, or formation and deposition, of β-amyloid peptides in, on or around neurological tissue (e.g., the brain) are inhibited by the present compounds, i.e. inhibition of the Aβ-production from APP or an APP fragment.

Inhibitors of BACE1 and/or BACE2 can in addition be used to treat the following diseases:
IBM (inclusion body myositis) (Vattemi G. et al., Lancet. 2001 Dec. 8; 358(9297): 1962-4), Down's Syndrome (Barbiero L. et al, Exp Neurol. 2003 August; 182(2):335-45), Wilson's Disease (Sugimoto I. et al., J Biol. Chem. 2007 Nov. 30; 282(48):34896-903), Whipple's disease (Desnues B. et al., Clin Vaccine Immunol. 2006 February; 13(2):170-8), SpinoCerebellar Ataxia 1 and SpinoCerebellar Ataxia 7 (Gatchel J. R. et al., *Proc Natl Acad Sci USA* 2008 Jan. 29; 105(4):1291-6), Dermatomyositis (Greenberg S. A. et al., Ann Neurol. 2005 May; 57(5):664-78 and Greenberg S. A. et al., *Neurol* 2005 May; 57(5):664-78), Kaposi Sarcoma (Lagos D. et al, Blood, 2007 Feb. 15; 109(4):1550-8), Glioblastoma multiforme (E-MEXP-2576, http://www.ebi.ac.uk/microarray-as/aer/
result?queryFor=PhysicalArrayDesign&aAccession=A-MEXP-258), Rheumatoid arthritis (Ungethucm U. et al, GSE2053), Amyotrophic lateral sclerosis (Koistinen H. et al., Muscle Nerve. 2006 October; 34(4):444-50 and Li Q. X. et al, Aging Cell. 2006 April; 5(2):153-65), Huntington's Disease (Kim Y. J. et al., Neurobiol Dis. 2006 May; 22(2):346-56. Epub 2006 Jan. 19 and Hodges A. et al., Hum Mol Genet. 2006 Mar. 15; 15(6):965-77. Epub 2006 Feb. 8), Multiple Mieloma (Kihara Y. et al, Proc Natl Acad Sci USA. 2009 Dec. 22; 106(51):21807-12), Malignant melanoma (Talantov D. et al, Clin Cancer Res. 2005 Oct. 15; 11(20):7234-42), Sjogren syndrome (Basset C. et al., Scand J Immunol. 2000 March; 51(3):307-11), Lupus erythematosus (Grewal P. K. et al, Mol Cell Biol. 2006, July; 26(13):4970-81), Macrophagic myofasciitis, juvenile idiopathic arthritis, granulomatous arthritis, Breast cancer (Hedlund M. et al, Cancer Res. 2008 Jan. 15; 68(2):388-94 and Kondoh K. et al., Breast Cancer Res Treat. 2003 March; 78(1):37-44), Gastrointestinal diseases (Hoffmeister A. et al, JOP. 2009 Sep. 4; 10(5):501-6), Autoimmune/inflammatory diseases (Woodard-Grice A. V. et al., J Biol. Chem. 2008 Sep. 26; 283(39):26364-73. Epub 2008 Jul. 23), Rheumatoid Arthritis (Toegel S. et al, Osteoarthritis Cartilage. 2010 February; 18(2):240-8. Epub 2009 Sep. 22), Inflammatory reactions (Lichtcnthaler S. F. et al., J Biol Chem. 2003 Dec. 5; 278(49):48713-9. Epub 2003 Sep. 24), Arterial Thrombosis (Merten M. et al., Z Kardiol. 2004 November; 93(11):855-63), Cardiovascular diseases such as Myocardial infarction and stroke (Maugeri N. et al., Srp Arh Celok Lek. 2010 January; 138 Suppl 1:50-2) and Graves disease (Kiljański J. et al, Thyroid. 2005 July; 15(7):645-52).

FIELD OF THE INVENTION

The present invention provides 4-(3-amino-phenyl)-5,6-dihydro-4H-[1,3]oxazin-2-ylamines having BACE1 and/or BACE2 inhibitory properties, their manufacture, pharmaceutical compositions containing them and their use as therapeutically active substances.

SUMMARY OF THE INVENTION

The present invention provides novel compounds of formula I, their manufacture, medicaments based on a compound in accordance with the invention and their production as well as the use of compounds of formula I in the control or prevention of illnesses such as Alzheimer's disease and type 2 diabetes. Furthermore the use of compounds of formula I in the treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease and Wilson's Disease. The novel compounds of formula I have improved pharmacological properties.

The present invention provides a compounds of formula I,

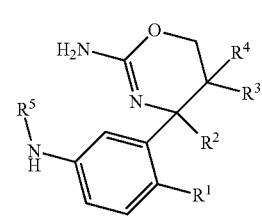

wherein the substituents and variables are as described below and in the claims, or a pharmaceutically acceptable salt thereof.

The present compounds have Asp2 (β-secretase, BACE1 or Memapsin-2) inhibitory activity and can therefore be used in the therapeutic and/or prophylactic treatment of diseases and disorders characterized by elevated β-amyloid levels and/or β-amyloid oligomers and/or β-amyloid plaques and further deposits, particularly Alzheimer's disease. And/or the present compounds have BACE2 inhibitory activity and can therefore be used in the therapeutic and/or prophylactic treatment of diseases and disorders such as type 2 diabetes and other metabolic disorders.

DETAILED DESCRIPTION OF THE INVENTION

The present invention provides a compound of formula I and their pharmaceutically acceptable salts thereof, the preparation of the above mentioned compounds, pharmaceutical compositions containing them and their manufacture as well as the use of the above mentioned compounds in the therapeutic and/or prophylactic treatment of diseases and disorders which are associated with inhibition of BACE1 and/or BACE2 activity, such as Alzheimer's disease and type 2 diabetes. Furthermore, the formation, or formation and deposition, of β-amyloid plaques in, on or around neurological tissue (e.g., the brain) are inhibited by the present compounds by inhibiting the Aβ production from APP or an APP fragment.

The following definitions of the general terms used in the present description apply irrespectively of whether the terms in question appear alone or in combination with other groups.

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

The term "$C_{1-6}$-alkyl", alone or in combination with other groups, stands for a hydrocarbon radical which can be linear or branched, with single or multiple branching, containing 1 to 6 carbon atoms, for example, methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl, 1,2-dimethyl-propyl and the like. The term "$C_{1-3}$-alkyl", alone or in combination with other groups, stands for a hydrocarbon radical which can be linear or branched, containing 1 to 3 carbon atoms. Particular "$C_{1-6}$-alkyl" are "$C_{1-3}$-alkyl". Specific examples are methyl and ethyl—most specifically methyl.

The term "cyano-$C_{1-6}$-alkyl", alone or in combination with other groups, refers to $C_{1-6}$-alkyl as defined herein, which is substituted by one or multiple cyano, particularly 1-5 cyano, more particularly 1 cyano. Examples are cyano-methyl and the like.

The term "halogen-$C_{1-6}$-alkyl", alone or in combination with other groups, refers to $C_{1-6}$-alkyl as defined herein, which is substituted by one or multiple halogen atoms, particularly 1-5 halogen atoms, more particularly 1-3 halogen atoms, most particularly 1 halogen atom or 3 halogen atoms. The term "halogen-$C_{1-3}$-alkyl", alone or in combination with other groups, refers to $C_{1-3}$-alkyl as defined herein, which is substituted by one or multiple halogen atoms, particularly 1-5 halogen atoms, more particularly 1-3 halogen atoms, most particularly 1 halogen atom or 3 halogen atoms. A particular halogen atom is fluoro. A particular "halogen-$C_{1-6}$-alkyl" is fluoro-$C_{1-6}$-alkyl, and a particular "halogen-$C_{1-3}$-alkyl" is fluoro-$C_{1-3}$-alkyl. Examples are difluoromethyl, chloromethyl, fluoromethyl and the like. Specific examples are trifluoromethyl, —$CH_2$—$CHF_2$ and —$CH_2$—$CH_2F$.

The term "$C_{1-6}$-alkoxy-$C_{1-6}$-alkyl", alone or in combination with other groups, refers to $C_{1-6}$-alkyl, which is substituted by one or multiple $C_{1-6}$-alkoxy as defined herein. Examples are MeO—$CH_2$—, 1MeO-Et, 2MeO-Et, 1MeO-2EtO-propyl and the like.

The term "$C_{3-6}$-cycloalkyl-$C_{1-6}$-alkyl", alone or in combination with other groups, refers to $C_{1-6}$-alkyl, which is substituted by one or multiple $C_{3-6}$-cycloalkyl as defined herein. Examples are cyclopropyl-methyl and the like.

The term "cyano", alone or in combination with other groups, refers to N≡C—.

The term "hydroxy", alone or in combination with other groups, refers to HO—.

The term "halogen", alone or in combination with other groups, denotes chloro (Cl), iodo (I), fluoro (F) and bromo (Br). Particular "halogen" atoms are Cl and F—specifically F.

The term "heteroaryl", alone or in combination with other groups, refers to a cyclic aromatic group of having a single 4 to 8 membered ring or multiple condensed rings comprising 6 to 14, in particular 6 to 10 ring atoms and containing 1, 2 or 3 heteroatoms individually selected from N, O and S, in particular N and O, in which group at least one heterocyclic ring is aromatic. Examples of "heteroaryl" include benzofuryl, benzoimidazolyl, 1H-benzoimidazolyl, benzooxazinyl, benzoxazolyl, benzothiazinyl, benzothiazolyl, benzothienyl, benzotriazolyl, furyl, imidazolyl, indazolyl, 1H-indazolyl, indolyl, isoquinolinyl, isothiazolyl, isoxazolyl, oxazolyl, pyrazinyl, pyrazolyl (pyrazyl), 1H-pyrazolyl, pyrazolo[1,5-a]pyridinyl, pyridazinyl, pyridinyl, pyrimidinyl, pyrrolyl, quinolinyl, tetrazolyl, thiazolyl, thienyl, triazolyl, 6,7-dihydro-5H-[1]pyrindinyl and the like. Particular "heteroaryl" are pyridinyl, pyrazinyl, furyl, thiazolyl, 2H-pyrazolyl and 1H-pyrazolyl. Specific examples are pyridine-2-yl, pyrazine-2-yl, furan-3-yl, thiazole-5-yl, 2H-pyrazole-3-yl and 1H-pyrazole-3-yl.

The term "heterocyclyl", alone or in combination with other groups, denotes a monovalent saturated or partly unsaturated mono- or bicyclic ring system of 4 to 9 ring atoms, containing 1, 2, or 3 ring heteroatoms selected from N, O and S, the remaining ring atoms being carbon. Bicyclic means consisting of two rings having two ring atoms in common, i.e. the bridge separating the two rings is either a single bond or a chain of one or two ring atoms. Examples for monocyclic saturated heterocyclyl are azetidinyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, and oxazepanyl. Examples for bicyclic saturated heterocyclyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, and 3-thia-9-aza-bicyclo[3.3.1]nonyl. Examples for partly unsaturated heterocyclyl are dihydrofuryl, imidazolinyl, dihydro-oxazolyl, tetrahydro-pyridinyl, and dihydropyranyl.

The term "$C_{1-6}$-alkoxy", alone or in combination with other groups, stands for an —O—$C_{1-6}$-alkyl radical which can be linear or branched, with single or multiple branching, wherein the alkyl group contains 1 to 6 carbon atoms, for example, methoxy (OMe), ethoxy (OEt), propoxy, isopropoxy (i-propoxy), n-butoxy, i-butoxy (iso-butoxy), 2-butoxy (sec-butoxy), t-butoxy (tert-butoxy), isopentyloxy (i-pentyloxy) and the like. Particular "$C_{1-6}$-alkoxy" are groups with 1 to 4 carbon atoms. Specific examples are methoxy and ethoxy.

The term "halogen-$C_{1-6}$-alkoxy", alone or in combination with other groups, refers to $C_{1-6}$-alkoxy as defined herein, which is substituted by one or multiple halogens, in particular fluoro. Particular "halogen-$C_{1-6}$-alkoxy" are fluoro-$C_{1-6}$-alkoxy. Specific examples are difluoromethoxy and trifluoromethoxy.

The term "$C_{3-6}$-cycloalkyl-$C_{1-6}$-alkoxy", alone or in combination with other groups, refers to $C_{1-6}$-alkoxy as defined herein, which is substituted by one or multiple "$C_{3-6}$-cycloalkyl" as defined herein, in particular cyclopropyl. Particular "$C_{3-6}$-cycloalkyl-$C_{1-6}$-alkoxy" is cyclopropyl-$C_{1-6}$-alkoxy. Specific examples are cyclopropyl-methoxy and cyclopropyl-ethoxy.

The term "$C_{3-6}$-cycloalkyl-$C_{2-6}$-alkynyl", alone or in combination with other groups, refers to a "$C_{3-6}$-cycloalkyl" as defined herein linked via a "$C_{2-6}$-alkynyl" as defined herein. A specific example is cyclopropyl-ethynyl.

The term "$C_{3-6}$-cycloalkyl", alone or in combination with other groups, denotes a monovalent saturated monocyclic or bicyclic hydrocarbon group of 3 to 6 ring carbon atoms, particularly a monovalent saturated monocyclic hydrocarbon group of 3 to 5 ring carbon atoms. Bicyclic means containing two saturated carbocyclic rings having two carbon atoms in common, i.e. the bridge separating the two rings is either a single bond or a chain of one or two carbon atoms. Particular $C_{3-6}$-cycloalkyl groups are monocyclic. Examples are cyclopropyl, cyclobutanyl, cyclopentyl, cyclohexyl and cycloheptyl. Examples for bicyclic cycloalkyl are bicyclo[2.2.1]heptanyl, bicyclo[2.2.2]octanyl and adamantanyl. A particular "$C_{3-6}$-cycloalkyl" is cyclohexyl.

The term "$C_{2-6}$-alkynyl", alone or in combination with other groups, denotes a monovalent linear or branched hydrocarbon group of 2 to 6 carbon atoms, in particular from 2 to 4 carbon atoms, and comprising one, two or three triple bonds. Examples of $C_{2-6}$-alkynyl include ethynyl, propynyl, prop-2-ynyl and n-butynyl. Specific examples are ethynyl and propynyl.

The term "$C_{2-6}$-alkynyl-$C_{1-6}$-alkoxy", alone or in combination with other groups, refers to a "$C_{2-6}$-alkynyl" as defined herein linked via a "$C_{1-6}$-alkoxy" as defined herein. A specific example is 5-but-2-ynyloxy.

The term "pharmaceutically acceptable salts" refers to salts that are suitable for use in contact with the tissues of humans and animals. Examples of suitable salts with inorganic and organic acids are, but are not limited to acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid, tartaric acid, trifluoroacetic acid and the like. In particular formic acid, trifluoroacetic acid and hydrochloric acid. Particular are hydrochloric acid, trifluoroacetic acid and fumaric acid.

The terms "pharmaceutically acceptable carrier" and "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. Particularly it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The term "inhibitor" denotes a compound which competes with, reduces or prevents the binding of a particular ligand to particular receptor or which reduces or prevents the inhibition of the function of a particular protein.

The term "half maximal inhibitory concentration" ($IC_{50}$) denotes the concentration of a particular compound required for obtaining 50% inhibition of a biological process in vitro. $IC_{50}$ values can be converted logarithmically to $pIC_{50}$ values (–log $IC_{50}$), in which higher values indicate exponentially greater potency. The $IC_{50}$ value is not an absolute value but depends on experimental conditions e.g. concentrations employed. The $IC_{50}$ value can be converted to an absolute inhibition constant (Ki) using the Cheng-Prusoff equation (Biochem. Pharmacol. (1973) 22:3099). The term "inhibition constant" (Ki) denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values (–log Ki), in which higher values indicate exponentially greater potency.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as preferred, more preferred and most preferred definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there can be one or more intermediates which are produced in the mixture which ultimately leads to the formation of the indicated and/or the desired product.

The term "protecting group" denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. The term "amino-protecting group" denotes groups intended to protect an amino group and includes benzyl, benzyloxycarbonyl (carbobenzyloxy, CBZ), 9-Fluorenylmethyloxycarbonyl (FMOC), p-methoxybenzyloxycarbonyl, p-nitrobenzyloxycarbonyl, tert-butoxycarbonyl (BOC), and trifluoroacetyl. Further examples of these groups are found in T. W. Greene and P. G. M. Wuts, "Protective Groups in Organic Synthesis", 2nd ed., John Wiley & Sons, Inc., New York, N.Y., 1991, chapter 7; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected amino group" refers to an amino group substituted by an amino-protecting groups. Particular amino-protecting groups are tert-butoxycarbonyl group, a bis(dimethoxyphenyl)-phenylmethyl and dimethoxytrityl.

The term "leaving group" denotes the group with the meaning conventionally associated with it in synthetic organic chemistry, i.e., an atom or group displaceable under substitution reaction conditions. Examples of leaving groups include halogen, in particular bromo, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, and acyloxy.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

Whenever a chiral carbon is present in a chemical structure, it is intended that all stereoisomers associated with that chiral carbon are encompassed by the structure.

The invention also provides pharmaceutical compositions, methods of using, and methods of preparing the aforementioned compounds.

All separate embodiments can be combined.

One embodiment of the invention is a compound of formula I,

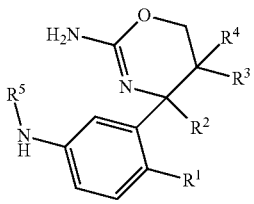

I wherein
$R^1$ is selected from the group consisting of
  hydrogen,
  halogen, and
  $C_{1-6}$-alkyl;
$R^2$ is selected from the group consisting of
  hydrogen,
  $C_{1-6}$-alkyl, and
  halogen-$C_{1-3}$-alkyl;
$R^3$ is selected from the group consisting of
  hydrogen and
  $C_{1-6}$-alkyl;
$R^4$ is selected from the group consisting of
  halogen,
  $C_{1-6}$-alkyl, and
  halogen-$C_{1-6}$-alkoxy;
$R^5$ is —C(=O)—$R^6$; and
$R^6$ is selected from the group consisting of
  heteroaryl,
  heteroaryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{3-6}$-cycloalkyl, $C_{3-6}$-cycloalkyl-$C_{1-6}$-alkoxy, $C_{3-6}$-cycloalkyl-$C_{1-6}$-alkyl, $C_{3-6}$-cycloalkyl-$C_{2-6}$-alkynyl, $C_{2-6}$-alkynyl-$C_{1-6}$-alkoxy and $C_{1-6}$-allyl,
  $C_{3-6}$-cycloalkyl,
  $C_{3-6}$-cycloalkyl substituted by 1-4 substituents individually selected from cyano, cyano-$C_{1-6}$-alkyl, halogen, halogen-$C_{1-6}$-alkoxy, halogen-$C_{1-6}$-alkyl, hydroxy, $C_{1-6}$-alkoxy, $C_{1-6}$-alkoxy-$C_{1-6}$-alkyl and $C_{1-6}$-alkyl,
  heterocyclyl, and
  heterocyclyl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl and $C_{1-6}$-alkyl;
or pharmaceutically acceptable salts thereof.

A certain embodiment of this invention provides a compound of formula Ia as described herein,

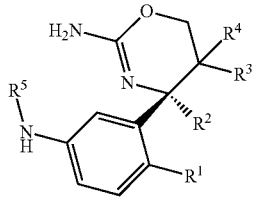

Ia wherein $R^1$, $R^2$, $R^3$, $R^4$, $R^5$ are as defined herein.

A certain embodiment of this invention provides a compound as described herein, wherein
$R^1$ is halogen;
$R^2$ is $C_{1-6}$-alkyl;
$R^3$ is selected from the group consisting of
  hydrogen and
  $C_{1-6}$-alkyl;
$R^4$ is selected from the group consisting of
  halogen and
  halogen-$C_{1-6}$-alkoxy;
$R^5$ is —C(=O)—$R^6$; and
$R^6$ is selected from the group consisting of
  heteroaryl,
  heteroaryl substituted by 1-4 substituents individually selected from cyano, halogen, halogen-$C_{1-6}$-alkoxy, halogen-$C_{1-6}$-alkyl, $C_{1-6}$-alkoxy, $C_{1-6}$-alkyl, $C_{3-6}$-cycloalkyl, $C_{3-6}$-cycloalkyl-$C_{1-6}$-alkoxy, $C_{2-6}$-alkynyl-$C_{1-6}$-alkoxy and $C_{3-6}$-cycloalkyl-$C_{2-6}$-alkynyl,
  $C_{3-6}$-cycloalkyl, and
  $C_{3-6}$-cycloalkyl substituted by 1-4 substituents individually selected from cyano and halogen,
or pharmaceutically acceptable salts thereof.

A certain embodiment of this invention provides a compound as described herein, wherein $R^1$ is halogen.

A certain embodiment of this invention provides a compound as described herein, wherein $R^1$ is F.

A certain embodiment of this invention provides a compound as described herein, wherein $R^1$ is hydrogen.

A certain embodiment of this invention provides a compound as described herein, wherein $R^1$ is $C_{1-6}$-alkyl.

A certain embodiment of this invention provides a compound as described herein, wherein $R^2$ is $C_{1-6}$-alkyl.

A certain embodiment of this invention provides a compound as described herein, wherein $R^2$ is Me.

A certain embodiment of this invention provides a compound as described herein, wherein $R^2$ is hydrogen.

A certain embodiment of this invention provides a compound as described herein, wherein $R^2$ is halogen-$C_{1-3}$-alkyl.

A certain embodiment of this invention provides a compound as described herein, wherein $R^2$ is —$CH_2$—$CHF_2$.

A certain embodiment of this invention provides a compound as described herein, wherein $R^2$ is —$CH_2$—$CH_2F$.

A certain embodiment of this invention provides a compound as described herein, wherein $R^3$ is hydrogen.

A certain embodiment of this invention provides a compound as described herein, wherein $R^3$ is $C_{1-6}$-alkyl.

A certain embodiment of this invention provides a compound as described herein, wherein $R^4$ is halogen.

A certain embodiment of this invention provides a compound as described herein, wherein $R^4$ is F.

A certain embodiment of this invention provides a compound as described herein, wherein $R^4$ is halogen-$C_{1-6}$-alkoxy.

A certain embodiment of this invention provides a compound as described herein, wherein $R^4$ is —$OCH_2CF_3$.

A certain embodiment of this invention provides a compound as described herein, wherein $R^4$ is $C_{1-6}$-alkyl.

A certain embodiment of this invention provides a compound as described herein, wherein $R^5$ is —C(=O)—$R^6$.

A certain embodiment of this invention provides a compound as described herein, wherein $R^6$ is heteroaryl.

A certain embodiment of this invention provides a compound as described herein, wherein $R^6$ is pyridine-2-yl.

A certain embodiment of this invention provides a compound as described herein, wherein $R^6$ is 1H-pyrazole-3-yl.

A certain embodiment of this invention provides a compound as described herein, wherein $R^6$ is 2H-pyrazole-3-yl.

A certain embodiment of this invention provides a compound as described herein, wherein $R^6$ is furan-3-yl.

A certain embodiment of this invention provides a compound as described herein, wherein $R^6$ is pyrazine-2-yl.

A certain embodiment of this invention provides a compound as described herein, wherein $R^6$ is thiazole-5-yl.

A certain embodiment of this invention provides a compound as described herein, wherein $R^6$ is pyridine-2-yl, 1H-pyrazole-3-yl, 2H-pyrazole-3-yl, pyrazine-2-yl, furan-3-yl or thiazole-5-yl.

A certain embodiment of this invention provides a compound as described herein, wherein $R^6$ is heteroaryl substituted by 1-2 substituents individually selected from cyano and halogen.

A certain embodiment of this invention provides a compound as described herein, wherein $R^6$ is 3-chloro-5-cyano-pyridine-2-yl.

A certain embodiment of this invention provides a compound as described herein, wherein $R^6$ is heteroaryl substituted by 1-2 substituents individually selected from halogen-$C_{1-6}$-alkyl and halogen.

A certain embodiment of this invention provides a compound as described herein, wherein $R^6$ is 3-fluoro-5-trifluoromethyl-pyridine-2-yl.

A certain embodiment of this invention provides a compound as described herein, wherein $R^6$ is 3-chloro-5-trifluoromethyl-pyridine-2-yl.

A certain embodiment of this invention provides a compound as described herein, wherein $R^6$ is 4-chloro-1-(2,2-difluoro-ethyl)-1H-pyrazole-3-yl.

A certain embodiment of this invention provides a compound as described herein, wherein $R^6$ is heteroaryl substituted by 1-2 halogen.

A certain embodiment of this invention provides a compound as described herein, wherein $R^6$ is 5-fluoro-pyridine-2-yl.

A certain embodiment of this invention provides a compound as described herein, wherein $R^6$ is 3,5-difluoro-pyridine-2-yl.

A certain embodiment of this invention provides a compound as described herein, wherein $R^6$ is 5-difluoromethyl-pyridine-2-yl.

A certain embodiment of this invention provides a compound as described herein, wherein $R^6$ is 5-chloro-3-fluoro-pyridine-2-yl.

A certain embodiment of this invention provides a compound as described herein, wherein $R^6$ is 3,5-dichloro-pyridine-2-yl.

A certain embodiment of this invention provides a compound as described herein, wherein $R^6$ is 5-chloro-pyridine-2-yl.

A certain embodiment of this invention provides a compound as described herein, wherein $R^6$ is 2-chloro-thiazole-5-yl.

A certain embodiment of this invention provides a compound as described herein, wherein $R^6$ is 4-chloro-1H-pyrazole-3-yl.

A certain embodiment of this invention provides a compound as described herein, wherein $R^6$ is heteroaryl substituted by cyano.

A certain embodiment of this invention provides a compound as described herein, wherein $R^6$ is 5-cyano-pyridine-2-yl.

A certain embodiment of this invention provides a compound as described herein, wherein $R^6$ is heteroaryl substituted by halogen-$C_{1-6}$-alkoxy.

A certain embodiment of this invention provides a compound as described herein, wherein $R^6$ is 5-fluoromethoxy-pyridine-2-yl.

A certain embodiment of this invention provides a compound as described herein, wherein $R^6$ is 5-fluoromethoxy-pyrazine-2-yl.

A certain embodiment of this invention provides a compound as described herein, wherein $R^6$ is 5-difluoromethoxy-pyridine-2-yl.

A certain embodiment of this invention provides a compound as described herein, wherein $R^6$ is 5-(2,2,2-trifluoro-ethoxy)-pyridine-2-yl.

A certain embodiment of this invention provides a compound as described herein, wherein $R^6$ is 5-(2,2,3,3,3-pentafluoro-propoxy)-pyridine-2-yl.

A certain embodiment of this invention provides a compound as described herein, wherein $R^6$ is 5-(2,2,3,3-tetrafluoro-propoxy)-pyridine-2-yl.

A certain embodiment of this invention provides a compound as described herein, wherein $R^6$ is 5-(2,2-difluoro-ethoxy)-pyrazine-2-yl.

A certain embodiment of this invention provides a compound as described herein, wherein $R^6$ is heteroaryl substituted by $C_{1-6}$-alkyl.

A certain embodiment of this invention provides a compound as described herein, wherein $R^6$ is 2,5-dimethyl-furan-3-yl.

A certain embodiment of this invention provides a compound as described herein, wherein $R^6$ is 1,5-dimethyl-1H-pyrazole-3-yl.

A certain embodiment of this invention provides a compound as described herein, wherein $R^6$ is heteroaryl substituted by $C_{3-6}$-cycloalkyl-$C_{1-6}$-alkyl.

A certain embodiment of this invention provides a compound as described herein, wherein $R^6$ is 5-cyclopropyl-pyridine-2-yl.

A certain embodiment of this invention provides a compound as described herein, wherein $R^6$ is heteroaryl substituted by $C_{3-6}$-cycloalkyl-$C_{2-6}$-alkynyl.

A certain embodiment of this invention provides a compound as described herein, wherein $R^6$ is 5-cyclopropylethynyl-pyridine-2-yl.

A certain embodiment of this invention provides a compound as described herein, wherein $R^6$ is heteroaryl substituted by $C_{2-6}$-alkynyl-$C_{1-6}$-alkoxy.

A certain embodiment of this invention provides a compound as described herein, wherein $R^6$ is 5-but-2-ynyloxy-pyrazine-2-yl.

A certain embodiment of this invention provides a compound as described herein, wherein $R^6$ is heteroaryl substituted by $C_{3-6}$-cycloalkyl-$C_{1-6}$-alkoxy.

A certain embodiment of this invention provides a compound as described herein, wherein $R^6$ is 5-cyclopropylmethoxy-pyrazine-2-yl.

A certain embodiment of this invention provides a compound as described herein, wherein $R^6$ is 5-cycloproropyl-methoxy-pyridine-2-yl.

A certain embodiment of this invention provides a compound as described herein, wherein $R^6$ is heteroaryl substituted by halogen-$C_{1-6}$-alkyl.

A certain embodiment of this invention provides a compound as described herein, wherein $R^6$ is 5-difluoromethyl-pyrazine-2-yl.

A certain embodiment of this invention provides a compound as described herein, wherein $R^6$ is heteroaryl substituted by halogen-$C_{1-6}$-alkyl and $C_{1-6}$-alkyl.

A certain embodiment of this invention provides a compound as described herein, wherein $R^6$ is 2-methyl-5-trifluoromethyl-2H-pyrazole-3-yl.

A certain embodiment of this invention provides a compound as described herein, wherein $R^6$ is heteroaryl substituted by $C_{1-6}$-alkoxy.

A certain embodiment of this invention provides a compound as described herein, wherein $R^6$ is 5-methoxy-pyridine-2-yl.

A certain embodiment of this invention provides a compound as described herein, wherein $R^6$ is heteroaryl substituted by 1-2 substituents individually selected from cyano, halogen and $C_{3-6}$-cycloalkyl-$C_{2-6}$-alkynyl.

A certain embodiment of this invention provides a compound as described herein, wherein $R^2$ is pyridinyl substituted by 1-2 substituents individually selected from cyano, chloro and cyclopropylethynyl-.

A certain embodiment of this invention provides a compound as described herein, selected from the group consisting of 5-Chloro-pyridine-2-carboxylic acid [3-((4R,5R)-2-amino-5-fluoro-4-methyl-5,6-dihydro-4H-[1,3]oxazin-4-yl)-4-fluoro-phenyl]-amide, 5-Cyano-pyridine-2-carboxylic acid [3-((4R,5R)-2-amino-5-fluoro-4-methyl-5,6-dihydro-4H-[1,3]oxazin-4-yl)-4-fluoro-phenyl]-amide, 5-Fluoromethoxy-pyridine-2-carboxylic acid [3-((4R,5R)-2-amino-5-fluoro-4-methyl-5,6-dihydro-4H-[1,3]oxazin-4-yl)-4-fluoro-phenyl]-amide, 5-Difluoromethoxy-pyridine-2-carboxylic acid [3-((4R,5R)-2-amino-5-fluoro-4-methyl-5,6-dihydro-4H-[1,3]oxazin-4-yl)-4-fluoro-phenyl]-amide, 3-Chloro-5-cyano-pyridine-2-carboxylic acid [3-((4R,5R)-2-amino-5-fluoro-4-methyl-5,6-dihydro-4H-[1,3]oxazin-4-yl)-4-fluoro-phenyl]-amide, 5-Chloro-3-fluoro-pyridine-2-carboxylic acid [3-((4R,5R)-2-amino-5-fluoro-4-methyl-5,6-dihydro-4H-[1,3]oxazin-4-yl)-4-fluoro-phenyl]-amide, 3-Chloro-5-trifluoromethyl-pyridine-2-carboxylic acid [3-((4R,5R)-2-amino-5-fluoro-4-methyl-5,6-dihydro-4H-[1,3]oxazin-4-yl)-4-fluoro-phenyl]-amide, 5-Fluoromethoxy-pyrazine-2-carboxylic acid [3-((4R,5R)-2-amino-5-fluoro-4-methyl-5,6-dihydro-4H-[1,3]oxazin-4-yl)-4-fluoro-phenyl]-amide, 5-Difluoromethyl-pyridine-2-carboxylic acid [3-((4R,5R)-2-amino-5-fluoro-4-methyl-5,6-dihydro-4H-[1,3]oxazin-4-yl)-4-fluoro-phenyl]-amide, 3-Fluoro-5-trifluoromethyl-pyridine-2-carboxylic acid [3-((4R,5R)-2-amino-5-fluoro-4-methyl-5,6-dihydro-4H-[1,3]oxazin-4-yl)-4-fluoro-phenyl]-amide, 5-Methoxy-pyridine-2-carboxylic acid [3-((4R,5R)-2-amino-5-fluoro-4-methyl-5,6-dihydro-4H-[1,3]oxazin-4-yl)-4-fluoro-phenyl]-amide, 5-Cyclopropylethynyl-pyridine-2-carboxylic acid [3-((4R,5R)-2-amino-5-fluoro-4-methyl-5,6-dihydro-4H-[1,3]oxazin-4-yl)-4-fluoro-phenyl]-amide, 5-Difluoromethyl-pyrazine-2-carboxylic acid [3-((4R,5R)-2-amino-5-fluoro-4-methyl-5,6-dihydro-4H-[1,3]oxazin-4-yl)-4-fluoro-phenyl]-amide, 5-Cyclopropylmethoxy-pyrazine-2-carboxylic acid [3-((4R,5R)-2-amino-5-fluoro-4-methyl-5,6-dihydro-4H-[1,3]oxazin-4-yl)-4-fluoro-phenyl]-amide, 5-Fluoro-pyridine-2-carboxylic acid [3-((4R,5R)-2-amino-5-fluoro-4-methyl-5,6-dihydro-4H-[1,3]oxazin-4-yl)-4-fluoro-phenyl]-amide, 5-Cyclopropyl-pyridine-2-carboxylic acid [3-((4R,5R)-2-amino-5-fluoro-4-methyl-5,6-dihydro-4H-[1,3]oxazin-4-yl)-4-fluoro-phenyl]-amide, 5-Cyclopropylmethoxy-pyridine-2-carboxylic acid [3-((4R,5R)-2-amino-5-fluoro-4-methyl-5,6-dihydro-4H-[1,3]oxazin-4-yl)-4-fluoro-phenyl]-amide, 2-Chloro-thiazole-5-carboxylic acid [3-((4R,5R)-2-amino-5-fluoro-4-methyl-5,6-dihydro-4H-[1,3]oxazin-4-yl)-4-fluoro-phenyl]-amide, 2-Methyl-5-trifluoromethyl-2H-pyrazole-3-carboxylic acid [3-((4R,5R)-2-amino-5-fluoro-4-methyl-5,6-dihydro-4H-[1,3]oxazin-4-yl)-4-fluoro-phenyl]-amide, 4-Chloro-1H-pyrazole-3-carboxylic acid [3-((4R,5R)-2-amino-5-fluoro-4-methyl-5,6-dihydro-4H-[1,3]oxazin-4-yl)-4-fluoro-phenyl]-amide, Thiazole-5-carboxylic acid [3-((4R,5R)-2-amino-5-fluoro-4-methyl-5,6-dihydro-4H-[1,3]oxazin-4-yl)-4-fluoro-phenyl]-amide, 1-Cyano-cyclopropanecarboxylic acid [3-((4R,5R)-2-amino-5-fluoro-4-methyl-5,6-dihydro-4H-[1,3]oxazin-4-yl)-4-fluoro-phenyl]-amide, Cyclopropanecarboxylic acid [3-((4R,5R)-2-amino-5-fluoro-4-methyl-5,6-dihydro-4H-[1,3]oxazin-4-yl)-4-fluoro-phenyl]-amide, 5-Cyano-pyridine-2-carboxylic acid [3-((4R,5S)-2-amino-5-fluoro-4-methyl-5,6-dihydro-4H-[1,3]oxazin-4-yl)-4-fluoro-phenyl]-amide, 5-Chloro-pyridine-2-carboxylic acid [3-((4R,5S)-2-amino-5-fluoro-4-methyl-5,6-dihydro-4H-[1,3]oxazin-4-yl)-4-fluoro-phenyl]-amide, 3-Chloro-5-cyano-pyridine-2-carboxylic acid [3-((4R,5S)-2-amino-5-fluoro-4-methyl-5,6-dihydro-4H-[1,3]oxazin-4-yl)-4-fluoro-phenyl]-amide, 3-Chloro-5-trifluoromethyl-pyridine-2-carboxylic acid [3-((4R,5S)-2-amino-5-fluoro-4-methyl-5,6-dihydro-4H-[1,3]oxazin-4-yl)-4-fluoro-phenyl]-amide, 5-Cyano-pyridine-2-carboxylic acid [3-((4R,5R)-2-amino-5-fluoro-4,5-dimethyl-5,6-dihydro-4H-[1,3]oxazin-4-yl)-4-fluoro-phenyl]-amide,
4-Chloro-1-difluoromethyl-1H-pyrazole-3-carboxylic acid [3-((4R,5R)-2-amino-5-fluoro-4,5-dimethyl-5,6-dihydro-4H-[1,3]oxazin-4-yl)-4-fluoro-phenyl]-amide,
5-Chloro-pyridine-2-carboxylic acid [3-((4R,5R)-2-amino-5-fluoro-4,5-dimethyl-5,6-dihydro-4H-[1,3]oxazin-4-yl)-4-fluoro-phenyl]-amide,
5-Fluoro-pyridine-2-carboxylic acid [3-((4R,5R)-2-amino-5-fluoro-4,5-dimethyl-5,6-dihydro-4H-[1,3]oxazin-4-yl)-4-fluoro-phenyl]-amide,
5-Chloro-pyridine-2-carboxylic acid {3-[(4R,5R)-2-amino-4-methyl-5-(2,2,2-trifluoro-ethoxy)-5,6-dihydro-4H-[1,3]oxazin-4-yl]-4-fluoro-phenyl}-amide,
5-Fluoro-pyridine-2-carboxylic acid {3-[(4R,5R)-2-amino-4-methyl-5-(2,2,2-trifluoro-ethoxy)-5,6-dihydro-4H-[1,3]oxazin-4-yl]-4-fluoro-phenyl}-amide,
5-Cyano-pyridine-2-carboxylic acid {3-[(4R,5R)-2-amino-4-methyl-5-(2,2,2-trifluoro-ethoxy)-5,6-dihydro-4H-[1,3]oxazin-4-yl]-4-fluoro-phenyl}-amide,
5-But-2-ynyloxy-pyrazine-2-carboxylic acid [3-((4R,5R)-2-amino-5-fluoro-4,5-dimethyl-5,6-dihydro-4H-[1,3]oxazin-4-yl)-4-fluoro-phenyl]-amide,
5-Cyano-pyridine-2-carboxylic acid [3-((4S,5R)-2-amino-5-fluoro-4-fluoromethyl-5,6-dihydro-4H-[1,3]oxazin-4-yl)-4-fluoro-phenyl]-amide,
5-Cyano-pyridine-2-carboxylic acid [3-((4S,5S)-2-amino-5-fluoro-4-fluoromethyl-5,6-dihydro-4H-[1,3]oxazin-4-yl)-4-fluoro-phenyl]-amide,
5-Cyano-pyridine-2-carboxylic acid [3-((4R,5R)- or (4R,5S)-2-amino-4-difluoromethyl-5-fluoro-5,6-dihydro-4H-[1,3]oxazin-4-yl)-4-fluoro-phenyl]-amide,
5-(2,2,2-Trifluoro-ethoxy)-pyridine-2-carboxylic acid [3-((4R,5R)-2-amino-5-fluoro-4-methyl-5,6-dihydro-4H-[1,3]oxazin-4-yl)-4-fluoro-phenyl]-amide,
3-(2,2,2-Trifluoro-ethoxy)-pyridine-2-carboxylic acid [3-((4R,5R)-2-amino-5-fluoro-4,5-dimethyl-5,6-dihydro-4H-[1,3]oxazin-4-yl)-4-fluoro-phenyl]-amide,
5-(2,2,2-Trifluoro-ethoxy)-pyridine-2-carboxylic acid {3-[(4R,5R)-2-amino-4-methyl-5-(2,2,2-trifluoro-ethoxy)-5,6-dihydro-4H-[1,3]oxazin-4-yl]-4-fluoro-phenyl}-amide,
5-(2,2,3,3-Tetrafluoro-propoxy)-pyridine-2-carboxylic acid [3-((4R,5R)-2-amino-5-fluoro-4-methyl-5,6-dihydro-4H-[1,3]oxazin-4-yl)-4-fluoro-phenyl]-amide,
5-(2,2,3,3,3-Pentafluoro-propoxy)-pyridine-2-carboxylic acid [3-((4R,5R)-2-amino-5-fluoro-4-methyl-5,6-dihydro-4H-[1,3]oxazin-4-yl)-4-fluoro-phenyl]-amide,
1,5-Dimethyl-1H-pyrazole-3-carboxylic acid [3-((4R,5R)-2-amino-5-fluoro-4-methyl-5,6-dihydro-4H-[1,3]oxazin-4-yl)-4-fluoro-phenyl]-amide,
5-(2,2-Difluoro-ethoxy)-pyrazine-2-carboxylic acid [3-((4R,5R)-2-amino-5-fluoro-4-methyl-5,6-dihydro-4H-[1,3]oxazin-4-yl)-4-fluoro-phenyl]-amide,
5-(2,2-Difluoro-ethoxy)-pyridine-2-carboxylic acid [3-((4R,5R)-2-amino-5-fluoro-4-methyl-5,6-dihydro-4H-[1,3]oxazin-4-yl)-4-fluoro-phenyl]-amide,
4-Chloro-1-(2,2-difluoro-ethyl)-1H-pyrazole-3-carboxylic acid [3-((4R,5R)-2-amino-5-fluoro-4,5-dimethyl-5,6-dihydro-4H-[1,3]oxazin-4-yl)-4-fluoro-phenyl]-amide,
2,2-Difluoro-cyclopropanecarboxylic acid [3-((4R,5R)-2-amino-5-fluoro-4,5-dimethyl-5,6-dihydro-4H-[1,3]oxazin-4-yl)-4-fluoro-phenyl]-amide,
2,5-Dimethyl-furan-3-carboxylic acid [3-((4R,5R)-2-amino-5-fluoro-4-methyl-5,6-dihydro-4H-[1,3]oxazin-4-yl)-4-fluoro-phenyl]-amide,
3,5-Dichloro-pyridine-2-carboxylic acid [3-((4R,5R)-2-amino-5-fluoro-4-methyl-5,6-dihydro-4H-[1,3]oxazin-4-yl)-4-fluoro-phenyl]-amide,
3,5-Difluoro-pyridine-2-carboxylic acid [3-((4R,5R)-2-amino-5-fluoro-4-methyl-5,6-dihydro-4H-[1,3]oxazin-4-yl)-4-fluoro-phenyl]-amide,
3,5-Dichloro-pyridine-2-carboxylic acid [3-((4R,5R)-2-amino-5-fluoro-4,5-dimethyl-5,6-dihydro-4H-[1,3]oxazin-4-yl)-4-fluoro-phenyl]-amide, and
3,5-Dichloro-pyridine-2-carboxylic acid {3-[(4R,5R)-2-amino-4-methyl-5-(2,2,2-trifluoro-ethoxy)-5,6-dihydro-4H-[1,3]oxazin-4-yl]-4-fluoro-phenyl}-amide,
or a pharmaceutical acceptable salt thereof.

A certain embodiment of this invention provides a compound as described herein, selected from the group consisting of 5-Chloro-pyridine-2-carboxylic acid [3-((4R,5R)-2-amino-5-fluoro-4-methyl-5,6-dihydro-4H-[1,3]oxazin-4-yl)-4-fluoro-phenyl]-amide,
1,5-Dimethyl-1H-pyrazole-3-carboxylic acid [3-((4R,5R)-2-amino-5-fluoro-4-methyl-5,6-dihydro-4H-[1,3]oxazin-4-yl)-4-fluoro-phenyl]-amide,
1-Cyano-cyclopropanecarboxylic acid [3-((4R,5R)-2-amino-5-fluoro-4-methyl-5,6-dihydro-4H-[1,3]oxazin-4-yl)-4-fluoro-phenyl]-amide,
2,2-Difluoro-cyclopropanecarboxylic acid [3-((4R,5R)-2-amino-5-fluoro-4,5-dimethyl-5,6-dihydro-4H-[1,3]oxazin-4-yl)-4-fluoro-phenyl]-amide,
2,5-Dimethyl-furan-3-carboxylic acid [3-((4R,5R)-2-amino-5-fluoro-4-methyl-5,6-dihydro-4H-[1,3]oxazin-4-yl)-4-fluoro-phenyl]-amide,
2-Chloro-thiazole-5-carboxylic acid [3-((4R,5R)-2-amino-5-fluoro-4-methyl-5,6-dihydro-4H-[1,3]oxazin-4-yl)-4-fluoro-phenyl]-amide,
2-Methyl-5-trifluoromethyl-2H-pyrazole-3-carboxylic acid [3-((4R,5R)-2-amino-5-fluoro-4-methyl-5,6-dihydro-4H-[1,3]oxazin-4-yl)-4-fluoro-phenyl]-amide,
3-(2,2,2-Trifluoro-ethoxy)-pyridine-2-carboxylic acid [3-((4R,5R)-2-amino-5-fluoro-4,5-dimethyl-5,6-dihydro-4H-[1,3]oxazin-4-yl)-4-fluoro-phenyl]-amide,
3,5-Dichloro-pyridine-2-carboxylic acid [3-((4R,5R)-2-amino-5-fluoro-4-methyl-5,6-dihydro-4H-[1,3]oxazin-4-yl)-4-fluoro-phenyl]-amide,
3,5-Dichloro-pyridine-2-carboxylic acid [3-((4R,5R)-2-amino-5-fluoro-4,5-dimethyl-5,6-dihydro-4H-[1,3]oxazin-4-yl)-4-fluoro-phenyl]-amide,
3,5-Dichloro-pyridine-2-carboxylic acid [3-((4R,5R)-2-amino-5-fluoro-4,5-dimethyl-5,6-dihydro-4H-[1,3]oxazin-4-yl)-4-fluoro-phenyl]-amide,
3,5-Dichloro-pyridine-2-carboxylic acid {3-[(4R,5R)-2-amino-4-methyl-5-(2,2,2-trifluoro-ethoxy)-5,6-dihydro-4H-[1,3]oxazin-4-yl]-4-fluoro-phenyl}-amide,
3,5-Difluoro-pyridine-2-carboxylic acid [3-((4R,5R)-2-amino-5-fluoro-4-methyl-5,6-dihydro-4H-[1,3]oxazin-4-yl)-4-fluoro-phenyl]-amide,
3-Chloro-5-cyano-pyridine-2-carboxylic acid [3-((4R,5R)-2-amino-5-fluoro-4-methyl-5,6-dihydro-4H-[1,3]oxazin-4-yl)-4-fluoro-phenyl]-amide,
3-Chloro-5-cyano-pyridine-2-carboxylic acid [3-((4R,5S)-2-amino-5-fluoro-4-methyl-5,6-dihydro-4H-[1,3]oxazin-4-yl)-4-fluoro-phenyl]-amide,
3-Chloro-5-trifluoromethyl-pyridine-2-carboxylic acid [3-((4R,5R)-2-amino-5-fluoro-4-methyl-5,6-dihydro-4H-[1,3]oxazin-4-yl)-4-fluoro-phenyl]-amide,
3-Chloro-5-trifluoromethyl-pyridine-2-carboxylic acid [3-((4R,5S)-2-amino-5-fluoro-4-methyl-5,6-dihydro-4H-[1,3]oxazin-4-yl)-4-fluoro-phenyl]-amide, 3-Fluoro-5-trifluoromethyl-pyridine-2-carboxylic acid [3-((4R,5R)-2-amino-5-fluoro-4-methyl-5,6-dihydro-4H-[1,3]oxazin-4-yl)-4-fluoro-phenyl]-amide,
4-Chloro-1-(2,2-difluoro-ethyl)-1H-pyrazole-3-carboxylic acid [3-((4R,5R)-2-amino-5-fluoro-4,5-dimethyl-5,6-dihydro-4H-[1,3]oxazin-4-yl)-4-fluoro-phenyl]-amide,
4-Chloro-1H-pyrazole-3-carboxylic acid [3-((4R,5R)-2-amino-5-fluoro-4-methyl-5,6-dihydro-4H-[1,3]oxazin-4-yl)-4-fluoro-phenyl]-amide,
5-(2,2,2-Trifluoro-ethoxy)-pyridine-2-carboxylic acid [3-((4R,5R)-2-amino-5-fluoro-4-methyl-5,6-dihydro-4H-[1,3]oxazin-4-yl)-4-fluoro-phenyl]-amide,
5-(2,2,2-Trifluoro-ethoxy)-pyridine-2-carboxylic acid {3-[(4R,5R)-2-amino-4-methyl-5-(2,2,2-trifluoro-ethoxy)-5,6-dihydro-4H-[1,3]oxazin-4-yl]-4-fluoro-phenyl}-amide,
5-(2,2,3,3,3-Pentafluoro-propoxy)-pyridine-2-carboxylic acid [3-((4R,5R)-2-amino-5-fluoro-4-methyl-5,6-dihydro-4H-[1,3]oxazin-4-yl)-4-fluoro-phenyl]-amide,
5-(2,2,3,3-Tetrafluoro-propoxy)-pyridine-2-carboxylic acid [3-((4R,5R)-2-amino-5-fluoro-4-methyl-5,6-dihydro-4H-[1,3]oxazin-4-yl)-4-fluoro-phenyl]-amide,
5-(2,2-Difluoro-ethoxy)-pyrazine-2-carboxylic acid [3-((4R,5R)-2-amino-5-fluoro-4-methyl-5,6-dihydro-4H-[1,3]oxazin-4-yl)-4-fluoro-phenyl]-amide,
5-(2,2-Difluoro-ethoxy)-pyridine-2-carboxylic acid [3-((4R,5R)-2-amino-5-fluoro-4-methyl-5,6-dihydro-4H-[1,3]oxazin-4-yl)-4-fluoro-phenyl]-amide,
5-Chloro-3-fluoro-pyridine-2-carboxylic acid [3-((4R,5R)-2-amino-5-fluoro-4-methyl-5,6-dihydro-4H-[1,3]oxazin-4-yl)-4-fluoro-phenyl]-amide,
5-Chloro-pyridine-2-carboxylic acid [3-((4R,5R)-2-amino-5-fluoro-4,5-dimethyl-5,6-dihydro-4H-[1,3]oxazin-4-yl)-4-fluoro-phenyl]-amide,
5-Chloro-pyridine-2-carboxylic acid [3-((4R,5S)-2-amino-5-fluoro-4-methyl-5,6-dihydro-4H-[1,3]oxazin-4-yl)-4-fluoro-phenyl]-amide,
5-Chloro-pyridine-2-carboxylic acid {3-[(4R,5R)-2-amino-4-methyl-5-(2,2,2-trifluoro-ethoxy)-5,6-dihydro-4H-[1,3]oxazin-4-yl]-4-fluoro-phenyl}-amide,
5-Cyano-pyridine-2-carboxylic acid [3-((4R,5R)-2-amino-5-fluoro-4-methyl-5,6-dihydro-4H-[1,3]oxazin-4-yl)-4-fluoro-phenyl]-amide,
5-Cyano-pyridine-2-carboxylic acid [3-((4R,5R)-2-amino-5-fluoro-4,5-dimethyl-5,6-dihydro-4H-[1,3]oxazin-4-yl)-4-fluoro-phenyl]-amide,
5-Cyano-pyridine-2-carboxylic acid [3-((4R,5S)-2-amino-5-fluoro-4-methyl-5,6-dihydro-4H-[1,3]oxazin-4-yl)-4-fluoro-phenyl]-amide,
5-Cyano-pyridine-2-carboxylic acid {3-[(4R,5R)-2-amino-4-methyl-5-(2,2,2-trifluoro-ethoxy)-5,6-dihydro-4H-[1,3]oxazin-4-yl]-4-fluoro-phenyl}-amide,
5-Cyclopropylethynyl-pyridine-2-carboxylic acid [3-((4R,5R)-2-amino-5-fluoro-4-methyl-5,6-dihydro-4H-[1,3]oxazin-4-yl)-4-fluoro-phenyl]-amide,
5-Cyclopropylmethoxy-pyrazine-2-carboxylic acid [3-((4R,5R)-2-amino-5-fluoro-4-methyl-5,6-dihydro-4H-[1,3]oxazin-4-yl)-4-fluoro-phenyl]-amide,
5-Cyclopropylmethoxy-pyridine-2-carboxylic acid [3-((4R,5R)-2-amino-5-fluoro-4-methyl-5,6-dihydro-4H-[1,3]oxazin-4-yl)-4-fluoro-phenyl]-amide,
5-Cyclopropyl-pyridine-2-carboxylic acid [3-((4R,5R)-2-amino-5-fluoro-4-methyl-5,6-dihydro-4H-[1,3]oxazin-4-yl)-4-fluoro-phenyl]-amide,
5-Difluoromethoxy-pyridine-2-carboxylic acid [3-((4R,5R)-2-amino-5-fluoro-4-methyl-5,6-dihydro-4H-[1,3]oxazin-4-yl)-4-fluoro-phenyl]-amide,
5-Difluoromethyl-pyrazine-2-carboxylic acid [3-((4R,5R)-2-amino-5-fluoro-4-methyl-5,6-dihydro-4H-[1,3]oxazin-4-yl)-4-fluoro-phenyl]-amide,
5-Difluoromethyl-pyridine-2-carboxylic acid [3-((4R,5R)-2-amino-5-fluoro-4-methyl-5,6-dihydro-4H-[1,3]oxazin-4-yl)-4-fluoro-phenyl]-amide,
5-Fluoromethoxy-pyrazine-2-carboxylic acid [3-((4R,5R)-2-amino-5-fluoro-4-methyl-5,6-dihydro-4H-[1,3]oxazin-4-yl)-4-fluoro-phenyl]-amide,
5-Fluoromethoxy-pyridine-2-carboxylic acid [3-((4R,5R)-2-amino-5-fluoro-4-methyl-5,6-dihydro-4H-[1,3]oxazin-4-yl)-4-fluoro-phenyl]-amide,
5-Fluoro-pyridine-2-carboxylic acid [3-((4R,5R)-2-amino-5-fluoro-4-methyl-5,6-dihydro-4H-[1,3]oxazin-4-yl)-4-fluoro-phenyl]-amide,
5-Fluoro-pyridine-2-carboxylic acid [3-((4R,5R)-2-amino-5-fluoro-4,5-dimethyl-5,6-dihydro-4H-[1,3]oxazin-4-yl)-4-fluoro-phenyl]-amide,
5-Fluoro-pyridine-2-carboxylic acid {3-[(4R,5R)-2-amino-4-methyl-5-(2,2,2-trifluoro-ethoxy)-5,6-dihydro-4H-[1,3]oxazin-4-yl]-4-fluoro-phenyl}-amide,
5-Methoxy-pyridine-2-carboxylic acid [3-((4R,5R)-2-amino-5-fluoro-4-methyl-5,6-dihydro-4H-[1,3]oxazin-4-yl)-4-fluoro-phenyl]-amide,
Cyclopropanecarboxylic acid [3-((4R,5R)-2-amino-5-fluoro-4-methyl-5,6-dihydro-4H-[1,3]oxazin-4-yl)-4-fluoro-phenyl]-amide,
Thiazole-5-carboxylic acid [3-((4R,5R)-2-amino-5-fluoro-4-methyl-5,6-dihydro-4H-[1,3]oxazin-4-yl)-4-fluoro-phenyl]-amide, and
5-But-2-ynyloxy-pyrazine-2-carboxylic acid [3-((4R,5R)-2-amino-5-fluoro-4,5-dimethyl-5,6-dihydro-4H-[1,3]oxazin-4-yl)-4-fluoro-phenyl]-amide,
or a pharmaceutical acceptable salt thereof.

A certain embodiment of this invention provides a compound as described herein, selected from the group consisting of
5-Chloro-pyridine-2-carboxylic acid [3-((4R,5R)-2-amino-5-fluoro-4-methyl-5,6-dihydro-4H-[1,3]oxazin-4-yl)-4-fluoro-phenyl]-amide,
3,5-Dichloro-pyridine-2-carboxylic acid [3-((4R,5R)-2-amino-5-fluoro-4-methyl-5,6-dihydro-4H-[1,3]oxazin-4-yl)-4-fluoro-phenyl]-amide,
5-Cyano-pyridine-2-carboxylic acid [3-((4R,5R)-2-amino-5-fluoro-4-methyl-5,6-dihydro-4H-[1,3]oxazin-4-yl)-4-fluoro-phenyl]-amide,
5-Cyano-pyridine-2-carboxylic acid {3-[(4R,5R)-2-amino-4-methyl-5-(2,2,2-trifluoro-ethoxy)-5,6-dihydro-4H-[1,3]oxazin-4-yl]-4-fluoro-phenyl}-amide, and
5-Cyclopropylethynyl-pyridine-2-carboxylic acid [3-((4R,5R)-2-amino-5-fluoro-4-methyl-5,6-dihydro-4H-[1,3]oxazin-4-yl)-4-fluoro-phenyl]-amide,
or a pharmaceutical acceptable salt thereof.

A certain embodiment of this invention provides a compound as described herein, which is 5-Chloro-pyridine-2-carboxylic acid [3-((4R,5R)-2-amino-5-fluoro-4-methyl-5,6-dihydro-4H-[1,3]oxazin-4-yl)-4-fluoro-phenyl]-amide.

A certain embodiment of this invention provides a compound as described herein, which is 3,5-Dichloro-pyridine-2-carboxylic acid [3-((4R,5R)-2-amino-5-fluoro-4-methyl-5,6-dihydro-4H-[1,3]oxazin-4-yl)-4-fluoro-phenyl]-amide.

A certain embodiment of this invention provides a compound as described herein, which is 5-Cyano-pyridine-2-carboxylic acid [3-((4R,5R)-2-amino-5-fluoro-4-methyl-5,6-dihydro-4H-[1,3]oxazin-4-yl)-4-fluoro-phenyl]-amide.

A certain embodiment of this invention provides a compound as described herein, which is 5-Cyano-pyridine-2-carboxylic acid {3-[(4R,5R)-2-amino-4-methyl-5-(2,2,2-trifluoro-ethoxy)-5,6-dihydro-4H-[1,3]oxazin-4-yl]-4-fluoro-phenyl}-amide.

A certain embodiment of this invention provides a compound as described herein, which is 5-Cyclopropylethynyl-pyridine-2-carboxylic acid [3-((4R,5R)-2-amino-5-fluoro-4-methyl-5,6-dihydro-4H-[1,3]oxazin-4-yl)-4-fluoro-phenyl]-amide.

A certain embodiment of this invention provides a compound as described herein, which process comprises reacting a compound of formula C4 to a compound of formula I

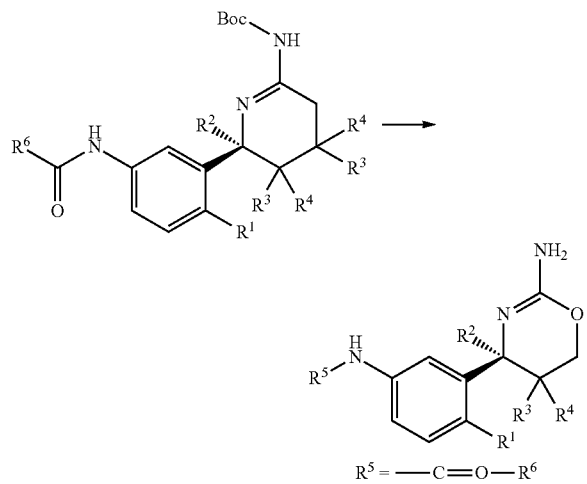

wherein $R^1$, $R^2$, $R^3$, $R^4$, $R^5$ and $R^6$ are as defined herein.

A certain embodiment of the invention provides a compound of formula I as described herein, whenever prepared by a process as defined above.

A certain embodiment of the invention provides a compound of formula I as described herein for use as therapeutically active substance.

A certain embodiment of the invention provides a compound of formula I as described herein for the use as inhibitor of BACE1 and/or BACE2 activity.

A certain embodiment of the invention provides a compound of formula I as described herein for the use as inhibitor of BACE1 activity.

A certain embodiment of the invention provides a compound of formula I as described herein for the use as inhibitor of BACE2 activity.

A certain embodiment of the invention provides a compound of formula I as described herein for the use as inhibitor of BACE1 and BACE2 activity.

A certain embodiment of the invention provides a compound of formula I as described herein for the use as therapeutically active substance for the therapeutic and/or prophylactic treatment of diseases and disorders characterized by elevated μ-amyloid levels and/or β-amyloid oligomers and/or β-amyloid plaques and further deposits or Alzheimer's disease.

A certain embodiment of the invention provides a compound of formula I as described herein for the use as therapeutically active substance for the therapeutic and/or prophylactic treatment of Alzheimer's disease.

A certain embodiment of the invention provides a compound of formula I as described herein for the use as therapeutically active substance for the therapeutic and/or prophylactic treatment of diabetes or type 2 diabetes.

A certain embodiment of the invention provides a compound of formula I as described herein for the use as therapeutically active substance for the therapeutic and/or prophylactic treatment of diabetes.

A certain embodiment of the invention provides a compound of formula I as described herein for the use as therapeutically active substance for the therapeutic and/or prophylactic treatment of diabetes or type 2 diabetes.

A certain embodiment of the invention provides a compound of formula I as described herein for the use as therapeutically active substance for the therapeutic and/or prophylactic treatment of Alzheimer's disease, diabetes or type 2 diabetes.

A certain embodiment of the invention provides a compound of formula I as described herein for the use as therapeutically active substance for the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease.

A certain embodiment of the invention provides a pharmaceutical composition comprising a compound of formula I as described herein and a pharmaceutically acceptable carrier and/or a pharmaceutically acceptable auxiliary substance.

A certain embodiment of the invention provides the use of a compound of formula I as described herein for the manufacture of a medicament for the use in inhibition of BACE1 and/or BACE2 activity.

A certain embodiment of the invention provides the use of a compound of formula I as described herein for the manufacture of a medicament for the use in inhibition of BACE1 activity.

A certain embodiment of the invention provides the use of a compound of formula I as described herein for the manufacture of a medicament for the use in inhibition of BACE2 activity.

A certain embodiment of the invention provides the use of a compound of formula I as described herein for the manufacture of a medicament for the use in inhibition of BACE1 and BACE2 activity.

A certain embodiment of the invention provides the use of a compound of formula I as described herein for the manufacture of a medicament for the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides the use of a compound of formula I as described herein for the manufacture of a medicament for the therapeutic and/or prophylactic treatment of Alzheimer's disease.

A certain embodiment of the invention provides the use of a compound of formula I as described herein for the manufacture of a medicament for the therapeutic and/or prophylactic treatment of diabetes or type 2 diabetes.

A certain embodiment of the invention provides the use of a compound of formula I as described herein for the manufacture of a medicament for the therapeutic and/or prophylactic treatment of diabetes.

A certain embodiment of the invention provides the use of a compound of formula I as described herein for the manufacture of a medicament for the therapeutic and/or prophylactic treatment of diabetes or type 2 diabetes.

A certain embodiment of the invention provides the use of a compound of formula I as described herein for the manufacture of a medicament for the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease.

A certain embodiment of the invention provides the use of a compound of formula I as described herein for the manufacture of a medicament for the therapeutic and/or prophylactic treatment of Alzheimer's disease, diabetes or type 2 diabetes.

A certain embodiment of the invention provides the use of a compound of formula I as described herein for the manufacture of a medicament for the therapeutic and/or prophylactic treatment of Alzheimer's disease.

A certain embodiment of the invention provides the use of a compound of formula I as described herein for the manufacture of a medicament for the therapeutic and/or prophylactic treatment of diabetes or type 2 diabetes.

A certain embodiment of the invention provides the use of a compound of formula I as described herein for the manufacture of a medicament for the therapeutic and/or prophylactic treatment of diabetes.

A certain embodiment of the invention provides the use of a compound of formula I as described herein for the manufacture of a medicament for the therapeutic and/or prophylactic treatment of type 2 diabetes.

A certain embodiment of the invention provides the use of a compound of formula I as described herein for the manufacture of a medicament for the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease.

A certain embodiment of the invention provides a compound of formula I as described herein for the use in inhibition of BACE1 and/or BACE2 activity.

A certain embodiment of the invention provides a compound of formula I as described herein for the use in inhibition of BACE1 activity.

A certain embodiment of the invention provides a compound of formula I as described herein for the use in inhibition of BACE2 activity.

A certain embodiment of the invention provides a compound of formula I as described herein for the use in inhibition of BACE1 and BACE2 activity.

A certain embodiment of the invention provides a compound of formula I as described herein for the use in the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides a compound of formula I as described herein for the use in the therapeutic and/or prophylactic treatment of Alzheimer's disease.

A certain embodiment of the invention provides a compound of formula I as described herein for the use in the therapeutic and/or prophylactic treatment of diabetes or type 2 diabetes.

A certain embodiment of the invention provides a compound of formula I as described herein for the use in the therapeutic and/or prophylactic treatment of diabetes.

A certain embodiment of the invention provides a compound of formula I as described herein for the use in the therapeutic and/or prophylactic treatment of diabetes or type 2 diabetes.

A certain embodiment of the invention provides a compound of formula I as described herein for the use in the therapeutic and/or prophylactic treatment of Alzheimer's disease, diabetes or type 2 diabetes.

A certain embodiment of the invention provides a compound of formula I as described herein for the use in the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease.

A certain embodiment of the invention provides a method for the use in inhibition of BACE1 and/or BACE2 activity, particularly for the therapeutic and/or prophylactic treatment of diseases and disorders characterized by elevated β-amyloid levels and/or β-amyloid oligomers and/or β-amyloid plaques and further deposits, Alzheimer's disease, diabetes or type 2 diabetes, which method comprises administering compound of formula I as described herein to a human being or animal.

A certain embodiment of the invention provides a method for the use in the therapeutic and/or prophylactic treatment of Alzheimer's disease, diabetes or type 2 diabetes, which method comprises administering a compound of formula I as described herein to a human being or animal.

A certain embodiment of the invention provides a method for the use in the therapeutic and/or prophylactic treatment of Alzheimer's disease, which method comprises administering a compound of formula I as described herein to a human being or animal.

A certain embodiment of the invention provides a method for the use in the therapeutic and/or prophylactic treatment of diabetes, which method comprises administering a compound of formula I as described herein to a human being or animal.

A certain embodiment of the invention provides a method for the use in the therapeutic and/or prophylactic treatment of type 2 diabetes, which method comprises administering a compound of formula I as described herein to a human being or animal.

A certain embodiment of the invention provides a method for the use in the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease, which method comprises administering a compound of formula I as described herein to a human being or animal.

Furthermore, the invention includes all optical isomers, i.e. diastereoisomers, diastereomeric mixtures, racemic mixtures, all their corresponding enantiomers and/or tautomers as well as their solvates of the compounds of formula I.

The skilled person in the art will recognize that the compounds of formula I can exist in tautomeric forms, e.g. in the following tautomeric form:

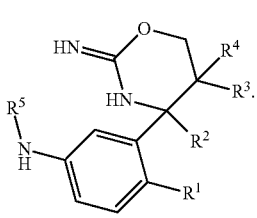

Id

All tautomeric forms are encompassed in the present invention.

The compounds of formula I can contain one or more asymmetric centers and can therefore occur as racemates, racemic mixtures, single enantiomers, diastereomeric mixtures and individual diastereomers. Additional asymmetric centers can be present depending upon the nature of the various substituents on the molecule. Each such asymmetric center will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations can be achieved as known in the art by appropriate modification of the methodology disclosed herein. Their absolute stereochemistry can be determined by the x-ray crystallography of crystalline products or crystalline intermediates which are derivatized, if necessary, with a reagent containing an asymmetric center of known absolute configuration. If desired, racemic mixtures of the compounds can be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. Particular examples of isomers of a compound of formula I is a compound of formula Ia or a compound of formulas Ib, Ia-I, Ia-II, Ib-I or Ib-II, in particular Ia, wherein the residues have the meaning as described in any of the embodiments.

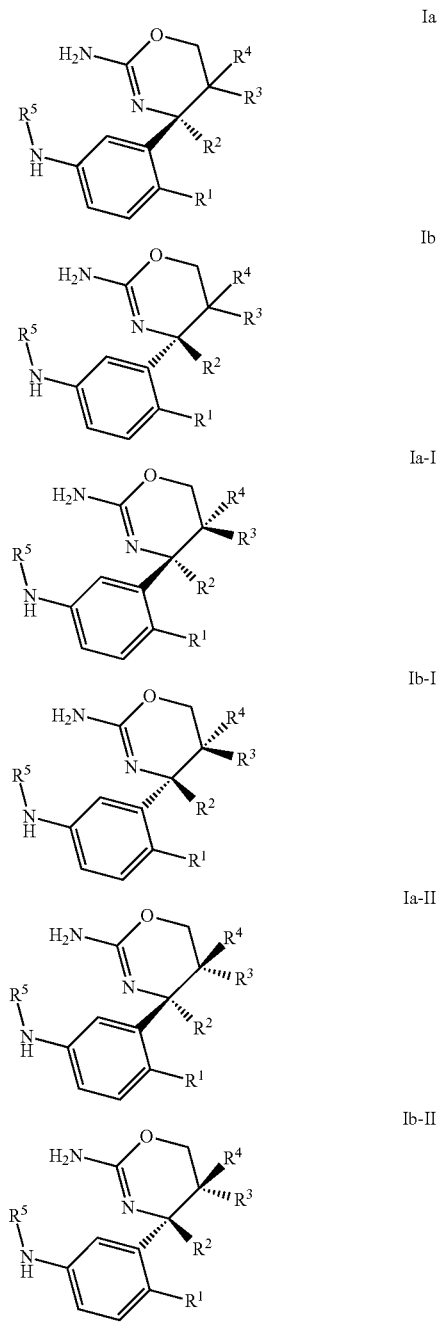

In the embodiments, where optically pure enantiomers are provided, optically pure enantiomer means that the compound contains >90% of the desired isomer by weight, particularly >95% of the desired isomer by weight, or more particularly >99% of the desired isomer by weight, said weight percent based upon the total weight of the isomer(s) of the compound. Chirally pure or chirally enriched compounds can be prepared by chirally selective synthesis or by separation of enantiomers. The separation of enantiomers can be carried out on the final product or alternatively on a suitable intermediate.

The compounds of formula I can be prepared in accordance with the following schemes. The starting material is commercially available or can be prepared in accordance with known methods. Any previously defined residues and variables will continue to have the previously defined meaning unless otherwise indicated.

Sulfinyl imines of formula A2 can be prepared in analogy to T. P. Tang & J. A. Ellman, J. Org. Chem. 1999, 64, 12, by condensation of an aryl ketone A1 and a sulfinamide, e.g. an alkyl sulfinamide, most particularly (R)-(+)-tert-butylsulfinamide, in the presence of a Lewis acid such as e.g. a titanium (IV)alkoxide, more particularly titanium(IV)ethoxide in a solvent such as an ether, e.g. diethyl ether or more particularly tetrahydrofuran.

The conversion of the sulfinyl imine A2 to the sulfinamide ester A3 proceeds stereoselectively by the chiral directing group as described by Tang & Ellman. The sulfinyl imine A2 can be reacted in a Reformatsky reaction with a zinc enolate, activated zinc powder at ambient to elevated temperature, particularly at 23 to 60° C. in a solvent such as an ether, e.g. diethyl ether or more particularly tetrahydrofuran. The zinc enolate is generated from an alkyl acetate or propionate substituted by halogen, e.g. particularly ethyl bromo-fluoro-acetate or ethyl 2-bromo-2-fluoro-propionate. The sulfinyl imine A2 can also be reacted with an alkyl acetate substituted by a halogen-alkoxy group, like e.g. ethyl 2-(2,2,2-trifluoroethoxy)acetate in presence of a strong base such as n-butyl lithium at 0 to −78° C. in an inert solvent such as an ether, e.g. diethyl ether or more particularly tetrahydrofuran.

The alcohol of formula A4 can be prepared by the reduction of an ethylester of formula A3 with an alkali hydride, particularly lithium borohydride or lithium aluminium hydride, in a solvent such as an ether, e.g. diethyl ether or more particularly tetrahydrofuran.

Hydrolysis of the chiral directing group in the sulfinamide alcohol of formula A4 to give the aminoalcohol of formula A5 can be accomplished with a mineral acid, e.g. sulfuric acid or particularly hydrochloric acid, in a solvent such as an ether, e.g. diethyl ether, tetrahydrofuran or more particularly 1,4-dioxane.

The aminooxazine of formula A6 can be prepared by reaction of an aminoalcohol of formula A5 with cyanogen bromide in a solvent such as an alcohol, particularly ethanol.

Scheme A: Synthesis of intermediates of formula I.

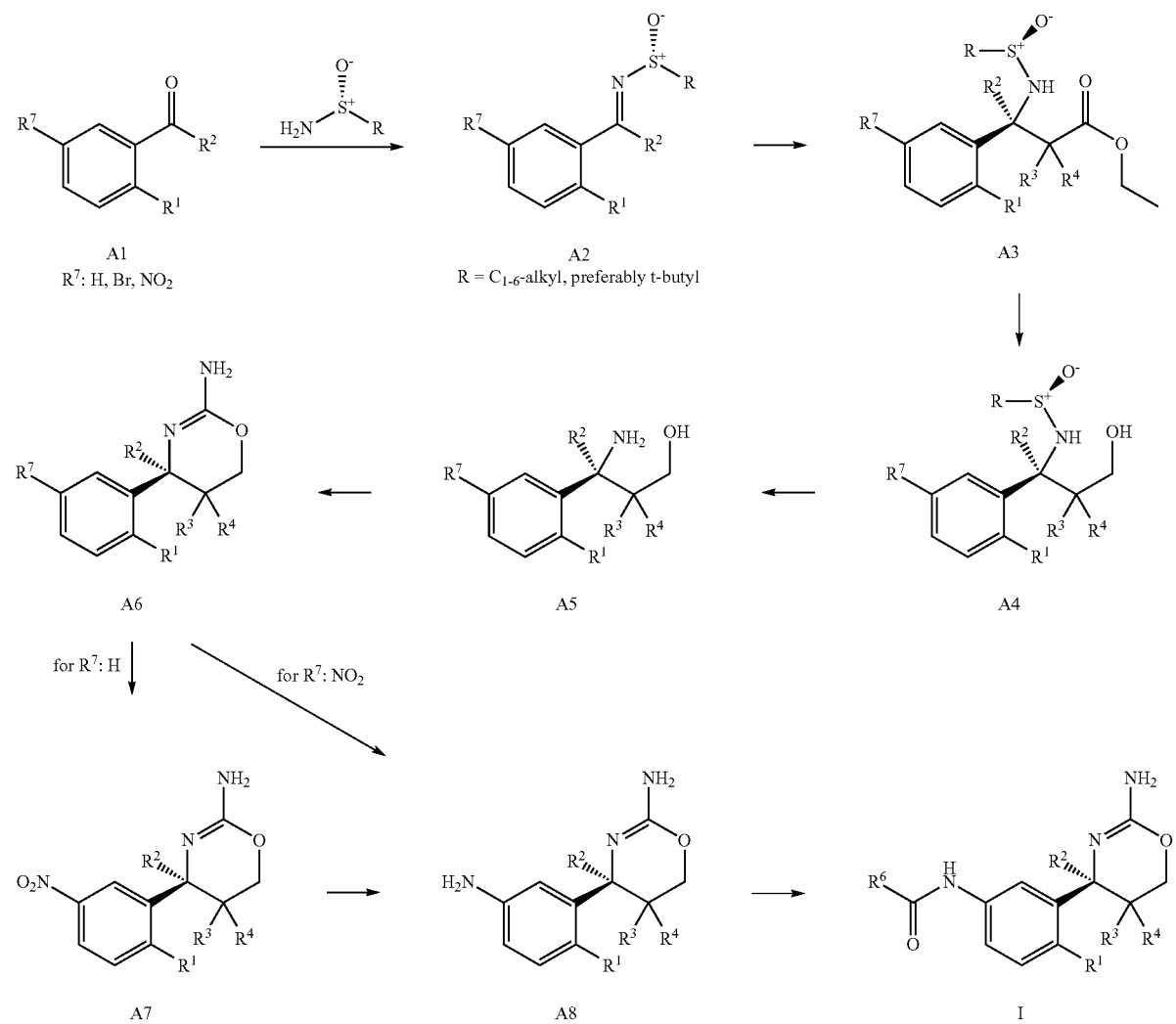

The nitro derivative of formula A7 can be prepared by nitration of the oxazine A6, wherein $R^7$ is hydrogen, following a standard procedure involving neat sulfuric acid and fuming nitric acid without using a solvent.

The reduction of the nitro group in compounds of formula A7 to give anilines of formula A8 can be accomplished by hydrogenation using a catalyst, such as palladium on carbon, in protic solvents, such as alcohols, in particular ethanol or methanol.

Alternatively, the reduction of derivatives of formula A6, wherein $R^7$ is a nitro group, to give anilines of formula A8 can be accomplished by hydrogenation using a catalyst, such as palladium on carbon, in protic solvents, such as alcohols, in particular ethanol or methanol.

Selective reaction of anilines of formula A8 with carboxylic acids of formula $R^6$—COOH to give amides of formula I can be effected with 4-(4,6-dimethoxy[1.3.5]triazin-2-yl)-4-methylmorpholinium chloride (DMTMM) hydrate in a solvent such as methanol.

Scheme B: Alternative synthesis of aniline intermediate A8.

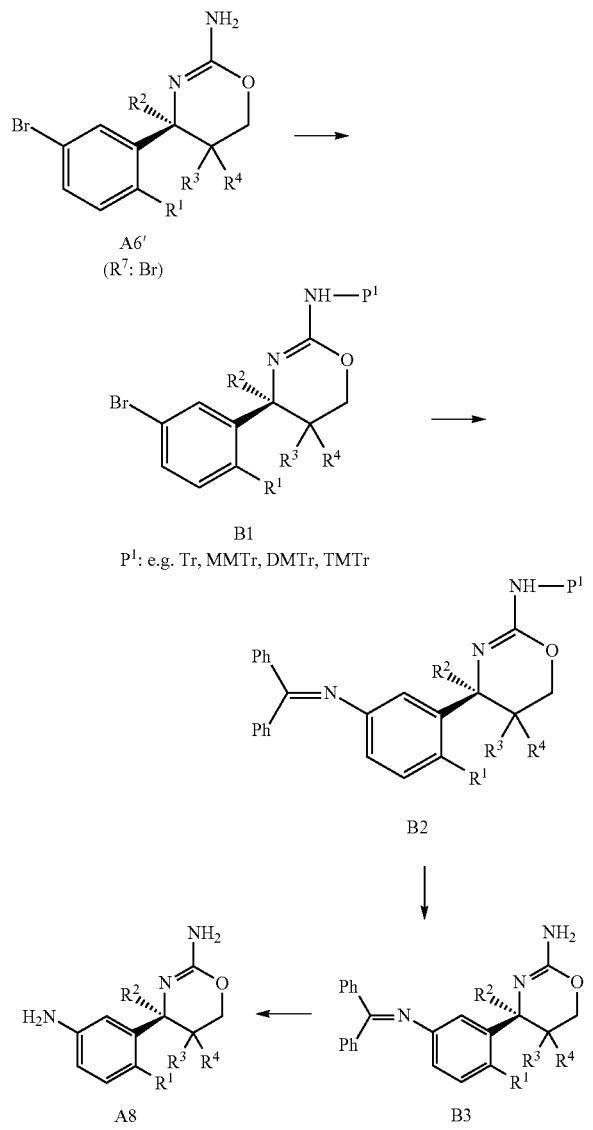

Another typical procedure for the preparation of compounds of formula A8 is illustrated in Scheme B.

Protection of the amino group in compounds of formula A6, wherein $R^7$ is bromine, to produce aryl bromides of formula B1 can be performed with triarylmethyl chlorides, such as triphenylmethyl chloride (Tr-Cl), p-methoxyphenyl-diphenylmethyl chloride (MMTr-Cl), di(p-methoxyphenyl) phenylmethyl chloride (DMTr-Cl) or tri(p-methoxyphenyl) methyl chloride (TMTr-Cl), particularly DMTr-Cl, under basic conditions, e.g. in the presence of an amine, such as triethylamine or diisopropylethylamine, in a chlorinated solvent, such as dichloromethane or chloroform, at temperatures between 0° C. and ambient temperature.

Aryl bromides of formula B1 can be reacted with ammonia equivalents, such as benzophenone imine, in the presence of a suitable transition metal catalyst, such as bis(dibenzylideneacetone)palladium (0) ((dba)$_2$Pd) or tris(dibenzylideneacetone)dipalladium (0) ((dba)$_3$Pd$_2$)), and a suitable ligand, such as rac-2,2'-bis(diphenylphosphino)-1,1'-binaphthyl (rac-BINAP), 2-dicyclohexylphosphino-2',4',6'-triisopropyl-biphenyl (X-PHOS) or 2-di-tert-butylphosphino-2',4',6'-triisopropylbiphenyl (t-Bu X-PHOS), in the presence of a base, such as sodium tert-butoxide, potassium phosphate or cesium carbonate, in a suitable solvent, such as toluene or 1,4-dioxane, under an inert atmosphere, such as nitrogen or argon, at temperatures between 80 and 110° C., to produce compounds of formula B2.

Deprotection of both amino groups in compounds of formula B2 can be achieved by a one-pot procedure by first reacting it with a strong organic acid, such as trifluoroacetic acid, in chlorinated solvents, such as dichloromethane or chloroform, under anhydrous conditions at temperatures between 0° C. and ambient temperature to cleave the $P^1$-group to yield intermediates of formula B3. Then the addition of water to cleave the benzophenone imine and reaction at ambient temperature produces diamines of formula A8.

An alternative procedure for the preparation of compounds of formula I is illustrated in Scheme C.

The protection of the amino group in compounds of formula A7, wherein $R^7$ is a nitro group, to produce compounds of formula C1, can be performed by reaction with di-tert-butyl dicarbonate under basic conditions, e.g. in the presence of an amine, such as triethylamine or diisopropylethylamine, in a solvent, such as tetrahydrofuran, at temperatures between 0° C. and ambient temperature and in presence of 4-dimethylamino-pyridine as a catalyst.

Selective cleavage of one of the tert-butoxy carbonyl groups in compounds of formula C1 can be performed by acid, such as trifluoroacetic acid, to produce compounds of formula C2 together with small amounts of compounds of formula A7.

The reduction of the nitro group in the protected aminooxazines of formula C2 to the protected anilines of formula C3 can be accomplished by hydrogenation using a catalysts such as palladium on carbon in protic solvents, such as alcohols, in particular ethanol or methanol.

Scheme C: Alternative synthesis of compounds of formula I.

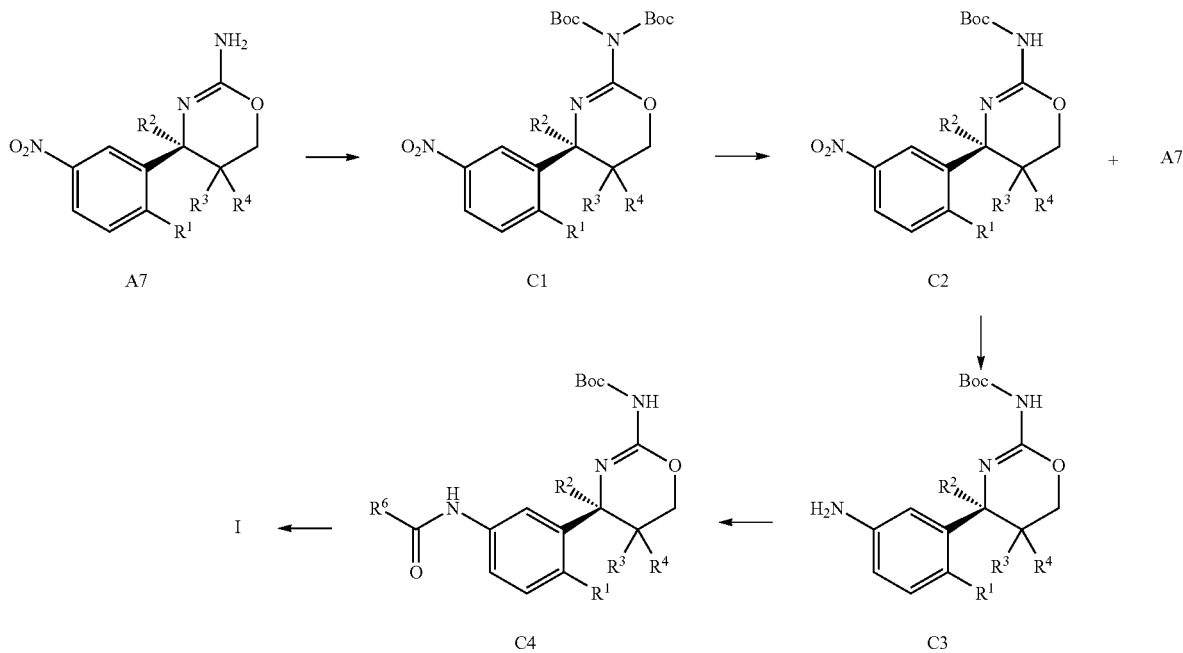

Amide coupling of anilines of formula C3 and carboxylic acids of formula R⁶—COOH to give amides of formula C4 can be effected in a solvent such as methanol with 4-(4,6-dimethoxy[1.3.5]triazin-2-yl)-4-methylmorpholinium chloride hydrate (DMTMM) or other condensating agents, such as O-(benzotriazol-1-yl)-N,N,N',N'-tetramethyluronium.-hexafluorophosphate (HBTU) or O-(7-azabenzotriazol-1-yl)-N,N,N',N'-tetramethyluronium-hexafluorophosphate (HATU), in the presence of an amine, such as triethylamine or diisopropylethylamine, in a solvent, such as acetonitrile or N,N-dimethylformamide, at temperatures between 0° C. and ambient temperature.

The cleavage of the protecting tert-butoxy carbonyl group in compounds of formula C4 to produce compounds of formula I can be effected by acid, such as trifluoroacetic acid, in inert solvents, such as dichloromethane, at temperatures between 0° C. and ambient temperature.

Scheme D: Alternative synthesis of intermediates A6' and B3.

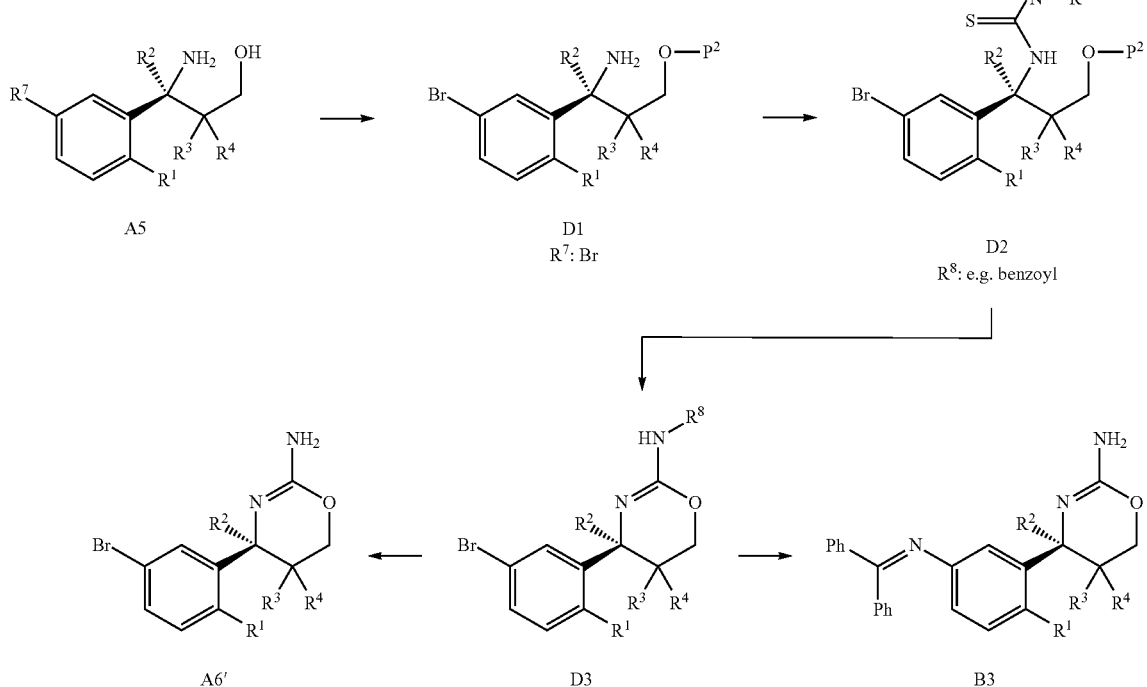

Alternatively, compounds of formula A6' can be obtained as follows: Selective protection of the primary alcohol in compounds of formula A5 can be performed with chloro-silyl derivatives, such as tert-butyl-chlorodimethyl-silane or tert-butyl-chlorodiphenyl-silyane, under basic conditions, e.g. in the presence of an amine, such as triethylamine or diisopropylethylamine, in a chlorinated solvent, such as dichloromethane or chloroform, at temperatures between 0° C. and ambient temperature and in presence of 4-dimethylaminopyridine as a catalyst.

The choice of isothiocyanates for the formation of thioureas of formula D2 depends on the reactivity of the amino function. Preferably benzoyl isocyanate in inert solvents, e.g. acetone, at temperatures between 0 and 100° C. was used to prepare acylated thioureas of formula D2.

The cyclization to the N-acyl oxazine of formula D3 under the concomitant loss of the silyl protecting group can be achieved by treatment of the acylated thiourea of formula D2 with alkyl oxonium salts, e.g. trimethyloxonium tetrafluoroborate or triethyloxonium tetrafluoroborate in an inert solvent, e.g. in a chlorinated solvent, such as dichloromethane or chloroform, at temperatures between 0° C. and ambient temperature.

The cleavage of the acyl residue in compounds of formula D3 under basic conditions, e.g. with alkali carbonates, in polar solvents such as alcohols, e.g. methanol or ethanol, yields compounds of formula A6'.

Alternatively, imines of formula B3 (cf. scheme B) can be obtained by reaction of aryl bromides of formula D3 with ammonia equivalents, such as benzophenone imine, in the presence of a suitable transition metal catalyst, such as bis(dibenzylideneacetone)palladium (0) ((dba)$_2$Pd) or tris(dibenzylideneacetone)dipalladium (0) ((dba)$_3$Pd$_2$)), and a suitable ligand, such as rac-2,2'-bis(diphenylphosphino)-1,1'-binaphthyl (rac-BINAP), 2-dicyclohexylphosphino-2',4',6'-triisopropylbiphenyl (X-PHOS) or 2-di-tert-butylphosphino-2',4',6'-triisopropylbiphenyl (t-Bu X-PHOS), in the presence of a base, such as sodium tert-butoxide, potassium phosphate or cesium carbonate, in a suitable solvent, such as toluene or 1,4-dioxane, under an inert atmosphere, such as nitrogen or argon, at temperatures between 80 and 110° C.

The corresponding pharmaceutically acceptable salts with acids can be obtained by standard methods known to the person skilled in the art, e.g. by dissolving the compound of formula I in a suitable solvent such as e.g. dioxane or tetrahydrofuran (THF) and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. M(OH)$_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation. Particular salts are hydrochloride, formate and trifluoroacetate.

Insofar as their preparation is not described in the examples, the compounds of formula I as well as all intermediate products can be prepared according to analogous methods or according to the methods set forth herein. Starting materials are commercially available, known in the art or can be prepared by methods known in the art or in analogy thereto.

It will be appreciated that the compounds of formula I in this invention can be derivatised at functional groups to provide derivatives which are capable of conversion back to the parent compound in vivo.

Pharmacological Tests

The compounds of formula I and their pharmaceutically acceptable salts possess valuable pharmacological properties. Compounds of the present invention are associated with inhibition of BACE1 and/or BACE2 activity. The compounds were investigated in accordance with the test given hereinafter.

Cellular Aβ-Lowering Assay:

Human HEK293 cells which are stably transfected with a vector expressing a cDNA of the human APP wt gene (APP695) were used to assess the potency of the compounds in a cellular assay. The cells were seeded in 96-well microtiter plates in cell culture medium (Iscove, plus 10% (v/v) fetal bovine serum, glutamine, penicillin/streptomycin) to about 80% confluence and the compounds were added at a 10× concentration in 1/10 volume of medium without FCS containing 8% DMSO (final concentration of DMSO was kept at 0.8% v/v). After 18-20 hrs incubation at 37° C. and 5% CO$_2$ in a humidified incubator the culture supernatant was harvested for the determination of Aβ40 concentrations. 96 well ELISA plates (e.g., Nunc MaxiSorb) were coated with monoclonal antibody which specifically recognize the C-terminal end of Aβ40 (Brockhaus et al., NeuroReport 9, 1481-1486; 1998). After blocking of non-specific binding sites with e.g. 1% BSA and washing, the culture supernatants were added in suitable dilutions together with a horseradish peroxidase-coupled Aβ detection antibody (e.g., antibody 4G8, Senetek, Maryland Heights, Mo.) and incubated for 5 to 7 hrs. Subsequently the wells of the microtiter plate were washed extensively with Tris-buffered saline containing 0.05% Tween 20 and the assay was developed with tetramethylbenzidine/ H$_2$O$_2$ in citric acid buffer. After stopping the reaction with one volume 1 N H$_2$SO$_4$ the reaction was measured in an ELISA reader at 450 nm wavelength. The concentrations of Aβ in the culture supernatants were calculated from a standard curve obtained with known amounts of pure Aβ peptide.

Assay for BACE Inhibition by Measuring Cellular TMEM27 Cleavage:

The assay uses the principle of inhibition of human TMEM27 cleavage by endogenous cellular BACE2 in the Ins1e rat cell line and shedding from the cell surface into the culture medium, followed by detection in an ELISA assay. Inhibition of BACE2 prevents the cleavage and shedding in a dose-dependent manner.

The stable cell line "INS-TMEM27" represents an INS1e-derived cell line with inducible expression (using the TetOn system) of full-length hTMEM27 in a doxycycline-dependent manner. The cells are cultured throughout the experiment in RPMI1640+Glutamax (Invitrogen) Penicillin/Streptomycin, 10% Fetal bovine serum, 100 mM pyruvate, 5 mM beta-mercaptoethanol, 100 micrograms/ml G418 and 100 microgram/ml hygromycin and are grown inadherent culture at 37° C. in a standard CO$_2$ cell culture incubator.

INS-TMEM27 cells are seeded in 96-well plates. After 2 days in culture, BACE2 inhibitor is added in a range of concentrations as required by the assay and after a further two hours, doxycycline is added to a final concentration of 500 ng/ml. The cells are incubated for a further 46 hours and the supernatant harvested for detection of shed TMEM27.

An ELISA assay (using a pair of mouse anti-human-TMEM27 antibodies, raised against the extracellular domain of TMEM27) is used for detection of TMEM27 in the culture medium. An EC$_{50}$ for BACE2 inhibition is calculated using the ELISA readout for each inhibitor concentration with standard curve-fitting software such as XLFit for the Excel spreadsheet program.

TABLE 1

| | | BACE1 | BACE2 |
| | | IC$_{50}$ | IC$_{50}$ |
| Exam. | Structure | [μM] | [μM] |
|---|---|---|---|
| 1 | 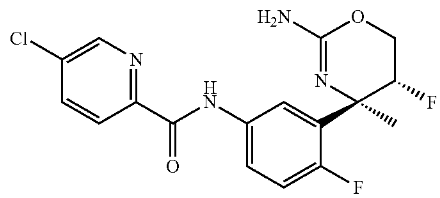 [SMILES: C[C@]1(c2cc(NC(=O)c3ccc(Cl)cn3)ccc2F)N=C(N)OC[C@@H]1F] | 0.0004 | 0.001 |
| 2 | 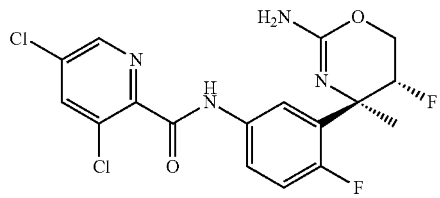 [SMILES: C[C@]1(c2cc(NC(=O)c3ncc(Cl)cc3Cl)ccc2F)N=C(N)OC[C@@H]1F] | 0.0006 | 0.008 |
| 3 | 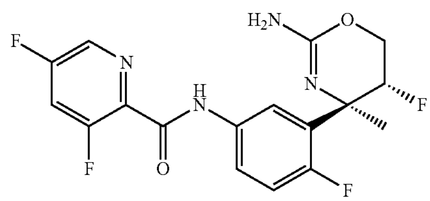 [SMILES: C[C@]1(c2cc(NC(=O)c3ncc(F)cc3F)ccc2F)N=C(N)OC[C@@H]1F] | 0.001 | 0.007 |
| 4 | 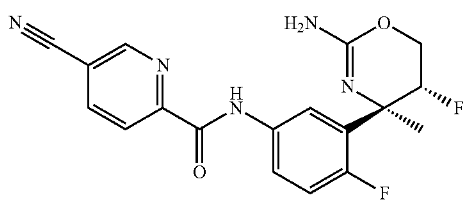 [SMILES: C[C@]1(c2cc(NC(=O)c3ccc(C#N)cn3)ccc2F)N=C(N)OC[C@@H]1F] | 0.001 | 0.021 |
| 5 | 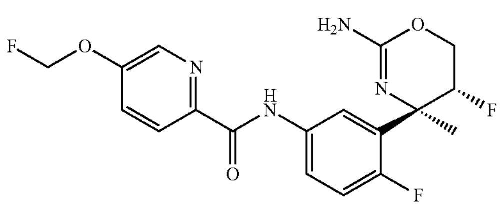 [SMILES: C[C@]1(c2cc(NC(=O)c3ccc(OCF)cn3)ccc2F)N=C(N)OC[C@@H]1F] | 0.001 | 0.106 |
| 6 | 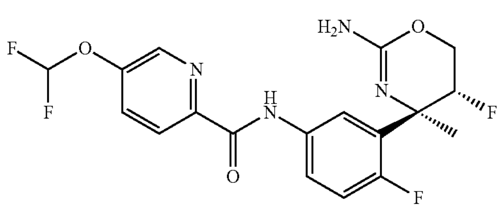 | 0.002 | — |
| 7 | 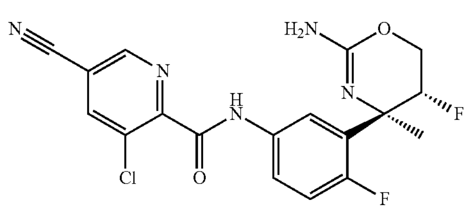 [SMILES: C[C@]1(c2cc(NC(=O)c3ncc(C#N)cc3Cl)ccc2F)N=C(N)OC[C@@H]1F] | 0.002 | 0.010 |

TABLE 1-continued

IC50 values of selected examples

| Exam. | Structure | BACE1 IC50 [μM] | BACE2 IC50 [μM] |
|---|---|---|---|
| 8 | 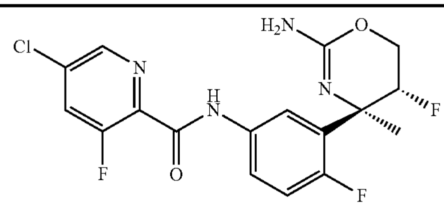 | 0.002 | 0.006 |
| 9 | 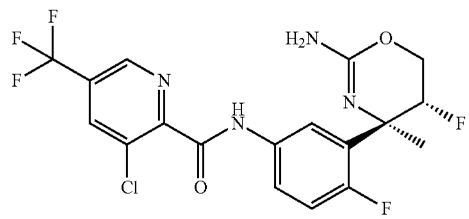 [SMILES: C[C@]1(c2cc(NC(=O)c3ncc(C(F)(F)F)cc3Cl)ccc2F)N=C(N)OC[C@@H]1F] | 0.002 | 0.124 |
| 10 | 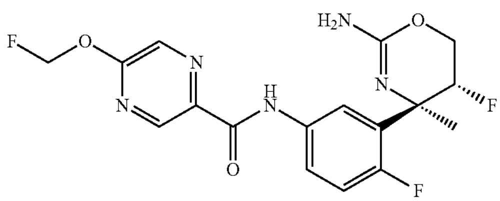 [SMILES: C[C@]1(c2cc(NC(=O)c3cnc(OCF)cn3)ccc2F)N=C(N)OC[C@@H]1F] | 0.024 | — |
| 11 | 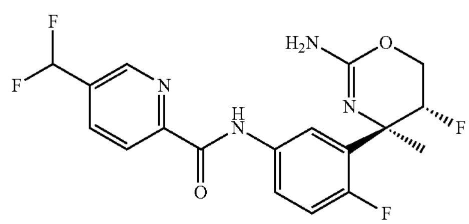 [SMILES: C[C@]1(c2cc(NC(=O)c3ccc(C(F)F)cn3)ccc2F)N=C(N)OC[C@@H]1F] | 0.003 | 0.001 |
| 12 | 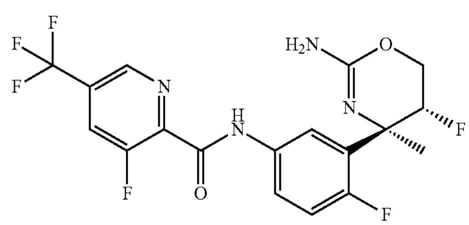 | 0.004 | — |
| 13 | 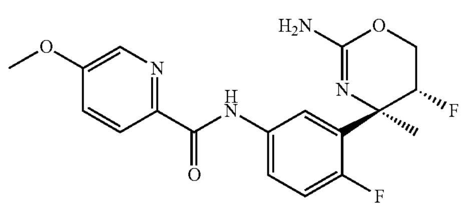 [SMILES: COc1ccc(C(=O)Nc2ccc(F)c([C@@]3(C)N=C(N)OC[C@@H]3F)c2)nc1] | 0.004 | 0.065 |
| 14 | 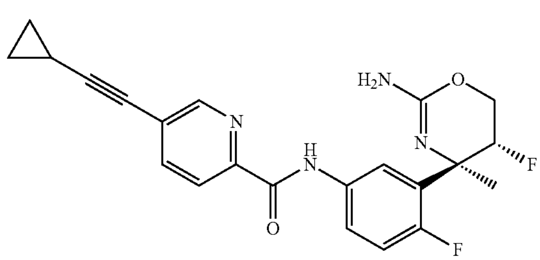 [SMILES: C[C@]1(c2cc(NC(=O)c3ccc(C#CC4CC4)cn3)ccc2F)N=C(N)OC[C@@H]1F] | 0.004 | 0.009 |

TABLE 1-continued

IC₅₀ values of selected examples

| Exam. | Structure | BACE1 IC$_{50}$ [μM] | BACE2 IC$_{50}$ [μM] |
|---|---|---|---|
| 15 | 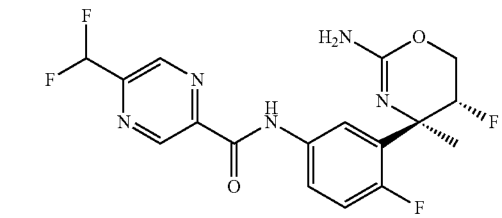 [SMILES: C[C@]1(c2cc(NC(=O)c3cnc(C(F)F)cn3)ccc2F)N=C(N)OC[C@@H]1F] | 0.005 | 0.023 |
| 16 | 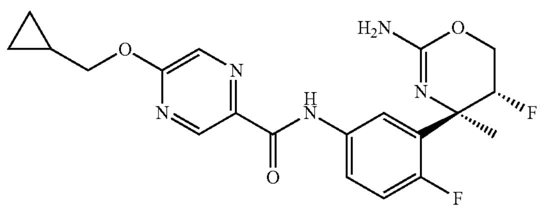 [SMILES: C[C@]1(c2cc(NC(=O)c3cnc(OCC4CC4)cn3)ccc2F)N=C(N)OC[C@@H]1F] | 0.005 | 0.590 |
| 17 | 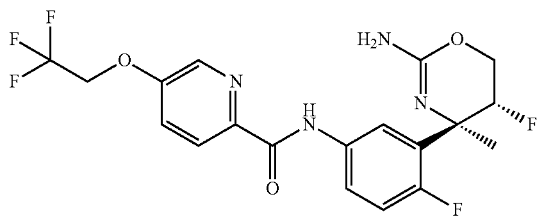 [SMILES: C[C@]1(c2cc(NC(=O)c3ccc(OCC(F)(F)F)cn3)ccc2F)N=C(N)OC[C@@H]1F] | 0.008 | 2.300 |
| 18 | 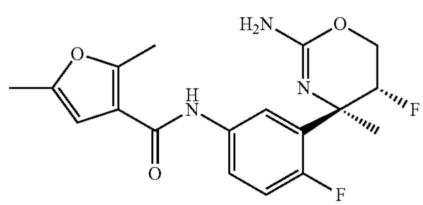 [SMILES: Cc1cc(C(=O)Nc2ccc(F)c([C@@]3(C)N=C(N)OC[C@@H]3F)c2)c(C)o1] | 0.008 | 0.020 |
| 19 | 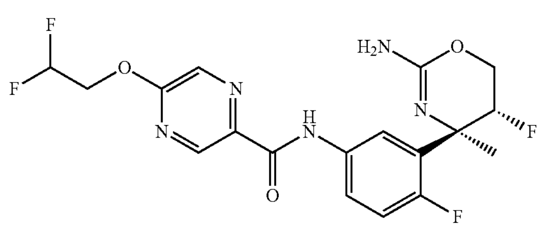 [SMILES: C[C@]1(c2cc(NC(=O)c3cnc(OCC(F)F)cn3)ccc2F)N=C(N)OC[C@@H]1F] | 0.008 | — |
| 20 | 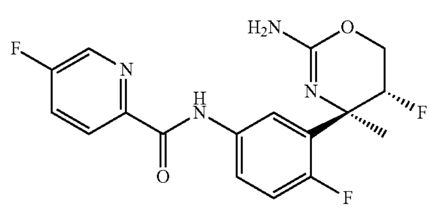 [SMILES: C[C@]1(c2cc(NC(=O)c3ccc(F)cn3)ccc2F)N=C(N)OC[C@@H]1F] | 0.010 | 0.007 |
| 21 | 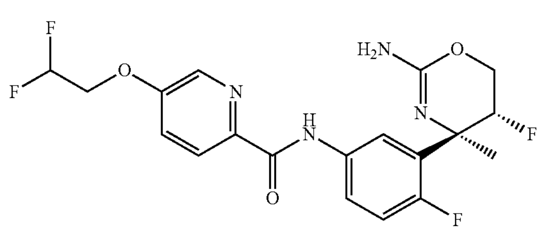 [SMILES: C[C@]1(c2cc(NC(=O)c3ccc(OCC(F)F)cn3)ccc2F)N=C(N)OC[C@@H]1F] | 0.013 | — |

TABLE 1-continued

IC$_{50}$ values of selected examples

| Exam. | Structure | BACE1 IC$_{50}$ [μM] | BACE2 IC$_{50}$ [μM] |
|---|---|---|---|
| 22 | (5-cyclopropyl-pyridine-2-carboxamide derivative) | 0.014 | 0.124 |
| 23 | (5-(cyclopropylmethoxy)pyridine-2-carboxamide derivative) | 0.015 | — |
| 24 | (5-(2,2,3,3-tetrafluoropropoxy)pyridine-2-carboxamide derivative) | 0.017 | — |
| 25 | (5-(2,2,3,3,3-pentafluoropropoxy)pyridine-2-carboxamide derivative) | 0.052 | — |
| 26 | (2-chlorothiazole-5-carboxamide derivative) | 0.081 | 1.405 |
| 27 | (1-methyl-5-(trifluoromethyl)pyrazole-3-carboxamide derivative) | 0.090 | 0.709 |
| 28 | (4-chloro-1H-pyrazole-3-carboxamide derivative) | 0.130 | 0.035 |

TABLE 1-continued

IC$_{50}$ values of selected examples

| Exam. | Structure | BACE1 IC$_{50}$ [μM] | BACE2 IC$_{50}$ [μM] |
|---|---|---|---|
| 29 | 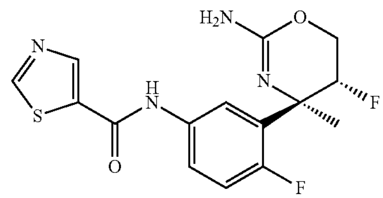 [SMILES: C[C@]1(c2cc(NC(=O)c3cncs3)ccc2F)N=C(N)OC[C@@H]1F] | 0.250 | — |
| 30 | 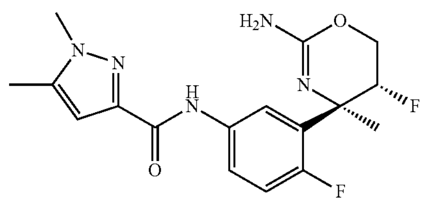 [SMILES: Cc1cc(C(=O)Nc2ccc(F)c([C@@]3(C)N=C(N)OC[C@@H]3F)c2)nn1C] | 0.760 | — |
| 31 | 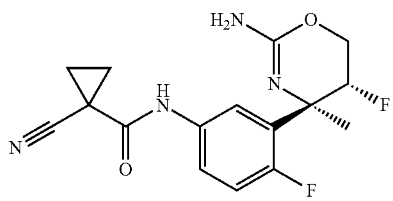 [SMILES: C[C@]1(c2cc(NC(=O)C3(C#N)CC3)ccc2F)N=C(N)OC[C@@H]1F] | 0.075 | — |
| 32 | 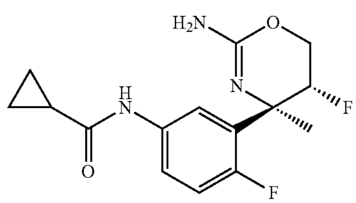 [SMILES: C[C@]1(c2cc(NC(=O)C3CC3)ccc2F)N=C(N)OC[C@@H]1F] | 0.730 | — |
| 33 | 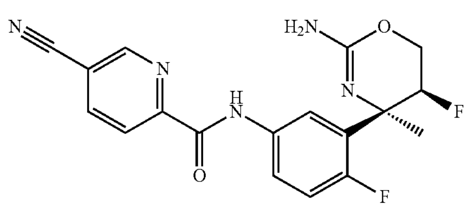 [SMILES: C[C@]1(c2cc(NC(=O)c3ccc(C#N)cn3)ccc2F)N=C(N)OC[C@H]1F] | 0.027 | 1.174 |
| 34 | 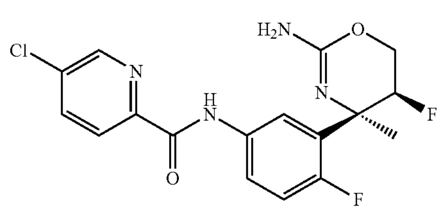 [SMILES: C[C@]1(c2cc(NC(=O)c3ccc(Cl)cn3)ccc2F)N=C(N)OC[C@H]1F] | 0.042 | — |
| 35 | 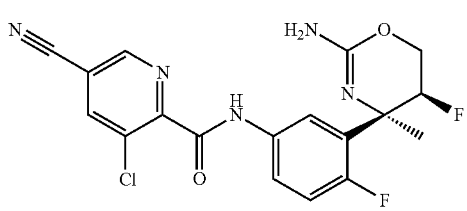 [SMILES: C[C@]1(c2cc(NC(=O)c3ncc(C#N)cc3Cl)ccc2F)N=C(N)OC[C@H]1F] | 0.082 | 0.511 |

TABLE 1-continued

IC$_{50}$ values of selected examples

| Exam. | Structure | BACE1 IC$_{50}$ [μM] | BACE2 IC$_{50}$ [μM] |
|---|---|---|---|
| 36 | 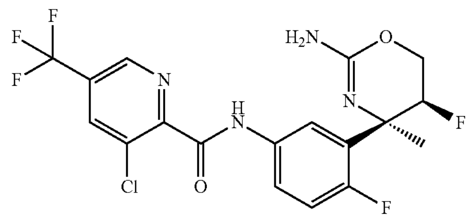 [SMILES: C[C@]1(c2cc(NC(=O)c3ncc(C(F)(F)F)cc3Cl)ccc2F)N=C(N)OC[C@H]1F] | 0.140 | 4.029 |
| 37 | 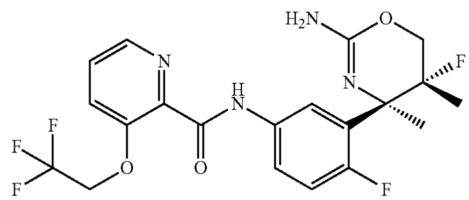 [SMILES: C[C@]1(F)COC(N)=N[C@]1(C)c1cc(NC(=O)c2ncccc2OCC(F)(F)F)ccc1F] | 0.022 | 0.226 |
| 38 | 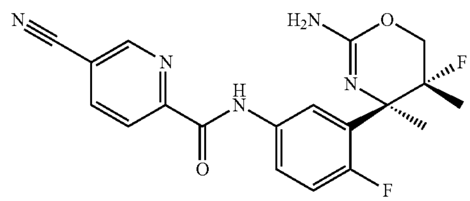 [SMILES: C[C@]1(F)COC(N)=N[C@]1(C)c1cc(NC(=O)c2ccc(C#N)cn2)ccc1F] | 0.0004 | 0.023 |
| 39 | 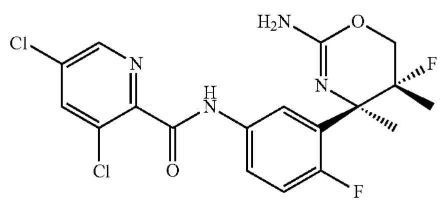 [SMILES: C[C@]1(F)COC(N)=N[C@]1(C)c1cc(NC(=O)c2ncc(Cl)cc2Cl)ccc1F] | 0.002 | 0.004 |
| 40 | 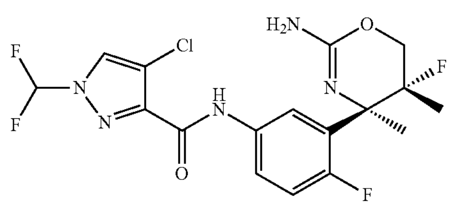 [SMILES: C[C@]1(F)COC(N)=N[C@]1(C)c1cc(NC(=O)c2nn(C(F)F)cc2Cl)ccc1F] | 0.002 | 0.031 |
| 41 | 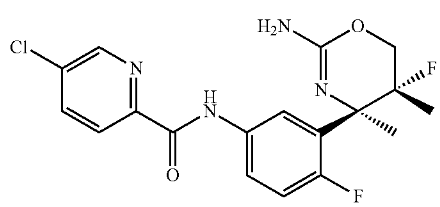 [SMILES: C[C@]1(F)COC(N)=N[C@]1(C)c1cc(NC(=O)c2ccc(Cl)cn2)ccc1F] | 0.003 | 0.006 |
| 42 | 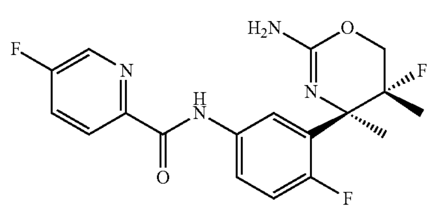 [SMILES: C[C@]1(F)COC(N)=N[C@]1(C)c1cc(NC(=O)c2ccc(F)cn2)ccc1F] | 0.011 | 0.074 |

TABLE 1-continued
IC₅₀ values of selected examples
| Exam. | Structure | BACE1 IC₅₀ [μM] | BACE2 IC₅₀ [μM] |
|---|---|---|---|
| 43 | 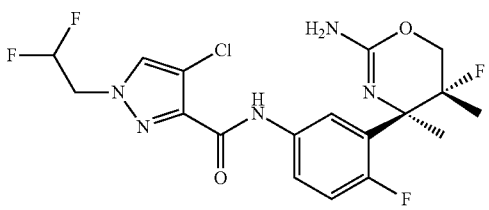 [SMILES: C[C@]1(F)COC(N)=N[C@]1(C)c1cc(NC(=O)c2nn(CC(F)F)cc2Cl)ccc1F] | 0.183 | 0.110 |
| 44 | 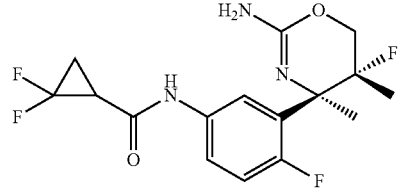 [SMILES: C[C@]1(F)COC(N)=N[C@]1(C)c1cc(NC(=O)C2CC2(F)F)ccc1F] | 0.032 | 0.140 |
| 45 | 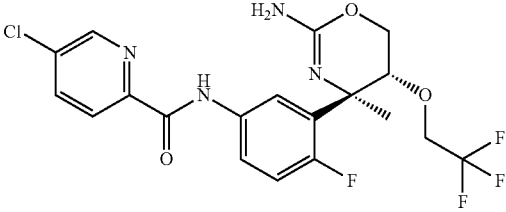 [SMILES: C[C@]1(c2cc(NC(=O)c3ccc(Cl)cn3)ccc2F)N=C(N)OC[C@@H]1OCC(F)(F)F] | 0.001 | 0.061 |
| 46 | 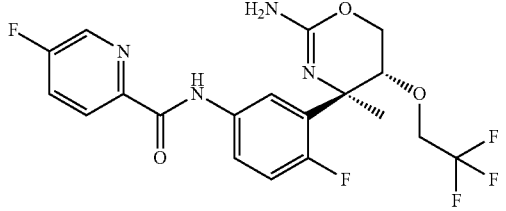 [SMILES: C[C@]1(c2cc(NC(=O)c3ccc(F)cn3)ccc2F)N=C(N)OC[C@@H]1OCC(F)(F)F] | 0.002 | 0.065 |
| 47 | 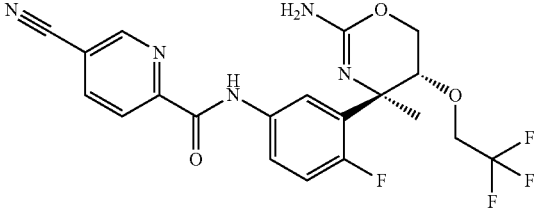 [SMILES: C[C@]1(c2cc(NC(=O)c3ccc(C#N)cn3)ccc2F)N=C(N)OC[C@@H]1OCC(F)(F)F] | 0.001 | 0.268 |
| 48 | 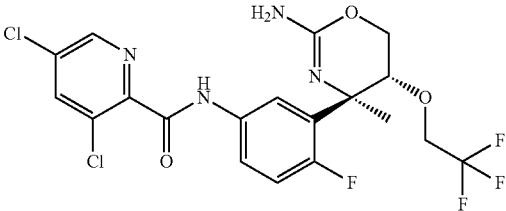 [SMILES: C[C@]1(c2cc(NC(=O)c3ncc(Cl)cc3Cl)ccc2F)N=C(N)OC[C@@H]1OCC(F)(F)F] | 0.003 | 0.067 |

TABLE 1-continued

IC₅₀ values of selected examples

| Exam. | Structure | BACE1 IC$_{50}$ [μM] | BACE2 IC$_{50}$ [μM] |
|---|---|---|---|
| 49 | 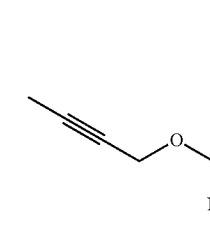 | 0.021 | — |
| 50 | 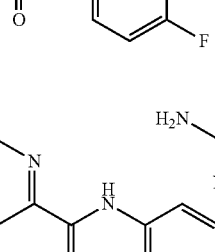 | 0.0001 | — |
| 51 | 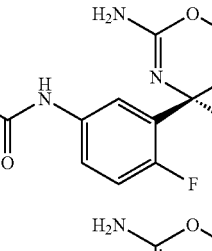 | 0.025 | — |
| 52 | 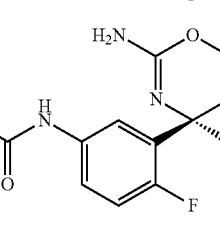 | 0.039 | — |
| 53 | 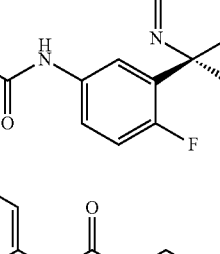 | — | — |

Pharmaceutical Compositions

The compounds of formula I and the pharmaceutically acceptable salts can be used as therapeutically active substances, e.g. in the form of pharmaceutical preparations. The pharmaceutical preparations can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formula I and the pharmaceutically acceptable salts thereof can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also provided by the present invention, as is a process for their production, which comprises bringing one or more compounds of formula I and/or pharmaceutically acceptable salts thereof and, if desired, one or more other therapeutically valuable substances into a galenical administration form together with one or more therapeutically inert carriers.

The dosage can vary within wide limits and will, of course, have to be adjusted to the individual requirements in each particular case. In the case of oral administration the dosage for adults can vary from about 0.01 mg to about 1000 mg per day of a compound of formula I or of the corresponding amount of a pharmaceutically acceptable salt thereof. The daily dosage can be administered as single dose or in divided doses and, in addition, the upper limit can also be exceeded when this is found to be indicated.

The following examples illustrate the present invention without limiting it, but serve merely as representative thereof. The pharmaceutical preparations conveniently contain about 1-500 mg, particularly 1-100 mg, of a compound of formula I. Examples of compositions according to the invention are:

Example A

Tablets of the following composition are manufactured in the usual manner:

TABLE 2 possible tablet composition

| ingredient | mg/tablet | | | |
|---|---|---|---|---|
| | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Example B-1

Capsules of the following composition are manufactured:

TABLE 3 possible capsule ingredient composition

| ingredient | mg/capsule | | | |
|---|---|---|---|---|
| | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure
1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Example B-2

Soft Gelatin Capsules of the following composition are manufactured:

TABLE 4 possible soft gelatin capsule ingredient composition

| ingredient | mg/capsule |
|---|---|
| Compound of formula I | 5 |
| Yellow wax | 8 |
| Hydrogenated Soya bean oil | 8 |
| Partially hydrogenated plant oils | 34 |
| Soya bean oil | 110 |
| Total | 165 |

TABLE 5 possible soft gelatin capsule composition

| ingredient | mg/capsule |
|---|---|
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure
The compound of formula I is dissolved in a warm melting of the other ingredients and the mixture is filled into soft gelatin capsules of appropriate size. The filled soft gelatin capsules are treated according to the usual procedures.

Example C

Suppositories of the following composition are manufactured:

TABLE 6 possible suppository composition

| ingredient | mg/supp. |
|---|---|
| Compound of formula I | 15 |
| Suppository mass | 1285 |
| Total | 1300 |

Manufacturing Procedure
The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool; the suppositories are then removed from the moulds and packed individually in wax paper or metal foil.

Example D

Injection solutions of the following composition are manufactured:

TABLE 7

| possible injection solution composition | |
|---|---|
| ingredient | mg/injection solution. |
| Compound of formula I | 3 |
| Polyethylene Glycol 400 | 150 |
| acetic acid | q.s. ad pH 5.0 |
| water for injection solutions | ad 1.0 ml |

Manufacturing Procedure

The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example E

Sachets of the following composition are manufactured:

TABLE 8

| possible sachet composition | |
|---|---|
| ingredient | mg/sachet |
| Compound of formula I | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

The compound of formula I is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

EXPERIMENTAL PART

The following examples are provided for illustration of the invention. They should not be considered as limiting the scope of the invention, but merely as being representative thereof.

Synthesis of the Intermediate Sulfinyl Imine A2.1 ($R^7$=H)

A solution of 1-(2-fluorophenyl)ethanone (20 g, 145 mmol) in tetrahydrofuran (250 ml) was treated under an inert atmosphere at room temperature with (R)-(+)-tert-butylsulfinamide (21.1 g, 174 mmol) followed by the addition of titanium(IV)ethoxide (66.1 g, 290 mmol). The solution was stirred at 50° C. for 15 hours. For the workup, the dark brown solution was cooled to room temperature, then poured into a saturated solution of ammonium chloride. After addition of ethyl acetate, the mixture was stirred vigorously for 15 minutes. After separation of the layers, the aqueous phase was extracted twice with ethyl acetate. The combined organic layers were washed twice with water, dried over sodium sulphate and evaporated at reduced pressure. Purification of the crude product by chromatography on silica gel using a 4:1-mixture of cyclohexane and ethyl acetate yielded the (R)-E-N(1-(2-fluorophenyl)ethylidene)-2-methylpropane-sulfinamide (25.9 g, 74% of theory) as a brown oil. MS (ISP): m/z=242.3 [M+H]$^+$.

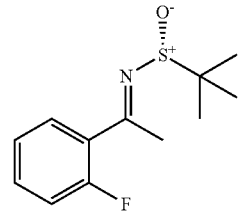 [SMILES: C/C(=N\[S@+]([O-])C(C)(C)C)c1ccccc1F]

Intermediate A2.2

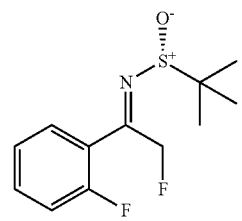 [SMILES: CC(C)(C)[S@@+]([O-])/N=C(\CF)c1ccccc1F]

In a manner analogous to that described for the preparation of sulfinyl imine A2.1 the reaction of 2-fluoro-1-(2-fluorophenyl)-ethanone with (R)-tert-butylsulfinamide yielded the (R)-2-methyl-propane-2-sulfinic acid [2-fluoro-1-(2-fluorophenyl)-eth-(Z)-ylidene]-amide (52% of theory) as an orange oil. MS (ISP): m/z=260.2 [M+H]$^+$.

The 2-fluoro-1-(2-fluoro-phenyl)-ethanone was obtained as follows:

A solution of 1-(2-fluorophenyl)-2-hydroxyethanone [CAS 218771-68-7; WO9857925, ex. 16] (2.77 g, 18.0 mmol) in dichloromethane (42 ml) was treated consecutively at 0° C. with triethylamine (6.36 g, 62.8 mmol), triethylamine trihydrofluoride (3.05 g, 18.0 mmol) and nonafluoro-n-butanesulfonylfluoride (8.48 g, 26.9 mmol). The tube was sealed and the reaction mixture stirred overnight at room temperature. For the workup, the dark red solution was poured on a saturated solution of sodium hydrogencarbonate and ice, then extracted with dichloromethane. The organic layer was separated, dried over sodium sulphate and evaporated. The crude material was purified by flash chromatography on silica gel (Telos Flash Silica) using dichloromethane as the eluent to give the 2-fluoro-1-(2-fluoro-phenyl)-ethanone (1.23 g, 61% of theory) as a yellow semisolid.

Intermediate A2.3

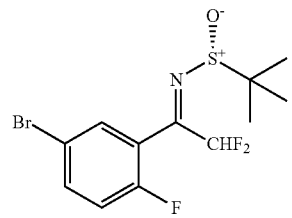 [SMILES: CC(C)(C)[S@@+]([O-])/N=C(/c1cc(Br)ccc1F)C(F)F]

In a manner analogous to that described for the preparation of sulfinyl imine A2.1 the reaction of 1-(5-bromo-2-fluoro-phenyl)-2,2-difluoro-ethanone (CAS 1262858-97-8; WO2011009943) with (R)-tert-butylsulfinamide yielded the (R)-2-methyl-propane-2-sulfinic acid [1-(5-bromo-2-fluoro-phenyl)-2,2-difluoro-eth-(E)-ylidene]-amide (77% of theory) as a yellow oil. MS (ISP): m/z=356.1 [M+H]⁺ and 358.0 [M+2+H]⁺.

Syntheses of the Intermediate Sulfinamide Esters A3
General Procedure (Via Reformatsky Reaction)

In a dry apparatus under an inert atmosphere a suspension of freshly activated zinc powder (1.63 g, 24.9 mmol) in dry tetrahydrofuran (70 ml) was heated to reflux. A solution of the sulfinyl imine A2 (24.9 mmol) and the bromo-acetate (24.9 mmol) in dry tetrahydrofuran (15 ml) was added dropwise over a period of 15 minutes and the suspension was heated to reflux for 5 hours. For the workup, the cooled mixture was partitioned between an aqueous saturated solution of ammonium chloride and ethyl acetate. The organic layer was dried and evaporated at reduced pressure. The crude material was purified by flash chromatography on silica gel using mixtures of heptane and ethyl acetate as the eluent to give the sulfinamide ester A3.

Intermediates A3.1 and A3.2

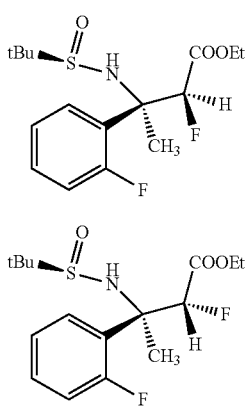

Starting from (R)-2-methyl-propane-2-sulfinic acid [1-(2-fluorophenyl)-(E)-ethylidene]-amide (intermediate A2.1) and ethyl 2-bromo-2-fluoroacetate, the faster eluting minor isomer (2S,3R)-2-fluoro-3-(2-fluoro-phenyl)-3-((R)-2-methyl-propane-2-sulfinylamino)-butyric acid ethyl ester (intermediate A3.1) was obtained as a dark brown oil. MS (ISP): m/z=348.2 [M+H]⁺.

The second fraction contained the slower eluting major isomer (2R,3R)-2-fluoro-3-(2-fluoro-phenyl)-3-((R)-2-methyl-propane-2-sulfinylamino)-butyric acid ethyl ester (intermediate A3.2) as a brown oil. MS (ISP): m/z=348.2 [M+H]⁺.

Syntheses of the Intermediate Sulfinamide Esters A3.3 and A3.4

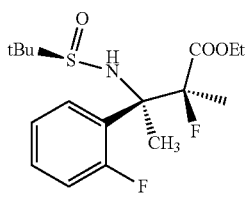

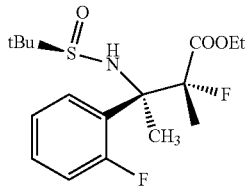

In a dry apparatus under an inert atmosphere a solution of diisopropylamine (3.35 g, 101 mmol) in tetrahydrofuran (25 ml) was treated with n-butyl lithium (1.6M in hexane, 20.7 ml). The solution was stirred at −7° C. for 40 minutes. Thereafter, the solution was cooled to −75° C. and a solution of ethyl 2-fluoropropanoate (3.98 g, 33.2 mmol) in tetrahydrofuran (5 ml) was added dropwise. After 40 minutes a solution of chlorotitanium triisopropoxide (8.64 g, 33.2 mmol) in tetrahydrofuran (15 ml) was slowly added dropwise. After 40 minutes at −72° C. to the orange colored solution was added dropwise a solution of (R)-2-methyl-propane-2-sulfinic acid [1-(2-fluorophenyl)-(E)-ethylidene]-amide (intermediate A2.1) (4.0 g, 16.6 mmol) in tetrahydrofuran (5 ml). Stirring was continued at −72° C. for 4 hours, then the reaction mixture was kept at −20° C. for 17 hours. For the workup, the reaction mixture was quenched with an aqueous solution of ammonium chloride (13%, 100 ml). The precipitate formed was diluted with water and the resulting mixture extracted three times with ethyl acetate. The organic layers were washed with brine, then combined, dried and evaporated at reduced pressure. Purification of the crude product by chromatography on silica gel using a 5:2-mixture auf heptane and ethyl acetate as the eluent yielded a 1:2-mixture of the (2S, 3R)-2-fluoro-3-(2-fluoro-phenyl)-2-methyl-3-((R)-2-methyl-propane-2-sulfinylamino)-butyric acid ethyl ester (A3.3) and (2R,3R)-2-Fluoro-3-(2-fluoro-phenyl)-2-methyl-3-((R)-2-methyl-propane-2-sulfinylamino)-butyric acid ethyl ester (A3.4) (4.43 g, 74%) as a light yellow oil. MS (ISP): m/z=362.2 [M+H]⁺.

Synthesis of the Intermediate Sulfinamide Esters A3.5 and A3.6

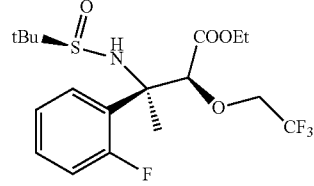

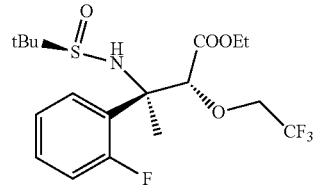

In a dry apparatus under an inert atmosphere a solution of diisopropylamine (1.19 g, 11.8 mmol) in tetrahydrofuran (15 ml) was treated slowly at −20° C. with n-butyllithium (1.6M in hexane, 7.34 ml). The solution was stirred for 30 minutes at 0° C. The freshly prepared solution of lithium diisopropylamide was added dropwise under an inert atmosphere at −78°

C. within 20 minutes to a solution of ethyl 2-(2,2,2-trifluoro-ethoxy)acetate (2.19 g, 11.8 mmol) in tetrahydrofuran (45 ml). The colorless clear solution was stirred at −78° C. for 30 minutes. Thereafter, a solution of (R)-E-N(1-(2-fluorophenyl)ethylidene)-2-methylpropane-sulfinamide (1.13 g, 4.7 mmol) in tetrahydrofuran (4 ml) was added. The mixture was allowed to warm to −20° C. and stirring was continued for 30 minutes. For the workup, the reaction mixture was hydrolyzed with a half-saturated solution of ammonium chloride, then extracted three times with ethyl acetate. The combined organic layers were washed with brine, dried over sodium sulphate, and evaporated at reduced pressure. Purification of the crude product by chromatography on silica gel using a gradient of heptane/ethyl acetate=5/1 to 2:1 as the eluent yielded a 1:6-mixture of the (2S,3R)-3-(2-fluoro-phenyl)-3-((R)-2-methyl-propane-2-sulfinylamino)-2-(2,2,2-trifluoro-ethoxy)-butyric acid ethyl ester (A3.5) and (2R,3R)-3-(2-fluoro-phenyl)-3-((R)-2-methyl-propane-2-sulfinylamino)-2-(2,2,2-trifluoro-ethoxy)-butyric acid ethyl ester (A3.6) as a yellow oil (1.35 g, 67% of theory). MS: m/z=428.2 [M+H]$^+$.

The ethyl 2-(2,2,2-trifluoroethoxy)acetate was obtained in close analogy to the procedure described in EP0532178 for the corresponding methyl ester.

Syntheses of the Intermediate Sulfonamide Esters A3.7 and A3.8 (Via Reformatsky Reaction)

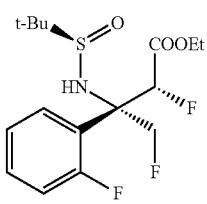

A3.7

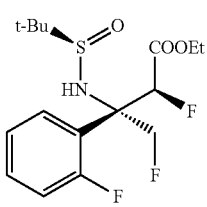

A3.8

Starting from (R)-2-methyl-propane-2-sulfinic acid [2-fluoro-1-(2-fluoro-phenyl)-eth-(Z)-ylidene]-amide (intermediate A2.2) and ethyl 2-bromo-2-fluoroacetate, the faster eluting isomer (2R,3S)-2,4-difluoro-3-(2-fluoro-phenyl)-3-((R)-2-methyl-propane-2-sulfinylamino)-butyric acid ethyl ester was obtained as a yellow oil after chromatography on silica gel (Telos Flash Silica) using a gradient of heptane/ethyl acetate=4:1 to 1:2 as the eluent. MS (ISP): m/z=366.2 [M+H]$^+$.

The second eluting minor isomer, (2S,3S)-2,4-difluoro-3-(2-fluoro-phenyl)-3-((R)-2-methyl-propane-2-sulfinylamino)-butyric acid ethyl ester (intermediate A3.8), was obtained as a yellow oil after chromatography on preparative chiral HPLC (Chiralpak AD; eluent: 40% isopropanol/heptane). MS (ISP): m/z=366.2 [M+H]$^+$.

Synthesis of the Intermediate Sulfonamide Esters A3.9 and A3.10 (Via Reformatsky Reaction)

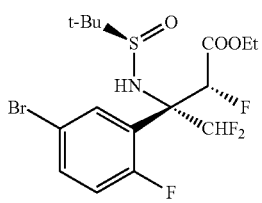

A3.9

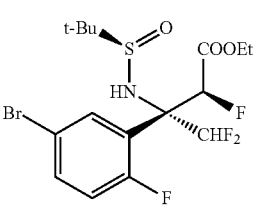

A3.10

Starting from (R)-2-methyl-propane-2-sulfinic acid [1-(5-bromo-2-fluoro-phenyl)-2,2-difluoro-eth-(E)-ylidene]-amide (intermediate A2.3) and ethyl 2-bromo-2-fluoroacetate, a mixture (1 major component) of the 2 diastereoisomers (2R,3R)-3-(5-bromo-2-fluoro-phenyl)-2,4,4-trifluoro-3-((R)-2-methyl-propane-2-sulfinylamino)-butyric acid ethyl ester and (2S,3R)-3-(5-bromo-2-fluoro-phenyl)-2,4,4-trifluoro-3-((R)-2-methyl-propane-2-sulfinylamino)-butyric acid ethyl ester was obtained as a light yellow viscous oil after chromatography on silica gel (Telos Flash Silica) using a gradient of heptane/ethyl acetate=100:0 to 60:30 as the eluent. MS (ISP): m/z=462.2 [M+H]$^+$ and 464.2 [M+2+H]$^+$.

Syntheses of the Intermediate Sulfinamide Alcohols A4

General Procedure

A solution of the sulfinamide ester A3 (12.7 mmol) in dry tetrahydrofuran (50 ml) was treated at 0° C. with lithium borohydride (25.3 mmol) and stirring was continued at 0° C. for 4 h. The reaction mixture was quenched by addition of acetic acid (2 ml) and water (50 ml), extracted with ethyl acetate and the organic layer was dried and evaporated. The residue was purified by chromatography on silica using a mixture of n-heptane and ethyl acetate as the eluent to give the pure intermediate sulfinamide alcohol A4.

Intermediate A4.1

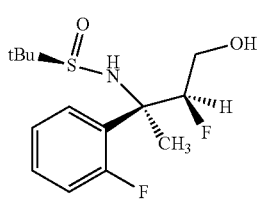

A4.1

Starting from (2S,3R)-2-fluoro-3-(2-fluoro-phenyl)-3-((R)-2-methyl-propane-2-sulfinylamino)-butyric acid ethyl ester (intermediate A3.1), the 2-methyl-propane-2-sulfinic acid [(1R,2S)-2-fluoro-1-(2-fluoro-phenyl)-3-hydroxy-1-methyl-propyl]-amide was obtained as a colorless viscous oil. MS (ISP): m/z=306.1 [M+H]$^+$.

Intermediate A4.2

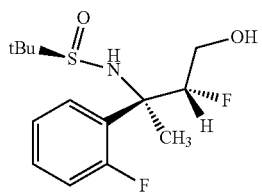

A4.2

Starting from (2R,3R)-2-fluoro-3-(2-fluoro-phenyl)-3-((R)-2-methyl-propane-2-sulfinylamino)-butyric acid ethyl ester (intermediate A3.2), the 2-methyl-propane-2-sulfinic acid [(1R,2R)-2-fluoro-1-(2-fluoro-phenyl)-3-hydroxy-1-methyl-propyl]-amide was obtained as pale red crystals. MS (ISP): m/z=306.1 [M+H]$^+$.

Alternatively, the two epimers A4.1 and A4.2 can be obtained by reduction of its mixture as described above followed by separation on chiral HPLC (Chiralpak AD) where A4.1 is the second eluting epimer, A4.2 the first eluting epimer.

Intermediate A4.3

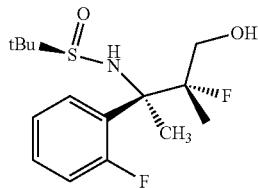

A4.3

Starting from the 1:2-mixture of the (2S,3R)-2-fluoro-3-(2-fluoro-phenyl)-2-methyl-3-((R)-2-methyl-propane-2-sulfinylamino)-butyric acid ethyl ester (intermediate A3.3) and (2R,3R)-2-fluoro-3-(2-fluoro-phenyl)-2-methyl-3-((R)-2-methyl-propane-2-sulfinylamino)-butyric acid ethyl ester (intermediate A3.4), the 2-methyl-propane-2-sulfinic acid [(1R,2R)-2-fluoro-1-(2-fluoro-phenyl)-3-hydroxy-1,2-dimethyl-propyl]-amide (A4.3) was obtained as a white solid. MS (ISP): m/z=320.1 [M+H]$^+$. The minor isomer was not isolated.

Intermediate A4.4

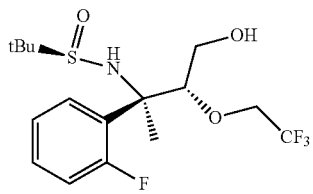

A4.4

Starting from the 1:6-mixture of the (2S,3R)-3-(2-fluoro-phenyl)-3-((R)-2-methyl-propane-2-sulfinylamino)-2-(2,2,2-trifluoro-ethoxy)-butyric acid ethyl ester (intermediate A3.5) and (2R,3R)-3-(2-fluoro-phenyl)-3-((R)-2-methyl-propane-2-sulfinylamino)-2-(2,2,2-trifluoro-ethoxy)-butyric acid ethyl ester (A3.6), the (R)—N-((2R)-2-(2-fluorophenyl)-4-hydroxy-3-(2,2,2-trifluoroethoxy)butan-2-yl)-2-methylpropane-2-sulfinamide (A4.4) was obtained as a pale yellow oil. MS (ISP): m/z=386.1 [M+H]$^+$. The minor isomer was not isolated Intermediate A4.5

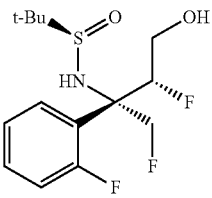

A4.5

Starting from (2R,3S)-2,4-difluoro-3-(2-fluoro-phenyl)-3-((R)-2-methyl-propane-2-sulfinylamino)-butyric acid ethyl ester (intermediate A3.7), the (2R)-methyl-propane-2-sulfinic acid [(1S,2R)-2-fluoro-1-fluoromethyl-1-(2-fluoro-phenyl)-3-hydroxy-propyl]-amide was obtained as a viscous colorless oil. MS (ISP): m/z=324.3 [M+H]$^+$.

Intermediate A4.6

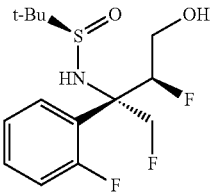

A4.6

Starting from (2S,3S)-2,4-difluoro-3-(2-fluoro-phenyl)-3-((R)-2-methyl-propane-2-sulfinylamino)-butyric acid ethyl ester (intermediate A3.8), the (2R)-methyl-propane-2-sulfinic acid [(1S,2S)-2-fluoro-1-fluoromethyl-1-(2-fluoro-phenyl)-3-hydroxy-propyl]-amide was obtained as a colorless oil. MS (ISP): m/z=324.3 [M+H]$^+$.

Intermediates A4.7 and A4.8

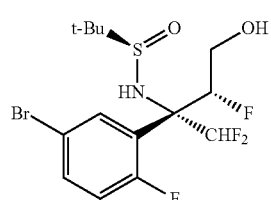

A4.7

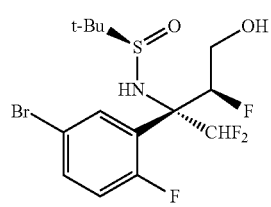

A4.8

Starting from the mixture of (2S,3R)- and (2R,3R)-3-(5-bromo-2-fluoro-phenyl)-2,4,4-trifluoro-3-((R)-2-methyl-propane-2-sulfinylamino)-butyric acid ethyl ester (intermediates A3.9 and A3.10), the mixture of (R)-2-methyl-propane-2-sulfinic acid [(1R,2R)- and (1R,2S)-1-(5-bromo-2-fluoro-phenyl)-1-difluoromethyl-2-fluoro-3-hydroxy-propyl]-amide was obtained as a white foam. MS (ISP): m/z=420.2 [M+H]$^+$ and 422.0 [M+2+H]$^+$.

Syntheses of the Intermediate Amino Alcohols A5
General Procedure

A solution of the sulfinamide alcohol A4 (3.4 mmol) in methanol (12 ml) was treated at 0° C. with a solution of hydrochloric acid in dioxane (17.1 mmol). The reaction mixture was left to warm and kept at room temperature for 16 hours. For the workup, the reaction mixture was evaporated at reduced pressure. The solid residue was partitioned between water (10 ml) and ethyl acetate (25 ml). The aqueous layer was separated, again extracted with ethyl acetate (25 ml). The combined organic layers were washed with water (5 ml), the aqueous layers combined and treated with an aqueous solution of sodium carbonate to adjust the pH to 9-10. Thereafter, the aqueous layer was extracted with ethyl ester (3×35 ml). The combined organic layers were dried over sodium sulphate and evaporated at reduced pressure. The product was engaged in the next step without further purification.

Intermediate Amino Alcohol A5.1

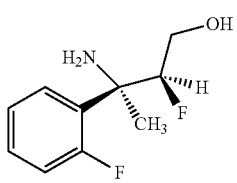

A5.1

Starting from 2-methyl-propane-2-sulfinic acid [(1R,2S)-2-fluoro-1-(2-fluoro-phenyl)-3-hydroxy-1-methyl-propyl]-amide (intermediate A4.1), the (2S,3R)-3-amino-2-fluoro-3-(2-fluoro-phenyl)-butan-1-ol (98% yield) was obtained as a colorless oil. MS (ISP): m/z=202.3 [M+H]$^+$.

Intermediate Amino Alcohol A5.2

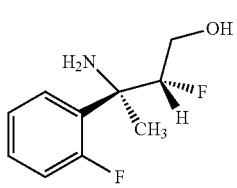

A5.2

Starting from 2-methyl-propane-2-sulfinic acid [(1R,2R)-2-fluoro-1-(2-fluoro-phenyl)-3-hydroxy-1-methyl-propyl]-amide (intermediate A4.2), the (2R,3R)-3-amino-2-fluoro-3-(2-fluoro-phenyl)-butan-1-ol (95% yield) was obtained as a light brown oil. MS (ISP): m/z=202.2 [M+H]$^+$.

Intermediate Amino Alcohol A5.3

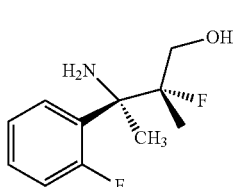

A5.3

Starting from 2-methyl-propane-2-sulfinic acid [(1R,2R)-2-fluoro-1-(2-fluoro-phenyl)-3-hydroxy-1,2-dimethyl-propyl]-amide (intermediate A4.3), the (2R,3R)-3-amino-2-fluoro-3-(2-fluoro-phenyl)-2-methyl-butan-1-ol (A5.3) was obtained as a colorless oil MS (ISP): m/z=216.3 [M+H]$^+$.

Intermediate Amino Alcohol A5.4

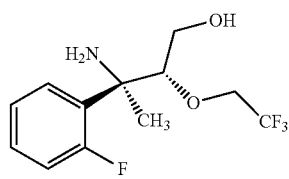

A5.4

Starting from (R)—N-((2R)-2-(2-fluorophenyl)-4-hydroxy-3-(2,2,2-trifluoroethoxy)butan-2-yl)-2-methylpropane-2-sulfinamide (intermediate A4.4), the (2R,3R)-3-amino-3-(2-fluoro-phenyl)-2-(2,2,2-trifluoro-ethoxy)-butan-1-ol (A5.4) was obtained as a colorless oil. MS (ISP): m/z=282.3 [M+H]$^+$ Intermediate Amino Alcohol A5.5

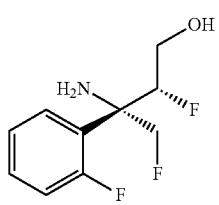

A5.5

Starting from 2-methyl-propane-2-sulfinic acid [(1S,2R)-2-fluoro-1-fluoromethyl-1-(2-fluoro-phenyl)-3-hydroxy-propyl]-amide (intermediate A4.5), the (2R,3S)-3-amino-2,4-difluoro-3-(2-fluoro-phenyl)-butan-1-ol was obtained as a light yellow viscous oil. MS (ISP): m/z=220.2 [M+H]$^+$.

Intermediate Amino Alcohol A5.6

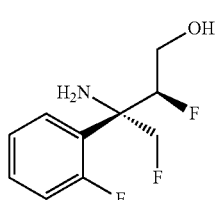

A5.6

Starting from 2-methyl-propane-2-sulfinic acid [(1S,2S)-2-fluoro-1-fluoromethyl-1-(2-fluoro-phenyl)-3-hydroxy-propyl]-amide (intermediate A4.6), the (2S,3S)-3-amino-2,4-difluoro-3-(2-fluoro-phenyl)-butan-1-ol was obtained as a light yellow oil. MS (ISP): m/z=220.3 [M+H]$^+$.

Intermediates A5.7 and A5.8

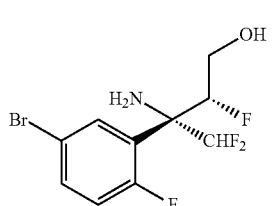

A5.7

-continued

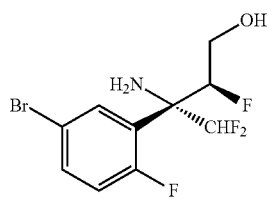
A5.8

Starting from the mixture of (R)-2-methyl-propane-2-sulfinic acid [(1R,2R)- and (1R,2S)-1-(5-bromo-2-fluoro-phenyl)-1-difluoromethyl-2-fluoro-3-hydroxy-propyl]-amide (intermediates A4.7 and A4.8), the (2R,3R)- and (2S,3R)-3-amino-3-(5-bromo-2-fluoro-phenyl)-2,4,4-trifluoro-butan-1-ol was obtained as a viscous light yellow oil. MS (ISP): m/z=315.9 [M+H]+ and 317.9 [M+2+H].

Syntheses of the Intermediate Amino Oxazines A6
General Procedure

A dried tube was charged with a mixture of the amino alcohol A5 (18.8 mmol), cyanogen bromide (33.9 mmol) and ethanol (61 ml). The tube was sealed and heated at 90° C. for 16 hours. For the workup, the reaction mixture was cooled and evaporated at reduced pressure. The residue was partitioned between ethyl acetate (150 ml) and a saturated aqueous solution of sodium carbonate (50 ml). The aqueous layer was separated and re-extracted with ethyl acetate (2×50 ml). The organic layers were washed with brine (50 ml), then combined, dried over sodium sulphate and evaporated at reduced pressure. The product was used in the next step without further purification.

Intermediate Amino Oxazine A6.1

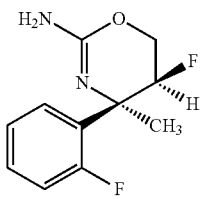
A6.1

Starting from (2S,3R)-3-amino-2-fluoro-3-(2-fluoro-phenyl)-butan-1-ol (intermediate A5.1), the (4R,5S)-5-fluoro-4-(2-fluoro-phenyl)-4-methyl-5,6-dihydro-4H-[1,3]oxazin-2-ylamine (85% yield) was obtained as a colorless viscous oil. MS (ISP): m/z=227.2 [M+H]+.

Intermediate Amino Oxazine A6.2

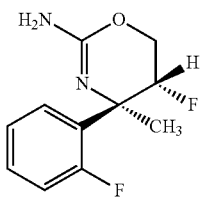
A6.2

Starting from (2R,3R)-3-amino-2-fluoro-3-(2-fluoro-phenyl)-butan-1-ol (intermediate A5.2), the (4R,5R)-5-fluoro-4-(2-fluoro-phenyl)-4-methyl-5,6-dihydro-4H-[1,3]oxazin-2-ylamine was obtained in quantitative yield as a light yellow solid. MS (ISP): m/z=227.2 [M+H]+.

Intermediate Amino Oxazine A6.3

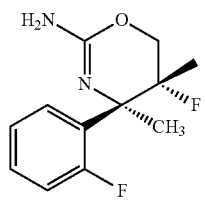
A6.3

Starting from (2R,3R)-3-amino-2-fluoro-3-(2-fluoro-phenyl)-2-methyl-butan-1-ol (intermediate A5.3), the (4R,5R)-5-fluoro-4-(2-fluoro-phenyl)-4,5-dimethyl-5,6-dihydro-4H-[1,3]oxazin-2-ylamine (A6.3) was obtained as a white solid. MS (ISP): m/z=241.2 [M+H]+.

Intermediate Amino Oxazine A6.4

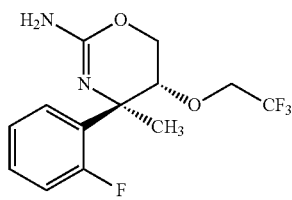
A6.4

Starting from (2R,3R)-3-amino-3-(2-fluoro-phenyl)-2-(2,2,2-trifluoro-ethoxy)-butan-1-ol (intermediate A5.4), the (4R,5R)-4-(2-fluoro-phenyl)-4-methyl-5-(2,2,2-trifluoro-ethoxy)-5,6-dihydro-4H-[1,3]oxazin-2-ylamine (A6.4) was obtained as a colorless oil. MS (ISP): m/z=307.2 [M+H]+.

Intermediate Amino Oxazine A6.5

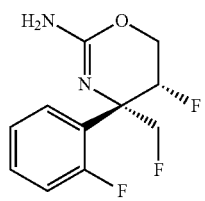
A6.5

Starting from (2R,3S)-3-amino-2,4-difluoro-3-(2-fluoro-phenyl)-butan-1-ol (intermediate A5.5) the (4S,5R)-5-fluoro-4-fluoromethyl-4-(2-fluoro-phenyl)-5,6-dihydro-4H-[1,3]oxazin-2-ylamine was obtained as a white solid. MS (ISP): m/z=245.2 [M+H]+.

Intermediate Amino Oxazine A6.6

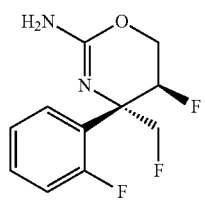
A6.6

Starting from (2S,3S)-3-amino-2,4-difluoro-3-(2-fluoro-phenyl)-butan-1-ol (intermediate A5.6) the (4S,5S)-5-fluoro- 4-fluoromethyl-4-(2-fluoro-phenyl)-5,6-dihydro-4H-[1,3] oxazin-2-ylamine was obtained as a white solid. MS (ISP): m/z=245.2 [M+H]⁺.

Alternative Synthesis of the Intermediate Amino Oxazines A6' Via N-Acyl Amino Oxazines D3

General Procedure

A solution of the N-acyl amino oxazine D3 (761 μmol) in methanol (12 ml) was treated with potassium carbonate (383 mg, 2.74 mmol, 3.6 eq). The reaction mixture was stirred at 50° C. overnight, thereafter evaporated at reduced pressure. The crude material was directly purified by chromatography on silica gel (Telos Flash Silica) using a gradient of heptane and ethyl acetate as the eluent.

Intermediate Amino Oxazines A6'.1 and A6'.2

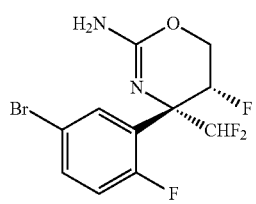

A6'.1

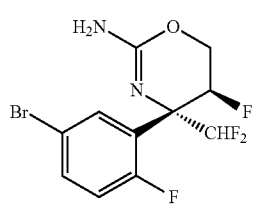

A6'.2

Starting from N-[(4R,5R)- and (4R,5S)-4-(5-bromo-2-fluoro-phenyl)-4-difluoromethyl-5-fluoro-5,6-dihydro-4H-[1,3]oxazin-2-yl]-benzamide (intermediates D3.1 and D3.2) the (4R,5R)- and (4R,5S)-4-(5-bromo-2-fluoro-phenyl)-4-difluoromethyl-5-fluoro-5,6-dihydro-4H-[1,3]oxazin-2-ylamine was obtained as a white crystalline solid. MS (ISP): m/z=341.1 [M+H]⁺, 343.3 [M+2+H]⁺.

Syntheses of the Intermediate Nitro Oxazines A7

General Procedure

A dispersion of the amino oxazine A6 (2.8 mmol) in sulfuric acid (22.1 g, 216 mmol) was cooled to 0° C. and stirring was continued until a complete solution was obtained. At 0° C. fuming nitric acid (300 mg, 214 μl, 4.29 mmol) was added dropwise in 4 portions. After complete addition, the ice bath was removed and stirring continued for 30 minutes at room temperature. For the workup, the solution was added dropwise to a mixture of crushed ice (50 g) and water (50 g). With an aqueous solution of sodium hydroxide the pH was adjusted to 7-8. The aqueous layer was extracted twice with ethyl acetate, thereafter the combined organic layers were washed with brine, then dried over sodium sulphate and evaporated at reduced pressure. The product was engaged in the step without further purification.

Intermediate Nitro Oxazine A7.1

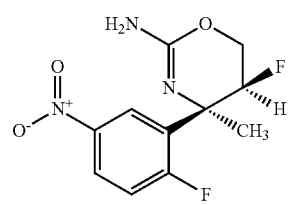

A7.1

Starting from (4R,5S)-5-fluoro-4-(2-fluoro-phenyl)-4-methyl-5,6-dihydro-4H-[1,3]oxazin-2-ylamine (intermediate A6.1), (4R,5S)-5-fluoro-4-(2-fluoro-5-nitro-phenyl)-4-methyl-5,6-dihydro-4H-[1,3]oxazin-2-ylamine (86% yield) was obtained as light yellow foam. MS (ISP): m/z=272.1 [M+H]⁺.

Intermediate Nitro Oxazine A7.2

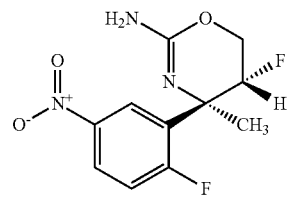

A7.2

Starting from (4R,5R)-5-fluoro-4-(2-fluoro-phenyl)-4-methyl-5,6-dihydro-4H-[1,3]oxazin-2-ylamine (intermediate A6.2), the (4R,5R)-5-fluoro-4-(2-fluoro-5-nitro-phenyl)-4-methyl-5,6-dihydro-4H-[1,3]oxazin-2-ylamine (75% yield) was obtained as a white foam. MS (ISP): m/z=272.3 [M+H]⁺.

Intermediate Nitro Oxazine A7.3

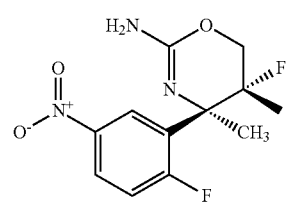

A7.3

Starting from (4R,5R)-5-fluoro-4-(2-fluoro-phenyl)-4,5-dimethyl-5,6-dihydro-4H-[1,3]oxazin-2-ylamine (intermediate A6.3), the (4R,5R)-5-fluoro-4-(2-fluoro-5-nitro-phenyl)-4,5-dimethyl-5,6-dihydro-4H-[1,3]oxazin-2-ylamine (A7.3) was obtained as a pale yellow oil. MS (ISP): m/z=286.1 [M+H]⁺.

Intermediate Nitro Oxazine A7.4

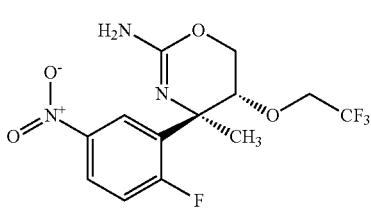

A7.4

Starting from (4R,5R)-4-(2-fluoro-phenyl)-4-methyl-5-(2,2,2-trifluoro-ethoxy)-5,6-dihydro-4H-[1,3]oxazin-2-ylamine (intermediate A6.4), the (4R,5R)-4-(2-fluoro-5-nitro-phenyl)-4-methyl-5-(2,2,2-trifluoro-ethoxy)-5,6-dihydro-4H-[1,3]oxazin-2-ylamine (A7.4) was obtained as a pale yellow foam. MS (ISP): m/z=352.2 [M+H]⁺.

Intermediate Nitro Oxazine A7.5

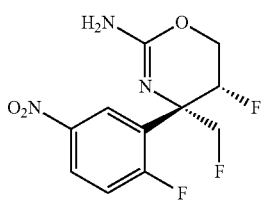

A7.5

Starting from (4S,5R)-5-fluoro-4-fluoromethyl-4-(2-fluoro-phenyl)-5,6-dihydro-4H-[1,3]oxazin-2-ylamine (intermediate A6.5) the (4S,5R)-5-fluoro-4-fluoromethyl-4-(2-fluoro-5-nitro-phenyl)-5,6-dihydro-4H-[1,3]oxazin-2-ylamine was obtained as a light yellow solid. MS (ISP): m/z=290.1 [M+H]⁺.

Intermediate Nitro Oxazine A7.6

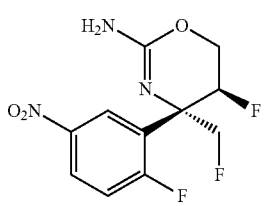

A7.6

Starting from (4S,5S)-5-fluoro-4-fluoromethyl-4-(2-fluoro-phenyl)-5,6-dihydro-4H-[1,3]oxazin-2-ylamine (intermediate A6.6) the (4S,5S)-5-fluoro-4-fluoromethyl-4-(2-fluoro-5-nitro-phenyl)-5,6-dihydro-4H-[1,3]oxazin-2-ylamine was obtained as a light yellow solid. MS (ISP): m/z=290.1 [M+H]⁺.

Syntheses of the Intermediate Anilines A8

General Procedure

A solution of the nitro oxazine A7 (3 mmol) in ethanol (31 ml) was hydrogenated at atmospheric pressure using palladium (10% on carbon) (159 mg, 150 µmol) as the catalyst. After 90 minutes the reaction was complete. The reaction mixture was filtrated over a layer of Dicalit, which was washed with ethanol (3×20 ml). The combined solutions of ethanol were evaporated at reduced pressure. The product was engaged in the step without further purification.

Intermediate Aniline A8.1

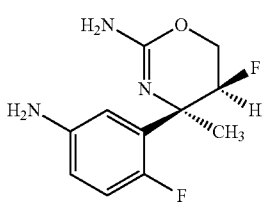

A8.1

Starting from (4R,5S)-5-fluoro-4-(2-fluoro-5-nitro-phenyl)-4-methyl-5,6-dihydro-4H-[1,3]oxazin-2-ylamine (intermediate A7.1), (4R,5S)-4-(5-amino-2-fluoro-phenyl)-5-fluoro-4-methyl-5,6-dihydro-4H-[1,3]oxazin-2-ylamine (98% yield) was obtained as white foam. MS (ISP): m/z=242.2 [M+H]⁺.

Intermediate Aniline A8.2

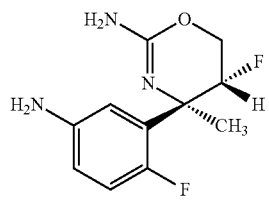

A8.2

Starting from (4R,5R)-5-fluoro-4-(2-fluoro-5-nitro-phenyl)-4-methyl-5,6-dihydro-4H-[1,3]oxazin-2-ylamine (intermediate A7.2), the (4R,5R)-4-(5-amino-2-fluoro-phenyl)-5-fluoro-4-methyl-5,6-dihydro-4H-[1,3]oxazin-2-ylamine (97% yield) was obtained as a white foam. MS (ISP): m/z=242.3 [M+H]⁺.

Intermediate Aniline A8.3

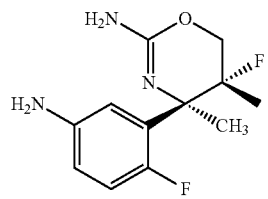

A8.3

Starting from (4R,5R)-5-fluoro-4-(2-fluoro-5-nitro-phenyl)-4,5-dimethyl-5,6-dihydro-4H-[1,3]oxazin-2-ylamine (intermediate A7.3), the (4R,5R)-4-(5-amino-2-fluoro-phenyl)-5-fluoro-4,5-dimethyl-5,6-dihydro-4H-[1,3]oxazin-2-ylamine (A8.3) was obtained as a white solid. MS (ISP): m/z=265.2 [M+H]⁺.

Intermediate Aniline A8.4

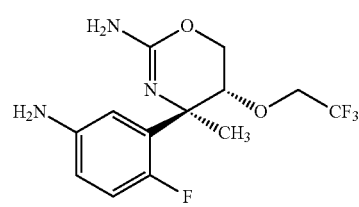

A8.4

Starting from (4R,5R)-4-(2-fluoro-5-nitro-phenyl)-4-methyl-5-(2,2,2-trifluoro-ethoxy)-5,6-dihydro-4H-[1,3]oxazin-2-ylamine (intermediate A7.4), the (4R,5R)-4-(5-amino-2-fluoro-phenyl)-4-methyl-5-(2,2,2-trifluoro-ethoxy)-5,6-dihydro-4H-[1,3]oxazin-2-ylamine (A8.4) was obtained as a pale yellow solid. MS (ISP): m/z=322.2 [M+H]⁺.

Intermediate Aniline A8.5

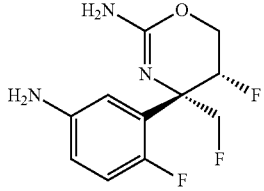

A8.5

Starting from (4S,5R)-5-fluoro-4-fluoromethyl-4-(2-fluoro-5-nitro-phenyl)-5,6-dihydro-4H-[1,3]oxazin-2-ylamine (intermediate A7.5) the (4S,5R)-4-(5-amino-2-fluoro-phenyl)-5-fluoro-4-fluoromethyl-5,6-dihydro-4H-[1,3]oxazin-2-ylamine was obtained as an off-white solid. MS (ISP): m/z=260.2 [M+H]$^+$.

Intermediate Aniline A8.6

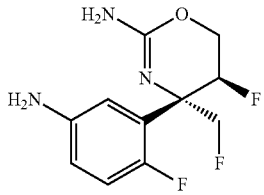

A8.6

Starting from (4S,5S)-5-fluoro-4-fluoromethyl-4-(2-fluoro-5-nitro-phenyl)-5,6-dihydro-4H-[1,3]oxazin-2-ylamine (intermediate A7.5) the (4S,5S)-4-(5-amino-2-fluoro-phenyl)-5-fluoro-4-fluoromethyl-5,6-dihydro-4H-[1,3]oxazin-2-ylamine was obtained as a white foam. MS (ISP): m/z=260.2 [M+H]$^+$.

Alternative Synthesis of the Intermediate Anilines A8
General Procedure

A solution of the DMTr-imine B2 (219 µmol) in dichloromethane (3 ml) was treated at 22° C. with trifluoroacetic acid (171 µl, 2.19 mmol, 10 eq). After 30 minutes (the progress of the reaction was followed by TLC) the solution was evaporated. Thereafter, to the crude intermediate imine B3 was added hydrochloric acid (1 M; 2.19 ml, 10 eq). After 30 minutes at room temperature (the progress of the reaction was followed by TLC) the reaction mixture was poured into a cold solution of sodium carbonate (1 M; 14 ml). The aqueous phase was extracted 3 times with dichloromethane, the combined organic layers were washed with brine, dried over sodium sulphate and evaporated. The residue was purified by chromatography on silica-NH$_2$ (Telos Flash NH$_2$) using a gradient of heptane and ethyl acetate as the eluent.

Intermediate Anilines A8.7 and A8.8

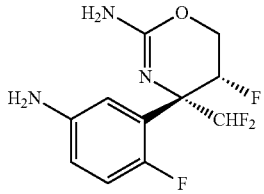

A8.7

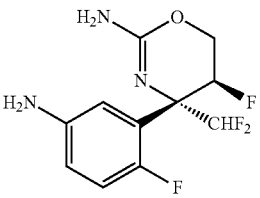

A8.8

Starting from {(4R,5R)- and (4R,5S)-4-[5-(benzhydrylidene-amino)-2-fluoro-phenyl]-4-difluoromethyl-5-fluoro-5,6-dihydro-4H-[1,3]oxazin-2-yl}-[bis-(4-methoxy-phenyl)-phenyl-methyl]-amine (intermediates B2.1 and B2.2) the (4R,5R)- and (4R,5S)-4-(5-amino-2-fluoro-phenyl)-4-difluoromethyl-5-fluoro-5,6-dihydro-4H-[1,3]oxazin-2-ylamine was obtained as a light yellow crystalline material. MS (ISP): m/z=278.4 [M+H]$^+$.

Synthesis of the Intermediate DMTr-Oxazines B
General Procedure

A solution of the amino oxazines A6' (574 µmol) in dichloromethane (8 ml) was treated subsequently at 0° C. with N-ethyldiisopropylamine (195 µl, 1.15 mmol, 2 eq) and 4,4'-dimethoxytriphenylmethyl chloride (292 mg, 861 mol, 1.5 eq). After 16 hours at 22° C. the reaction mixture was washed with water, the organic layer was separated, dried over sodium sulphate, and evaporated. The residue was purified by chromatography on silica gel (Telos Flash Silica) using a gradient of heptane and ethyl acetate as the eluent.

Intermediates B1.1 and B1.2

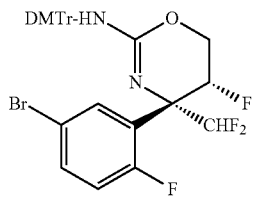

B1.1

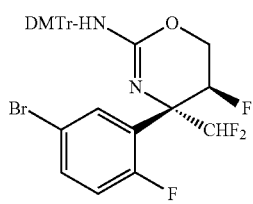

B1.2

Starting from (4R,5R)- and (4R,5S)-4-(5-bromo-2-fluoro-phenyl)-4-difluoromethyl-5-fluoro-5,6-dihydro-4H-[1,3]oxazin-2-ylamine (intermediates A6'.1 and A6'.2) the [bis-(4-methoxy-phenyl)-phenyl-methyl]-[(4R,5S)- and (4R,5S)-4-(5-bromo-2-fluoro-phenyl)-4-difluoromethyl-5-fluoro-5,6-dihydro-4H-[1,3]oxazin-2-yl]-amine was obtained as a white solid. R$_f$: 0.52 (SiO$_2$; heptane:ethyl acetate=2:1; detection: UV, 254 nm).

Synthesis of the Intermediate Imine B2
General Procedure

A solution of the DMTr-oxazine B1 (454 µmol) in toluene (6 ml) was treated subsequently under an argon atmosphere at 22° C. with sodium tert-butoxide (131 mg, 1.36 mmol, 3 eq), 2-di-tert-butylphosphino-2',4',6'-triisopropylbiphenyl (28.9 mg, 68.1 µmol, 0.15 eq), tris(dibenzylideneacetone)dipalladium(0) chloroform adduct (24.2 mg, 22.7 µmol, 0.05 eq), and benzophenone imine (170 mg, 157 µl, 908 µmol, 2 eq).

The tube was sealed and heated to 105° C. for 60 hours. The mixture was cooled to 22° C., evaporated at reduced pressure and purified by chromatography on an amine phase (Telos Flash NH₂) using a gradient of heptane and ethyl acetate as the eluent.

Intermediates B2.1 and B2.2

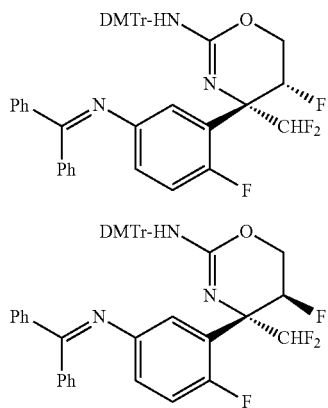

Starting from [bis-(4-methoxy-phenyl)-phenyl-methyl]-[(4R,5S)- and (4R,5S)-4-(5-bromo-2-fluoro-phenyl)-4-difluoromethyl-5-fluoro-5,6-dihydro-4H-[1,3]oxazin-2-yl]-amine (intermediates B1.1 and B1.2) the {(4R,5R)- and (4R,5S)-4-[5-(benzhydrylidene-amino)-2-fluoro-phenyl]-4-difluoromethyl-5-fluoro-5,6-dihydro-4H-[1,3]oxazin-2-yl}-[bis-(4-methoxy-phenyl)-phenyl-methyl]-amine was obtained as a light yellow foam. MS (ISP): m/z=744.5 [M+H]⁺, 442.4 [M-DMTr+H]⁺.

Synthesis of Intermediate O-Protected Amino Alcohol D1

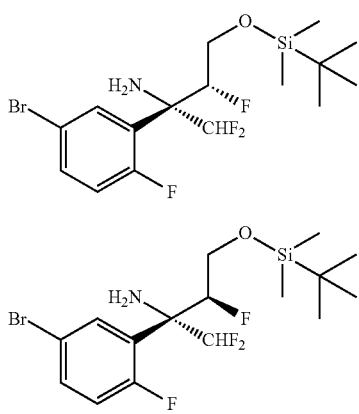

A solution of (2R,3R)- and (2S,3R)-3-amino-3-(5-bromo-2-fluoro-phenyl)-2,4,4-trifluoro-butan-1-ol (4.49 g, 14.2 mmol) (intermediates A5.7 and A5.8) in dichloromethane (120 ml) was treated with triethylamine (4.35 ml, 31.3 mmol), 4-dimethylaminopyridine (868 mg, 7.11 mmol), and tert-butyl-chloro-dimethyl-silane (4.51 g, 28.4 mmol) and stirred at room temperature overnight. For the workup, the reaction mixture was extracted with a saturated solution of sodium hydrogencarbonate (40 ml), water (40 ml) and brine (40 ml). The aqueous hydrogencarbonate solution was extracted with dichloromethane, then the organic layers were combined, dried over sodium sulphate and evaporated. The crude product was purified by chromatography on silica gel (Telos Flash Silica) using a gradient of heptane/ethyl acetate=100:0 to 90:10 as the eluent. The (1R,2R)- and (1R,2S)-1-(5-bromo-2-fluoro-phenyl)-3-(tert-butyl-dimethyl-silanyloxy)-1-difluoromethyl-2-fluoro-propylamine (2.05 g, 85% of theory) was obtained as a viscous colorless oil. MS (ISP): m/z=430.3 [M+H]⁺ and 432.2 [M+2+H]⁺.

Synthesis of Intermediate O-Protected Isothiocyanate Adduct D2

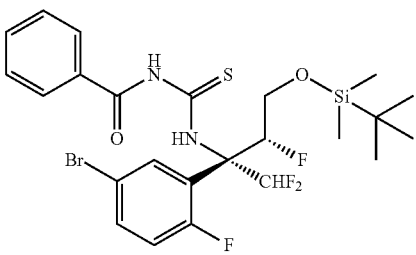

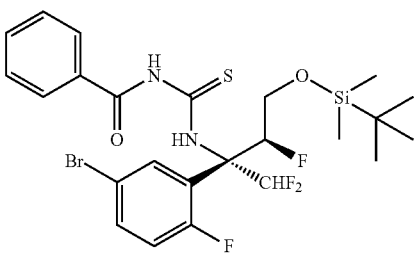

In a microwave tube (1R,2R)- and (1R,2S)-1-(5-bromo-2-fluoro-phenyl)-3-(tert-butyl-dimethyl-silanyloxy)-1-difluoromethyl-2-fluoro-propylamine (intermediates D1.1 and D1.2) (2.4551 g, 5.7 mmol) and benzoyl isothiocyanate (1.12 g, 6.85 mmol) were dissolved in acetone (25 ml). The tube was sealed and heated at 70° C. overnight. For the workup, the reaction mixture was evaporated at reduced pressure and the residue directly purified by chromatography on silica gel (Telos Flash Silica) using a gradient of heptane/ethyl acetate=100:0 to 80:20 as the eluent. The 1-benzoyl-3-[(1R,2R)- and (1R,2S)-1-(5-bromo-2-fluoro-phenyl)-3-(tert-butyl-dimethyl-silanyloxy)-1-difluoromethyl-2-fluoro-propyl]-thiourea (2.05 g, 61% of theory) was obtained as a light yellow foam. MS (ISP): m/z=623.0 [M+H]⁺ and 625.1 [M+2+H]⁺.

Synthesis of Intermediate Oxazine D3

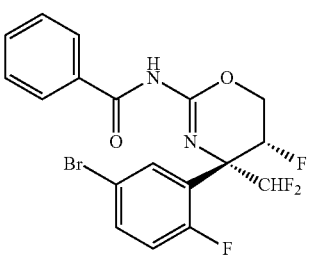

-continued

D3.2

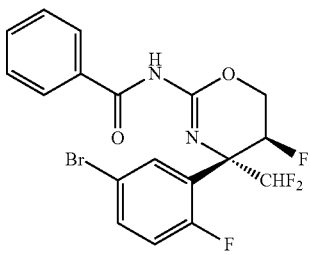

A solution of 1-benzoyl-3-[(1R,2R)- and (1R,2S)-1-(5-bromo-2-fluoro-phenyl)-3-(tert-butyl-dimethyl-silanyloxy)-1-difluoromethyl-2-fluoro-propyl]-thiourea (intermediates D2.1 and D2.2) (2.021 g, 3.41 mmol) in dichloromethane (100 ml) was cooled to 0° C. and trimethyloxonium tetrafluoroborate (557 mg, 3.58 mmol) was added in one portion. The reaction mixture was stirred at 0° C. for 40 minutes, then for 3 hours at room temperature. In order to complete the reaction another equivalent of trimethyloxonium tetrafluoroborate (557 mg, 3.58 mmol) was added and stirring continued overnight. For the workup, the reaction mixture was evaporated and the residue directly purified by chromatography on silica gel (Telos Flash Silica) using a gradient of heptane/ethyl acetate=100:0 to 0:100 as the eluent. The N-[(4R,5R)- and (4R,5S)-4-(5-bromo-2-fluoro-phenyl)-4-difluoromethyl-5-fluoro-5,6-dihydro-4H-[1,3]oxazin-2-yl]-benzamide (962 mg, 63.5% of theory) as a white foam. MS (ISP): m/z=445.4 [M+H]$^+$ and 447.3 [M+2+H]$^+$.

Synthesis of the Amides of Formula I

General Procedure I:

A solution of the carboxylic acid (0.23 mmol) in methanol (5 ml) was cooled to 0° C. 4-(4,6-Dimethoxy[1.3.5]triazin-2-yl)-4-methylmorpholinium chloride hydrate (DMTMM) (80 mg, 0.27 mmol) was added and the solution was stirred at 0° C. for 30 minutes. Thereafter, a solution of the intermediate diamine A8 (0.21 mmol) in methanol (5 ml) was added dropwise at 0° C. via syringe. The reaction mixture was stirred at 23° C. for 18-60 hours. For the workup, the reaction mixture was poured into a solution of sodium carbonate (1M) followed by the extraction with dichloromethane. The organic layer was separated, washed with brine and dried over sodium sulphate. Removal of the solvent at reduced pressure left a light brown oil which was purified by chromatography on silica gel using a mixture of dichloromethane and methanol (0-10%) to give the pure amides of formula I.

The following examples have a basic group. Depending on the reaction and purification conditions they were isolated in either the free base form, or as a salt, or in both free base and salt forms.

Example 1

5-Chloro-pyridine-2-carboxylic acid [3-((4R,5R)-2-amino-5-fluoro-4-methyl-5,6-dihydro-4H-[1,3]oxazin-4-yl)-4-fluoro-phenyl]-amide The condensation of (4R,5R)-4-(5-amino-2-fluoro-phenyl)-5-fluoro-4-methyl-5,6-dihydro-4H-[1,3]oxazin-2-ylamine (intermediate A8.2) and 5-chloro-pyridine-2-carboxylic acid following procedure I yielded the title compound as a crystalline white solid. MS (ISP): m/z=381.2 [M+H]$^+$.

Example 2

3,5-Dichloro-pyridine-2-carboxylic acid [3-((4R,5R)-2-amino-5-fluoro-4-methyl-5,6-dihydro-4H-[1,3]oxazin-4-yl)-4-fluoro-phenyl]-amide The condensation of (4R,5R)-4-(5-amino-2-fluoro-phenyl)-5-fluoro-4-methyl-5,6-dihydro-4H-[1,3]oxazin-2-ylamine (intermediate A8.2) and 3,5-dichloro-pyridine-2-carboxylic acid (CAS 81719-53-1) following procedure I yielded the title compound as a crystalline white solid. MS (ISP): m/z=415.1 [M+H]$^+$ and 417.1 [M+2+H]$^+$.

Example 3

3,5-Difluoro-pyridine-2-carboxylic acid [3-((4R,5R)-2-amino-5-fluoro-4-methyl-5,6-dihydro-4H-[1,3]oxazin-4-yl)-4-fluoro-phenyl]-amide The condensation of (4R,5R)-4-(5-amino-2-fluoro-phenyl)-5-fluoro-4-methyl-5,6-dihydro-4H-[1,3]oxazin-2-ylamine (intermediate A8.2) and 3,5-difluoro-pyridine-2-carboxylic acid (CAS 745784-04-7) following procedure I yielded the title compound as a white solid. MS (ISP): m/z=383.3 [M+H]$^+$.

Example 4

5-Cyano-pyridine-2-carboxylic acid [3-((4R,5R)-2-amino-5-fluoro-4-methyl-5,6-dihydro-4H-[1,3]oxazin-4-yl)-4-fluoro-phenyl]-amide The condensation of (4R,5R)-4-(5-amino-2-fluoro-phenyl)-5-fluoro-4-methyl-5,6-dihydro-4H-[1,3]oxazin-2-ylamine (intermediate A8.2) and 5-cyano-pyridine-2-carboxylic acid (CAS 53234-55-2) following procedure I yielded the title compound as a crystalline white solid. MS (ISP): m/z=372.2 [M+H]$^+$.

Example 5

5-Fluoromethoxy-pyridine-2-carboxylic acid [3-((4R,5R)-2-amino-5-fluoro-4-methyl-5,6-dihydro-4H-[1,3]oxazin-4-yl)-4-fluoro-phenyl]-

The condensation of (4R,5R)-4-(5-amino-2-fluoro-phenyl)-5-fluoro-4-methyl-5,6-dihydro-4H-[1,3]oxazin-2-ylamine (intermediate A8.2) and 5-fluoromethoxy-pyridine-2-carboxylic acid (CAS 1174321-03-9) following procedure I yielded the title compound as a white foam. MS (ISP): m/z=395.1 [M+H]$^+$.

Example 6

5-Difluoromethoxy-pyridine-2-carboxylic acid [3-((4R,5R)-2-amino-5-fluoro-4-methyl-5,6-dihydro-4H-[1,3]oxazin-4-yl)-4-fluoro-phenyl]-amide The condensation of (4R,5R)-4-(5-amino-2-fluoro-phenyl)-5-fluoro-4-methyl-5,6-dihydro-4H-[1,3]oxazin-2-ylamine (intermediate A8.2) and 5-difluoromethoxy-pyridine-2-carboxylic acid (CAS 1174323-34-2) following procedure I yielded the title compound as a white foam. MS (ISP): m/z=413.3 [M+H]$^+$.

Example 7

3-Chloro-5-cyano-pyridine-2-carboxylic acid [3-((4R,5R)-2-amino-5-fluoro-4-methyl-5,6-dihydro-4H-[1,3]oxazin-4-yl)-4-fluoro-phenyl]-amide The condensation of (4R,5R)-4-(5-amino-2-fluoro-phenyl)-5-fluoro-4-methyl-5,6-dihydro-4H-[1,3]oxazin-2-ylamine (intermediate A8.2) and 3-chloro-5-cyano-pyridine-2-carboxylic acid (CAS 1200497-81-9) following procedure I yielded the title compound as a white solid. MS (ISP): m/z=406.2 [M+H]$^+$.

Example 8

5-Chloro-3-fluoro-pyridine-2-carboxylic acid [3-((4R,5R)-2-amino-5-fluoro-4-methyl-5,6-dihydro-4H-[1,3]oxazin-4-yl)-4-fluoro-phenyl]-amide The condensation of (4R,5R)-4-(5-amino-2-fluoro-phenyl)-5-fluoro-4-methyl-5,6-dihydro-4H-[1,3]oxazin-2-ylamine (intermediate A8.2) and 5-chloro-3-fluoro-pyridine-2-carboxylic acid (CAS 207994-08-9) following procedure I yielded the title compound as a white solid. MS (ISP): m/z=399.1 [M+H]$^+$.

Example 9

3-Chloro-5-trifluoromethyl-pyridine-2-carboxylic acid [3-((4R,5R)-2-amino-5-fluoro-4-methyl-5,6-dihydro-4H-[1,3]oxazin-4-yl)-4-fluoro-phenyl]-amide The condensation of (4R,5R)-4-(5-amino-2-fluoro-phenyl)-5-fluoro-4-methyl-5,6-dihydro-4H-[1,3]oxazin-2-ylamine (intermediate A8.2) and 3-chloro-5-trifluoromethyl-pyridine-2-carboxylic acid (CAS 80194-68-9) following procedure I yielded the title compound as a white foam. MS (ISP): m/z=449.1 [M+H]$^+$.

Example 10

5-Fluoromethoxy-pyrazine-2-carboxylic acid [3-((4R,5R)-2-amino-5-fluoro-4-methyl-5,6-dihydro-4H-[1,3]oxazin-4-yl)-4-fluoro-phenyl]-amide The condensation of (4R,5R)-4-(5-amino-2-fluoro-phenyl)-5-fluoro-4-methyl-5,6-dihydro-4H-[1,3]oxazin-2-ylamine (intermediate A8.2) and 5-fluoromethoxy-pyrazine-2-carboxylic acid (CAS 1174321-00-6) following procedure I yielded the title compound as a white foam. MS (ISP): m/z=396.2 [M+H]$^+$.

Example 11

5-Difluoromethyl-pyridine-2-carboxylic acid [3-((4R,5R)-2-amino-5-fluoro-4-methyl-5,6-dihydro-4H-[1,3]oxazin-4-yl)-4-fluoro-phenyl]-amide The condensation of (4R,5R)-4-(5-amino-2-fluoro-phenyl)-5-fluoro-4-methyl-5,6-dihydro-4H-[1,3]oxazin-2-ylamine (intermediate A8.2) and 5-difluoromethyl-pyridine-2-carboxylic acid following procedure I yielded the title compound as a white foam. MS (ISP): m/z=397.3 [M+H]$^+$.

The 5-difluoromethyl-pyridine-2-carboxylic acid (CAS 859538-41-3) was obtained starting from 5-methyl-pyridine-2-carboxylic acid in close analogy to the preparation of the corresponding 5-difluoromethyl-pyrazine-2-carboxylic acid as described in US2009209757.

Example 12

3-Fluoro-5-trifluoromethyl-pyridine-2-carboxylic acid [3-((4R,5R)-2-amino-5-fluoro-4-methyl-5,6-dihydro-4H-[1,3]oxazin-4-yl)-4-fluoro-phenyl]-amide The condensation of (4R,5R)-4-(5-amino-2-fluoro-phenyl)-5-fluoro-4-methyl-5,6-dihydro-4H-[1,3]oxazin-2-ylamine (intermediate A8.2) and 3-fluoro-5-trifluoromethyl-pyridine-2-carboxylic acid (CAS 89402-28-8) following procedure I yielded the title compound as a white foam. MS (ISP): m/z=433.3 [M+H]$^+$.

Example 13

5-Methoxy-pyridine-2-carboxylic acid [3-((4R,5R)-2-amino-5-fluoro-4-methyl-5,6-dihydro-4H-[1,3]oxazin-4-yl)-4-fluoro-phenyl]-amide The condensation of (4R,5R)-4-(5-amino-2-fluoro-phenyl)-5-fluoro-4-methyl-5,6-dihydro-4H-[1,3]oxazin-2-ylamine (intermediate A8.2) and 5-methoxy-pyridine-2-carboxylic acid (CAS 29082-92-6) following procedure I yielded the title compound as a white solid. MS (ISP): m/z=377.3 [M+H]$^+$.

Example 14

5-Cyclopropylethynyl-pyridine-2-carboxylic acid [3-((4R,5R)-2-amino-5-fluoro-4-methyl-5,6-dihydro-4H-[1,3]oxazin-4-yl)-4-fluoro-phenyl]-amide The condensation of (4R,5R)-4-(5-amino-2-fluoro-phenyl)-5-fluoro-4-methyl-5,6-dihydro-4H-[1,3]oxazin-2-ylamine (intermediate A8.2) and 5-cyclopropylethynyl-pyridine-2-carboxylic acid (CAS 1174322-62-3; WO2009091016) following procedure I yielded the title compound as a white foam. MS (ISP): m/z=411.3 [M+H]$^+$.

Example 15

5-Difluoromethyl-pyrazine-2-carboxylic acid [3-((4R,5R)-2-amino-5-fluoro-4-methyl-5,6-dihydro-4H-[1,3]oxazin-4-yl)-4-fluoro-phenyl]-amide The condensation of (4R,5R)-4-(5-amino-2-fluoro-phenyl)-5-fluoro-4-methyl-5,6-dihydro-4H-[1,3]oxazin-2-ylamine (intermediate A8.2) and 5-difluoromethyl-pyrazine-2-carboxylic acid (CAS 1174321-06-2, US2009209757) following procedure I yielded the title compound as a light yellow solid. MS (ISP): m/z=398.2 [M+H]$^+$.

Example 16

5-Cyclopropylmethoxy-pyrazine-2-carboxylic acid [3-((4R,5R)-2-amino-5-fluoro-4-methyl-5,6-dihydro-4H-[1,3]oxazin-4-yl)-4-fluoro-phenyl]-amide The condensation of (4R,5R)-4-(5-amino-2-fluoro-phenyl)-5-fluoro-4-methyl-5,6-dihydro-4H-[1,3]oxazin-2-ylamine (intermediate A8.2) and 5-cyclopropylmethoxypyrazine-2-carboxylic acid following procedure I yielded the title compound as a white solid. MS (ISP): m/z=418.3 [M+H]⁺.

The 5-cyclopropylmethoxy-pyrazine-2-carboxylic acid was obtained following the general procedure below:

A solution of 5-chloro-pyrazine-2-carboxylic acid (1.50 g, 9.46 mmol) in dry dimethylsulfoxide (5 ml) was treated at 25° C. with cyclopropyl-methanol (1.02 g, 14.1 mmol) and powdered potassium hydroxide (2.12 g, 37.4 mmol). The mixture was heated in a microwave oven at 80° C. for 90 minutes. For the workup, the reaction mixture was quenched with an aqueous solution of citric acid (10%), then extracted with ethyl acetate (5×30 ml), followed by the extraction with a 4:1-mixture of dichloromethane and methanol. The combined organic layers were washed with brine (200 ml), dried and evaporated at reduced pressure. After lyophilization the 5-cyclopropylmethoxy-pyrazine-2-carboxylic acid (34% yield) was obtained as a white solid. MS (ISP): m/z=195.0 [M+H]⁺.

Example 17

5-(2,2,2-Trifluoro-ethoxy)-pyridine-2-carboxylic acid [3-((4R,5R)-2-amino-5-fluoro-4-methyl-5,6-dihydro-4H-[1,3]oxazin-4-yl)-4-fluoro-phenyl]-amide The condensation of (4R,5R)-4-(5-amino-2-fluoro-phenyl)-5-fluoro-4-methyl-5,6-dihydro-4H-[1,3]oxazin-2-ylamine (intermediate A8.2) and 5-(2,2,2-trifluoro-ethoxy)-pyridine-2-carboxylic acid following procedure I yielded the title compound as a white solid. MS (ISP): m/z=445.3 [M+H]⁺.

The 5-(2,2,2-trifluoro-ethoxy)-pyridine-2-carboxylic acid was obtained as follows:

a) 5-(2,2,2-Trifluoro-ethoxy)-pyridine-2-carboxylic acid methyl ester

Under an atmosphere of nitrogen a solution of 5-hydroxy-pyridine-2-carboxylic acid methyl ester (200 mg, 1.31 mmol) in N,N-dimethylformamide (2 ml) was treated at room temperature with sodium hydride (55% dispersion in oil, 64 mg). After the gas formation had ceased, the suspension was cooled to 0° C. and trifluoro-methanesulphonic acid 2,2,2-trifluoro-ethyl ester (364 mg, 1.57 mmol) was added. After stirring at room temperature for 2 hours about 50% of the starting material was left. Another 364 mg of trifluoro-methanesulphonic acid 2,2,2-trifluoro-ethyl ester were added and after 30 minutes the reaction was complete. For the workup, the reaction mixture was treated with a saturated solution of sodium carbonate, then extracted with ethyl acetate (3×). The combined organic layers were washed with brine, dried over sodium sulphate, and evaporated at reduced pressure. The crude product was purified by chromatography on silica gel using a 3:1-mixture of heptane and ethyl acetate as the eluent. The 5-(2,2,2-trifluoro-ethoxy)-pyridine-2-carboxylic acid methyl ester was obtained as a white solid (216 mg, 70% of theory). MS (ISP): m/z=236.3 [M+H]⁺.

b) 5-(2,2,2-Trifluoro-ethoxy)-pyridine-2-carboxylic acid

Under an atmosphere of nitrogen a solution of 5-(2,2,2-trifluoro-ethoxy)-pyridine-2-carboxylic acid methyl ester (216 mg, 0.92 mmol) in methanol (1 ml) was treated with a solution of lithium hydroxide monohydrate (78 mg, 1.84 mmol) in methanol (0.1 ml). After stirring for 2 hours the reaction mixture was evaporated at reduced pressure. The residue was treated with hydrochloric acid (1N), the solid material was filtered then washed with water, finally dried at high vacuum. The 5-(2,2,2-trifluoro-ethoxy)-pyridine-2-carboxylic acid was obtained as a white solid (125 mg, 61% of theory).

Example 18

2,5-Dimethyl-furan-3-carboxylic acid [3-((4R,5R)-2-amino-5-fluoro-4-methyl-5,6-dihydro-4H-[1,3]oxazin-4-yl)-4-fluoro-phenyl]-amide The condensation of (4R,5R)-4-(5-amino-2-fluoro-phenyl)-5-fluoro-4-methyl-5,6-dihydro-4H-[1,3]oxazin-2-ylamine (intermediate A8.2) and 2,5-dimethyl-furan-3-carboxylic acid (CAS 636-44-2) following procedure I yielded the title compound as a white solid. MS (ISP): m/z=364.3 [M+H]*.

Example 19

5-(2,2-Difluoro-ethoxy)-pyrazine-2-carboxylic acid [3-((4R,5R)-2-amino-5-fluoro-4-methyl-5,6-dihydro-4H-[1,3]oxazin-4-yl)-4-fluoro-phenyl]-amide The condensation of (4R,5R)-4-(5-amino-2-fluoro-phenyl)-5-fluoro-4-methyl-5,6-dihydro-4H-[1,3]oxazin-2-ylamine (intermediate A8.2) and 5-(2,2-difluoro-ethoxy)-pyrazine-2-carboxylic acid (CAS 1174323-38-6; WO2009091016) following procedure I yielded the title compound as a white solid. MS (ISP): m/z=428.2 [M+H]⁺.

Example 20

5-Fluoro-pyridine-2-carboxylic acid [3-((4R,5R)-2-amino-5-fluoro-4-methyl-5,6-dihydro-4H-[1,3]oxazin-4-yl)-4-fluoro-phenyl]-amide The condensation of (4R,5R)-4-(5-amino-2-fluoro-phenyl)-5-fluoro-4-methyl-5,6-dihydro-4H-[1,3]oxazin-2-ylamine (intermediate A8.2) and 5-fluoro-pyridine-2-carboxylic acid following procedure I yielded the title compound as a white solid. MS (ISP): m/z=365.2 [M+H]⁺.

Example 21

5-(2,2-Difluoro-ethoxy)-pyridine-2-carboxylic acid [3-((4R,5R)-2-amino-5-fluoro-4-methyl-5,6-dihydro-4H-[1,3]oxazin-4-yl)-4-fluoro-phenyl]-amide The condensation of (4R,5R)-4-(5-amino-2-fluoro-phenyl)-5-fluoro-4-methyl-5,6-dihydro-4H-[1,3]oxazin-2-ylamine (intermediate A8.2) and 5-(2,2-difluoro-ethoxy)-pyridine-2-carboxylic acid (CAS 1097730-45-4; WO2009091016) following procedure I yielded the title compound as a white foam. MS (ISP): m/z=427.2 [M+H]⁺.

Example 22

5-Cyclopropyl-pyridine-2-carboxylic acid [3-((4R,5R)-2-amino-5-fluoro-4-methyl-5,6-dihydro-4H-[1,3]oxazin-4-yl)-4-fluoro-phenyl]-amide The condensation of (4R,5R)-4-(5-amino-2-fluoro-phenyl)-5-fluoro-4-methyl-5,6-dihydro-4H-[1,3]oxazin-2-ylamine (intermediate A8.2) and 5-cyclopropyl-pyridine-2- carboxylic acid (CAS 1174322-66-7; WO2009091016) following procedure I yielded the title compound as a white solid. MS (ISP): m/z=387.3 [M+H]$^+$.

Example 23

5-Cyclopropylmethoxy-pyridine-2-carboxylic acid [3-((4R,5R)-2-amino-5-fluoro-4-methyl-5,6-dihydro-4H-[1,3]oxazin-4-yl)-4-fluoro-phenyl]-amide The condensation of (4R,5R)-4-(5-amino-2-fluoro-phenyl)-5-fluoro-4-methyl-5,6-dihydro-4H-[1,3]oxazin-2-ylamine (intermediate A8.2) and 5-cyclopropylmethoxy-pyridine-2-carboxylic acid following procedure I yielded the title compound as a white foam. MS (ISP): m/z=417.3 [M+H]$^+$.

The 5-cyclopropylmethoxy-pyridine-2-carboxylic acid was prepared in a manner analogous to that described for the preparation of 5-cyclopropylmethoxy-pyrazine-2-carboxylic acid (Example 16) at 100° C. for 90 minutes in a microwave oven. The 5-cyclopropylmethoxy-pyridine-2-carboxylic acid (25% yield) was obtained as an off-white solid. MS (ISP): m/z=194.0 [M+H]$^+$.

Example 24

5-(2,2,3,3-Tetrafluoro-propoxy)-pyridine-2-carboxylic acid [3-((4R,5R)-2-amino-5-fluoro-4-methyl-5,6-dihydro-4H-[1,3]oxazin-4-yl)-4-fluoro-phenyl]-amide The condensation of (4R,5R)-4-(5-amino-2-fluoro-phenyl)-5-fluoro-4-methyl-5,6-dihydro-4H-[1,3]oxazin-2-ylamine (intermediate A8.2) and 5-(2,2,3,3-tetrafluoro-propoxy)-pyridine-2-carboxylic acid following procedure I yielded the title compound as a white foam. MS (ISP): m/z=477.1 [M+H]$^+$.

The 5-(2,2,3,3-tetrafluoro-propoxy)-pyridine-2-carboxylic acid was prepared as follows:

a) 5-(2,2,3,3-Tetrafluoro-propoxy)-pyridine-2-carboxylic acid methyl ester

A solution of 5-hydroxy-pyridine-2-carboxylic acid methyl ester (2.0 g, 13.1 mmol) in acetone (40 ml) was treated with potassium carbonate (5.415 g, 39.2 mmol) and trifluoromethanesulphonic acid 2,2,3,3-tetrafluoropropyl ester. After 4 hours stirring at room temperature the suspension was diluted with diethylether. After filtration the solution was evaporated and the yellow solid purified by chromatography on silica gel using a gradient of heptane/ethyl acetate=100:0 to 30:70 as the eluent. The 5-(2,2,3,3-tetrafluoro-propoxy)-pyridine-2-carboxylic acid methyl ester was obtained as a light yellow solid (3.49 g, 76% of theory). MS (ISP): m/z=468.1 [M+H]$^+$.

b) 5-(2,2,3,3-Tetrafluoro-propoxy)-pyridine-2-carboxylic acid

In a manner analogous to that described in example 17b), the hydrolysis of the 5-(2,2,3,3-tetrafluoro-propoxy)-pyridine-2-carboxylic acid methyl ester with lithium hydroxide yielded the title compound as a light yellow solid (yield 94% of theory). MS (ISP): m/z=253 [M]$^+$.

Example 25

5-(2,2,3,3,3-Pentafluoro-propoxy)-pyridine-2-carboxylic acid [3-((4R,5R)-2-amino-5-fluoro-4-methyl-5,6-dihydro-4H-[1,3]oxazin-4-yl)-4-fluoro-phenyl]-amide The condensation of (4R,5R)-4-(5-amino-2-fluoro-phenyl)-5-fluoro-4-methyl-5,6-dihydro-4H-[1,3]oxazin-2-ylamine (intermediate A8.2) and 5-(2,2,3,3,3-pentafluoro-propoxy)-pyridine-2-carboxylic acid following procedure I yielded the title compound as a white foam. MS (ISP): m/z=495.2 [M+H]$^+$.

The 5-(2,2,3,3,3-pentafluoro-propoxy)-pyridine-2-carboxylic acid was obtained as follows:

a) In a manner analogous to that described in example 24 a), the alkylation of the 5-hydroxy-pyridine-2-carboxylic acid methyl ester with potassium carbonate and trifluoromethanesulphonic acid 2,2,3,3,3-pentafluoropropyl ester yielded the 5-(2,2,3,3,3-pentafluoro-propoxy)-pyridine-2-carboxylic acid methyl ester as a light yellow oil. MS (ISP): m/z=285 [M]$^+$.

b) In a manner analogous to that described in example 17b), the hydrolysis of the 5-(2,2,3,3,3-pentafluoro-propoxy)-pyridine-2-carboxylic acid methyl ester with lithium hydroxide yielded the 5-(2,2,3,3,3-pentafluoro-propoxy)-pyridine-2-carboxylic acid as a white solid. MS (ISP): m/z=271 [M+H]$^+$.

Example 26

2-Chloro-thiazole-5-carboxylic acid [3-((4R,5R)-2-amino-5-fluoro-4-methyl-5,6-dihydro-4H-[1,3]oxazin-4-yl)-4-fluoro-phenyl]-amide The condensation of (4R,5R)-4-(5-amino-2-fluoro-phenyl)-5-fluoro-4-methyl-5,6-dihydro-4H-[1,3]oxazin-2-ylamine (intermediate A8.2) and 2-chloro-thiazole-5-carboxylic acid (CAS 101012-12-8) following procedure I yielded the title compound as a white solid. MS (ISP): m/z=387.2 [M+H]$^+$.

Example 27

2-Methyl-5-trifluoromethyl-2H-pyrazole-3-carboxylic acid [3-((4R,5R)-2-amino-5-fluoro-4-methyl-5,6-dihydro-4H-[1,3]oxazin-4-yl)-4-fluoro-phenyl]-amide The condensation of (4R,5R)-4-(5-amino-2-fluoro-phenyl)-5-fluoro-4-methyl-5,6-dihydro-4H-[1,3]oxazin-2-ylamine (intermediate A8.2) and 2-methyl-5-trifluoromethyl-2H-pyrazole-3-carboxylic acid (CAS 128694-63-3) following procedure I yielded the title compound as a white solid. MS (ISP): m/z=418.3 [M+H]$^+$.

Example 28

4-Chloro-1H-pyrazole-3-carboxylic acid [3-((4R,5R)-2-amino-5-fluoro-4-methyl-5,6-dihydro-4H-[1,3]oxazin-4-yl)-4-fluoro-phenyl]-amide The condensation of (4R,5R)-4-(5-amino-2-fluoro-phenyl)-5-fluoro-4-methyl-5,6-dihydro-4H-[1,3]oxazin-2-ylamine (intermediate A8.2) and 4-chloro-1H-pyrazole-3-

Example 29

Thiazole-5-carboxylic acid [3-((4R,5R)-2-amino-5-fluoro-4-methyl-5,6-dihydro-4H-[1,3]oxazin-4-yl)-4-fluoro-phenyl]-amide The condensation of (4R,5R)-4-(5-amino-2-fluoro-phenyl)-5-fluoro-4-methyl-5,6-dihydro-4H-[1,3]oxazin-2-ylamine (intermediate A8.2) and thiazole-5-carboxylic acid (CAS 14527-41-4) following procedure I yielded the title compound as a white solid. MS (ISP): m/z=353.2 [M+H]$^+$.

Example 30

1,5-Dimethyl-1H-pyrazole-3-carboxylic acid [3-((4R,5R)-2-amino-5-fluoro-4-methyl-5,6-dihydro-4H-[1,3]oxazin-4-yl)-4-fluoro-phenyl]-amide The condensation of (4R,5R)-4-(5-amino-2-fluoro-phenyl)-5-fluoro-4-methyl-5,6-dihydro-4H-[1,3]oxazin-2-ylamine (intermediate A8.2) and 1,5-dimethyl-1H-pyrazole-3-carboxylic acid (CAS 5744-59-2) following procedure I yielded the title compound as a white solid. MS (ISP): m/z=364.3 [M+H]$^+$

Example 31

1-Cyano-cyclopropanecarboxylic acid [3-((4R,5R)-2-amino-5-fluoro-4-methyl-5,6-dihydro-4H-[1,3]oxazin-4-yl)-4-fluoro-phenyl]-amide The condensation of (4R,5R)-4-(5-amino-2-fluoro-phenyl)-5-fluoro-4-methyl-5,6-dihydro-4H-[1,3]oxazin-2-ylamine (intermediate A8.2) and 1-cyano-cyclopropanecarboxylic acid (CAS 6914-79-0) following procedure I yielded the title compound as a white foam. MS (ISP): m/z=335.3 [M+H]$^+$.

Example 32

Cyclopropanecarboxylic acid [3-((4R,5R)-2-amino-5-fluoro-4-methyl-5,6-dihydro-4H-[1,3]oxazin-4-yl)-4-fluoro-phenyl]-amide The condensation of (4R,5R)-4-(5-amino-2-fluoro-phenyl)-5-fluoro-4-methyl-5,6-dihydro-4H-[1,3]oxazin-2-ylamine (intermediate A8.2) and cyclopropanecarboxylic acid following procedure I yielded the title compound as a white foam. MS (ISP): m/z=310.2 [M+H]$^+$.

Example 33

5-Cyano-pyridine-2-carboxylic acid [3-((4R,5S)-2-amino-5-fluoro-4-methyl-5,6-dihydro-4H-[1,3]oxazin-4-yl)-4-fluoro-phenyl]-amide The condensation of (4R,5S)-4-(5-amino-2-fluoro-phenyl)-5-fluoro-4-methyl-5,6-dihydro-4H-[1,3]oxazin-2-ylamine (intermediate A8.1) and 5-cyano-pyridine-2-carboxylic acid following procedure I yielded the title compound as a white solid. MS (ISP): m/z=372.2 [M+H]$^+$.

Example 34

5-Chloro-pyridine-2-carboxylic acid [3-((4R,5S)-2-amino-5-fluoro-4-methyl-5,6-dihydro-4H-[1,3]oxazin-4-yl)-4-fluoro-phenyl]-amide The condensation of (4R,5S)-4-(5-amino-2-fluoro-phenyl)-5-fluoro-4-methyl-5,6-dihydro-4H-[1,3]oxazin-2-ylamine (intermediate A8.1) and 5-chloro-pyridine-2-carboxylic acid following procedure I yielded the title compound as a white solid. MS (ISP): m/z=381.1 [M+H]$^+$.

Example 35

3-Chloro-5-cyano-pyridine-2-carboxylic acid [3-((4R,5S)-2-amino-5-fluoro-4-methyl-5,6-dihydro-4H-[1,3]oxazin-4-yl)-4-fluoro-phenyl]-amide The condensation of (4R,5S)-4-(5-amino-2-fluoro-phenyl)-5-fluoro-4-methyl-5,6-dihydro-4H-[1,3]oxazin-2-ylamine (intermediate A8.1) and 3-chloro-5-cyano-pyridine-2-carboxylic acid following procedure I yielded the title compound as an off-white foam. MS (ISP): m/z=406.2 [M+H]$^+$.

Example 36

3-Chloro-5-trifluoromethyl-pyridine-2-carboxylic acid [3-((4R,5S)-2-amino-5-fluoro-4-methyl-5,6-dihydro-4H-[1,3]oxazin-4-yl)-4-fluoro-phenyl]-amide The condensation of (4R,5S)-4-(5-amino-2-fluoro-phenyl)-5-fluoro-4-methyl-5,6-dihydro-4H-[1,3]oxazin-2-ylamine (intermediate A8.1) and 3-chloro-5-trifluoromethyl-pyridine-2-carboxylic acid following procedure I yielded the title compound as a white solid. MS (ISP): m/z=449.2 [M+H]$^+$.

Example 37

3-(2,2,2-Trifluoro-ethoxy)-pyridine-2-carboxylic acid [3-((4R,5R)-2-amino-5-fluoro-4,5-dimethyl-5,6-dihydro-4H-[1,3]oxazin-4-yl)-4-fluoro-phenyl]-amide The condensation of (4R,5R)-4-(5-amino-2-fluoro-phenyl)-5-fluoro-4,5-dimethyl-5,6-dihydro-4H-[1,3]oxazin-2-ylamine (A8.3) and 3-(2,2,2-trifluoro-ethoxy)-pyridine-2-carboxylic (CAS 1250130-41-6; acid following procedure I yielded the title compound as a white solid. MS (ISP): m/z=459.2 [M+H]$^+$.

The 3-(2,2,2-trifluoro-ethoxy)-pyridine-2-carboxylic acid was prepared as follows:

a) To a solution of 3-hydroxy-pyridine-2-carboxylic acid methyl ester (200 mg, 1.3 mmol) in N,N-dimethylformamide (2.0 ml) was added at 22° C. sodium hydride (55% in oil, 64 mg) and stirring was continued until gas evolution ceased. The suspension was cooled to 0° C. and treated with trifluoroethyl trifluoromethanesulfonate (728 mg) and stirring was continued at 22° C. for 2 hours. The mixture was partitioned between saturated sodium hydrogen-carbonate solution and ethyl acetate, and the organic layer was dried and evaporated. The residue was purified by chromatography on silica using n-heptane and ethyl acetate (3:1) as the eluent to give 3-(2,2,2-trifluoro-ethoxy)-pyridine-2-carboxylic acid methyl ester as a pale green oil. MS (ISP): m/z=236 [M+H]$^+$.

b) A solution of 3-(2,2,2-trifluoro-ethoxy)-pyridine-2-carboxylic acid methyl ester (216 mg, 0.9 mmol) in methanol (1 ml) was treated with a solution of lithium hydroxide (78 mg, 3.3 mmol) in water (0.1 ml) and stirring was continued at 22° C. for 2 hours. The solution was evaporated and the residue triturated with 1N aqueous hydrochloric acid. The suspension was filtered, the residue washed with water and dried to give 3-(2,2,2-trifluoro-ethoxy)-pyridine-2-carboxylic acid as a colorless solid. MS (ISN): m/z=220 [M−H]⁻.

Example 38

5-Cyano-pyridine-2-carboxylic acid [3-((4R,5R)-2-amino-5-fluoro-4,5-dimethyl-5,6-dihydro-4H-[1,3]oxazin-4-yl)-4-fluoro-phenyl]-amide The condensation of (4R,5R)-4-(5-amino-2-fluoro-phenyl)-5-fluoro-4,5-dimethyl-5,6-dihydro-4H-[1,3]oxazin-2-ylamine (A8.3) and 5-cyano-pyridine-2-carboxylic acid following procedure I yielded the title compound as a colorless solid. MS (ISP): m/z=386.2 [M+H]⁺.

Example 39

3,5-Dichloro-pyridine-2-carboxylic acid [3-((4R,5R)-2-amino-5-fluoro-4,5-dimethyl-5,6-dihydro-4H-[1,3]oxazin-4-yl)-4-fluoro-phenyl]-amide The condensation of (4R,5R)-4-(5-amino-2-fluoro-phenyl)-5-fluoro-4,5-dimethyl-5,6-dihydro-4H-[1,3]oxazin-2-ylamine (A8.3) and 3,5-dichloro-pyridine-2-carboxylic acid following procedure I yielded the title compound as a colorless solid. MS (ISP): m/z=429.2[M+H]⁺ and 431.1 [M+2+H]⁺.

Example 40

4-Chloro-1-difluoromethyl-1H-pyrazole-3-carboxylic acid [3-((4R,5R)-2-amino-5-fluoro-4,5-dimethyl-5,6-dihydro-4H-[1,3]oxazin-4-yl)-4-fluoro-phenyl]amide The condensation of (4R,5R)-4-(5-amino-2-fluoro-phenyl)-5-fluoro-4,5-dimethyl-5,6-dihydro-4H-[1,3]oxazin-2-ylamine (A8.3) and 4-chloro-1-difluoromethyl-1H-pyrazole-3-carboxylic acid following procedure I yielded the title compound as a white solid. MS (ISP): m/z=434.2 [M+H]⁺.

The 4-chloro-1-difluoromethyl-1H-pyrazole-3-carboxylic acid was obtained as follows:

a) 1-Difluoromethyl-1H-pyrazole-3-carboxylic acid methyl ester

A solution of 1-difluoromethyl-1H-pyrazole-3-carboxylic acid (CAS 925179-02-8) (500 mg, 3.1 mmol) in methanol (18 ml) was cooled to 0° C. and treated with sulphuric acid (98%, 0.2 ml, 3.1 mmol). The mixture was heated to reflux for 2 hours. For the workup, the solution was cooled and concentrated at reduced pressure. The residue was partitioned between ethyl acetate (25 ml) and water (30 ml). The organic layer was separated, washed with water until the water phase showed a neutral pH. After drying over sodium sulphate, the organic layer was evaporated at reduced pressure. The 1-difluoromethyl-1H-pyrazole-3-carboxylic acid methyl ester was obtained as a colorless liquid (535 mg, 99% of theory) pure enough to be engaged in the next step without further purification. MS (ISP): m/z=177.1 [M+H]⁺.

b)
4-Chloro-1-difluoromethyl-1H-pyrazole-3-carboxylic acid methyl ester

A mixture of 1-difluoromethyl-1H-pyrazole-3-carboxylic acid methyl ester (535 mg, 3 mmol) and N-chloro-succinimide (1.22 g, 9.1 mmol) in N,N-dimethylformamide (5 ml) was heated at 50° C. overnight. The reaction mixture was cooled, poured into water (20 ml), then extracted with ethyl acetate. The organic layer was separated, washed with water, dried over sodium sulphate, finally evaporated at reduced pressure. The yellowish crude material was purified by chromatography on silica gel using a 3:1-mixture of cyclohexane and ethyl acetate as the eluent. The 4-chloro-1-difluoromethyl-1H-pyrazole-3-carboxylic acid methyl ester was obtained as a white solid (540 mg, 84% of theory). MS (ISP): m/z=209.9 [M]⁺.

c)
4-Chloro-1-difluoromethyl-1H-pyrazole-3-carboxylic acid

A solution of 4-chloro-1-difluoromethyl-1H-pyrazole-3-carboxylic acid methyl ester (540 mg, 2.6 mmol) in tetrahydrofuran (18 ml) was treated at room temperature with a solution of lithium hydroxide (135 mg, 5.6 mmol) in a 1:1-mixture of water and methanol (12 ml). After 1 hour the reaction was complete, and the solvents were evaporated at reduced pressure. The residue was dissolved in water (10 ml) and acidified with hydrochloric acid (2M). Extraction with ethyl acetate, drying of the organic layer over sodium sulphate, and evaporation at reduced pressure yielded a white solid (555 mg) which was triturated with pentane (10 ml). The solid material was filtered, washed with pentane and dried. After drying at reduced pressure the 4-chloro-1-difluoromethyl-1H-pyrazole-3-carboxylic acid was obtained as a white solid (477 mg, 95% of theory). MS (ISP): m/z=195.0 [M−H]⁻.

Example 41

5-Chloro-pyridine-2-carboxylic acid [3-((4R,5R)-2-amino-5-fluoro-4,5-dimethyl-5,6-dihydro-4H-[1,3]oxazin-4-yl)-4-fluoro-phenyl]-amide The condensation of (4R,5R)-4-(5-amino-2-fluoro-phenyl)-5-fluoro-4,5-dimethyl-5,6-dihydro-4H-[1,3]oxazin-2-ylamine (A8.3) and 5-chloro-pyridine-2-carboxylic acid following procedure I yielded the title compound as a colorless solid. MS (ISP): m/z=395.1 [M+H]⁺.

Example 42

5-Fluoro-pyridine-2-carboxylic acid [3-((4R,5R)-2-amino-5-fluoro-4,5-dimethyl-5,6-dihydro-4H-[1,3]oxazin-4-yl)-4-fluoro-phenyl]-amide The condensation of (4R,5R)-4-(5-amino-2-fluoro-phenyl)-5-fluoro-4,5-dimethyl-5,6-dihydro-4H-[1,3]oxazin-2-ylamine (A8.3) and 5-fluoro-pyridine-2-carboxylic acid following procedure I yielded the title compound as a colorless solid. MS (ISP): m/z=379.3 [M+H]⁺.

Example 43

4-Chloro-1-(2,2-difluoro-ethyl)-1H-pyrazole-3-carboxylic acid [3-((4R,5R)-2-amino-5-fluoro-4,5-dimethyl-5,6-dihydro-4H-[1,3]oxazin-4-yl)-4-fluoro-phenyl]amide The condensation of (4R,5R)-4-(5-amino-2-fluoro-phenyl)-5-fluoro-4,5-dimethyl-5,6-dihydro-4H-[1,3]oxazin-2-ylamine (A8.3) and 4-chloro-1-(2,2-difluoro-ethyl)-1H-pyrazole-3-carboxylic acid (CAS 1006486-42-5) following procedure I yielded the title compound as a white solid. MS (ISP): m/z=448.2 [M+H]$^+$.

Example 44

2,2-Difluoro-cyclopropanecarboxylic acid [3-((4R,5R)-2-amino-5-fluoro-4,5-dimethyl-5,6-dihydro-4H-[1,3]oxazin-4-yl)-4-fluoro-phenyl]-amide The condensation of (4R,5R)-4-(5-amino-2-fluoro-phenyl)-5-fluoro-4,5-dimethyl-5,6-dihydro-4H-[1,3]oxazin-2-ylamine (A8.3) and 2,2-difluoro-cyclopropanecarboxylic acid (CAS 107873-03-0) following procedure I yielded the title compound as a white solid. MS (ISP): m/z=360.3 [M+H]$^+$.

Example 45

5-Chloro-pyridine-2-carboxylic acid {3-[(4R,5R)-2-amino-4-methyl-5-(2,2,2-trifluoro-ethoxy)-5,6-dihydro-4H-[1,3]oxazin-4-yl]-4-fluoro-phenyl}-amide The condensation of (4R,5R)-4-(5-amino-2-fluoro-phenyl)-4-methyl-5-(2,2,2-trifluoro-ethoxy)-5,6-dihydro-4H-[1,3]oxazin-2-ylamine (A8.4) and 5-chloro-pyridine-2-carboxylic acid following procedure I yielded the title compound as a white solid. MS (ISP): m/z=461.2 [M+H]$^+$.

Example 46

5-Fluoro-pyridine-2-carboxylic acid {3-[(4R,5R)-2-amino-4-methyl-5-(2,2,2-trifluoro-ethoxy)-5,6-dihydro-4H-[1,3]oxazin-4-yl]-4-fluoro-phenyl}-amide The condensation of (4R,5R)-4-(5-amino-2-fluoro-phenyl)-4-methyl-5-(2,2,2-trifluoro-ethoxy)-5,6-dihydro-4H-[1,3]oxazin-2-ylamine (A8.4) and 5-fluoro-pyridine-2-carboxylic acid following procedure I yielded the title compound as a white solid. MS (ISP): m/z=445.3 [M+H]$^+$.

Example 47

5-Cyano-pyridine-2-carboxylic acid {3-[(4R,5R)-2-amino-4-methyl-5-(2,2,2-trifluoro-ethoxy)-5,6-dihydro-4H-[1,3]oxazin-4-yl]-4-fluoro-phenyl}-amide The condensation of (4R,5R)-4-(5-amino-2-fluoro-phenyl)-4-methyl-5-(2,2,2-trifluoro-ethoxy)-5,6-dihydro-4H-[1,3]oxazin-2-ylamine (A8.4) and 5-cyano-pyridine-2-carboxylic acid following procedure I yielded the title compound as a white solid. MS (ISP): m/z=452.1 [M+H]$^-$.

Example 48

3,5-Dichloro-pyridine-2-carboxylic acid {3-[(4R,5R)-2-amino-4-methyl-5-(2,2,2-trifluoro-ethoxy)-5,6-dihydro-4H-[1,3]oxazin-4-yl]-4-fluoro-phenyl}-amide The condensation of (4R,5R)-4-(5-amino-2-fluoro-phenyl)-4-methyl-5-(2,2,2-trifluoro-ethoxy)-5,6-dihydro-4H-[1,3]oxazin-2-ylamine (A8.4) and 3,5-dichloro-pyridine-2-carboxylic acid following procedure I yielded the title compound as a white solid. MS (ISP): m/z=495.1 [M+H]$^+$ and 497.2 [M+2+H]$^+$.

Example 49

5-(2,2,2-Trifluoro-ethoxy)-pyridine-2-carboxylic acid {3-[(4R,5R)-2-amino-4-methyl-5-(2,2,2-trifluoro-ethoxy)-5,6-dihydro-4H-[1,3]oxazin-4-yl]-4-fluoro-phenyl}-amide The condensation of (4R,5R)-4-(5-amino-2-fluoro-phenyl)-4-methyl-5-(2,2,2-trifluoro-ethoxy)-5,6-dihydro-4H-[1,3]oxazin-2-ylamine (A8.4) and 5-(2,2,2-trifluoro-ethoxy)-pyridine-2-carboxylic acid following procedure I yielded the title compound as a white solid. MS (ISP): m/z=525.2.

Example 50

5-But-2-ynyloxy-pyrazine-2-carboxylic acid [3-((4R,5R)-2-amino-5-fluoro-4,5-dimethyl-5,6-dihydro-4H-[1,3]oxazin-4-yl)-4-fluoro-phenyl]-amide The condensation of (4R,5R)-4-(5-amino-2-fluoro-phenyl)-5-fluoro-4,5-dimethyl-5,6-dihydro-4H-[1,3]oxazin-2-ylamine (A8.3) and 5-but-2-ynyloxy-pyridine-2-carboxylic acid (prepared as described in Tamura Y. et al., WO 2010/113 848) following procedure I yielded the title compound as a white solid. MS (ISP): m/z=430.3 [M+H]$^+$.

Example 51

5-Cyano-pyridine-2-carboxylic acid [3-((4S,5R)-2-amino-5-fluoro-4-fluoromethyl-5,6-dihydro-4H-[1,3]oxazin-4-yl)-4-fluoro-phenyl]-amide The condensation of (4S,5R)-4-(5-amino-2-fluoro-phenyl)-5-fluoro-4-fluoromethyl-5,6-dihydro-4H-[1,3]oxazin-2-ylamine (A8.5) and 5-cyano-pyridine-2-carboxylic acid following procedure I yielded the title compound as a light yellow solid. MS (ISP): m/z=390.2 [M+H]$^+$.

Example 52

5-Cyano-pyridine-2-carboxylic acid [3-((4S,5S)-2-amino-5-fluoro-4-fluoromethyl-5,6-dihydro-4H-[1,3]oxazin-4-yl)-4-fluoro-phenyl]-amide The condensation of (4S,5S)-4-(5-amino-2-fluoro-phenyl)-5-fluoro-4-fluoromethyl-5,6-dihydro-4H-[1,3]oxazin-2-ylamine (A8.6) and 5-cyano-pyridine-2-carboxylic acid following procedure I yielded the title compound as a white solid. MS (ISP): m/z=390.4 [M+H]+.

Example 53

5-Cyano-pyridine-2-carboxylic acid [3-((4R,5R)- or (4R,5S)-2-amino-4-difluoromethyl-5-fluoro-5,6-dihydro-4H-[1,3]oxazin-4-yl)-4-fluoro-phenyl]-amide The condensation of (4R,5R)- and (4R,5S)-4-(5-amino-2-fluoro-phenyl)-4-difluoromethyl-5-fluoro-5,6-dihydro-4H-[1,3]oxazin-2-ylamine and 5-cyano-pyridine-2-carboxylic acid following procedure I yielded the title compound as a white solid. MS (ISP): m/z=408.4 [M+H]+. The minor isomer was not isolated.

The invention claimed is:
1. A compound of formula I,

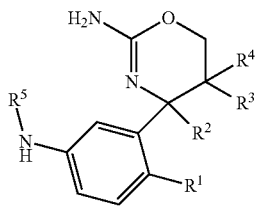

I wherein
R$^1$ is selected from the group consisting of
  hydrogen,
  halogen, and
  C$_{1-6}$-alkyl;
R$^2$ is selected from the group consisting of
  hydrogen,
  C$_{1-6}$-alkyl, and
  halogen-C$_{1-3}$-alkyl;
R$^3$ is selected from the group consisting of
  hydrogen and
  C$_{1-6}$-alkyl;
R$^4$ is selected from the group consisting of
  halogen,
  C$_{1-6}$-alkyl, and
  halogen-C$_{1-6}$-alkoxy;
R$^5$ is —C(=O)—R$^6$; and
R$^6$ is selected from the group consisting of
  heteroaryl,
  heteroaryl substituted by 1-4 substituents individually selected from cyano, cyano-C$_{1-6}$-alkyl, halogen, halogen-C$_{1-6}$-alkoxy, halogen-C$_{1-6}$-alkyl, C$_{1-6}$-alkoxy, C$_{1-6}$-alkoxy-C$_{1-6}$-alkyl, C$_{3-6}$-cycloalkyl, C$_{3-6}$-cycloalkyl-C$_{1-6}$-alkoxy, C$_{3-6}$-cycloalkyl-C$_{1-6}$-alkyl, C$_{3-6}$-cycloalkyl-C$_{2-6}$-alkynyl, C$_{2-6}$-alkynyl-C$_{1-6}$-alkoxy and C$_{1-6}$-alkyl,
  C$_{3-6}$-cycloalkyl,
  C$_{3-6}$-cycloalkyl substituted by 1-4 substituents individually selected from cyano, cyano-C$_{1-6}$-alkyl, halogen, halogen-C$_{1-6}$-alkoxy, halogen-C$_{1-6}$-alkyl, hydroxy, C$_{1-6}$-alkoxy, C$_{1-6}$-alkoxy-C$_{1-6}$-alkyl and C$_{1-6}$-alkyl,
  heterocyclyl, and
  heterocyclyl substituted by 1-4 substituents individually selected from cyano, cyano-C$_{1-6}$-alkyl, halogen, halogen-C$_{1-6}$-alkoxy, halogen-C$_{1-6}$-alkyl, C$_{1-6}$-alkoxy, C$_{1-6}$-alkoxy-C$_{1-6}$-alkyl and C$_{1-6}$-alkyl;
or a pharmaceutically acceptable salt thereof.

2. The compound of claim 1, having formula Ia,

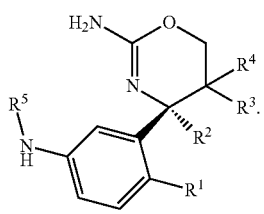

Ia

3. The compound of claim 1, wherein
R$^1$ is halogen;
R$^2$ is C$_{1-6}$-alkyl;
R$^3$ is selected from the group consisting of
  hydrogen and
  C$_{1-6}$-alkyl;
R$^4$ is selected from the group consisting of
  halogen and
  halogen-C$_{1-6}$-alkoxy;
R$^5$ is —C(=O)—R$^6$; and
R$^6$ is selected from the group consisting of
  heteroaryl,
  heteroaryl substituted by 1-4 substituents individually selected from cyano, halogen, halogen-C$_{1-6}$-alkoxy, halogen-C$_{1-6}$-alkyl, C$_{1-6}$-alkoxy, C$_{1-6}$-alkyl, C$_{3-6}$-cycloalkyl, C$_{3-6}$-cycloalkyl-C$_{1-6}$-alkoxy, C$_{2-6}$-alkynyl-C$_{1-6}$-alkoxy and C$_{3-6}$-cycloalkyl-C$_{2-6}$-alkynyl,
  C$_{3-6}$-cycloalkyl, and
  C$_{3-6}$-cycloalkyl substituted by 1-4 substituents individually selected from cyano and halogen,
or a pharmaceutically acceptable salt thereof.

4. The compound of claim 1, wherein R$^1$ is halogen.
5. The compound of claim 4, wherein R$^1$ is F.
6. The compound of claim 1, wherein R$^2$ is C$_{1-6}$-alkyl.
7. The compound of claim 6, wherein R$^2$ is Me.
8. The compound of claim 1, wherein R$^3$ is hydrogen.
9. The compound of claim 1, wherein R$^4$ is halogen.
10. The compound of claim 9, wherein R$^4$ is F.
11. The compound of claim 1, wherein R$^4$ is halogen-C$_{1-6}$-alkoxy.
12. The compound of claim 11, wherein R$^4$ is —OCH$_2$CF$_3$.
13. The compound of claim 1, wherein R$^6$ is heteroaryl substituted by 1-2 substituents individually selected from cyano, halogen and C$_{3-6}$-cycloalkyl-C$_{2-6}$-alkynyl.
14. The compound of claim 1, wherein R$^2$ is pyridinyl substituted by 1-2 substituents individually selected from cyano, chloro and cyclopropylethynyl-.
15. The compound of claim 1, selected from the group consisting of
  5-Chloro-pyridine-2-carboxylic acid [3-((4R,5R)-2-amino-5-fluoro-4-methyl-5,6-dihydro-4H-[1,3]oxazin-4-yl)-4-fluoro-phenyl]-amide,
  5-Cyano-pyridine-2-carboxylic acid [3-((4R,5R)-2-amino-5-fluoro-4-methyl-5,6-dihydro-4H-[1,3]oxazin-4-yl)-4-fluoro-phenyl]-amide,
  5-Fluoromethoxy-pyridine-2-carboxylic acid [3-((4R,5R)-2-amino-5-fluoro-4-methyl-5,6-dihydro-4H-[1,3]oxazin-4-yl)-4-fluoro-phenyl]-amide,
  5-Difluoromethoxy-pyridine-2-carboxylic acid [3-((4R,5R)-2-amino-5-fluoro-4-methyl-5,6-dihydro-4H-[1,3]oxazin-4-yl)-4-fluoro-phenyl]-amide,
  3-Chloro-5-cyano-pyridine-2-carboxylic acid [3-((4R,5R)-2-amino-5-fluoro-4-methyl-5,6-dihydro-4H-[1,3]oxazin-4-yl)-4-fluoro-phenyl]-amide, 5-Chloro-3-fluoro-pyridine-2-carboxylic acid [3-((4R,5R)-2-amino-5-fluoro-4-methyl-5,6-dihydro-4H-[1,3]oxazin-4-yl)-4-fluoro-phenyl]-amide, 3-Chloro-5-trifluoromethyl-pyridine-2-carboxylic acid [3-((4R,5R)-2-amino-5-fluoro-4-methyl-5,6-dihydro-4H-[1,3]oxazin-4-yl)-4-fluoro-phenyl]-amide, 5-Fluoromethoxy-pyrazine-2-carboxylic acid [3-((4R,5R)-2-amino-5-fluoro-4-methyl-5,6-dihydro-4H-[1,3]oxazin-4-yl)-4-fluoro-phenyl]-amide, 5-Difluoromethyl-pyridine-2-carboxylic acid [3-((4R,5R)-2-amino-5-fluoro-4-methyl-5,6-dihydro-4H-[1,3]oxazin-4-yl)-4-fluoro-phenyl]-amide, 3-Fluoro-5-trifluoromethyl-pyridine-2-carboxylic acid [3-((4R,5R)-2-amino-5-fluoro-4-methyl-5,6-dihydro-4H-[1,3]oxazin-4-yl)-4-fluoro-phenyl]-amide, and 5-Methoxy-pyridine-2-carboxylic acid [3-((4R,5R)-2-amino-5-fluoro-4-methyl-5,6-dihydro-4H-[1,3]oxazin-4-yl)-4-fluoro-phenyl]-amide, or a pharmaceutical acceptable salt thereof.

16. The compound of claim 1, selected from the group consisting of

5-Cyclopropylethynyl-pyridine-2-carboxylic acid [3-((4R,5R)-2-amino-5-fluoro-4-methyl-5,6-dihydro-4H-[1,3]oxazin-4-yl)-4-fluoro-phenyl]-amide, 5-Difluoromethyl-pyrazine-2-carboxylic acid [3-((4R,5R)-2-amino-5-fluoro-4-methyl-5,6-dihydro-4H-[1,3]oxazin-4-yl)-4-fluoro-phenyl]-amide, 5-Cyclopropylmethoxy-pyrazine-2-carboxylic acid [3-((4R,5R)-2-amino-5-fluoro-4-methyl-5,6-dihydro-4H-[1,3]oxazin-4-yl)-4-fluoro-phenyl]-amide, 5-Fluoro-pyridine-2-carboxylic acid [3-((4R,5R)-2-amino-5-fluoro-4-methyl-5,6-dihydro-4H-[1,3]oxazin-4-yl)-4-fluoro-phenyl]-amide, 5-Cyclopropyl-pyridine-2-carboxylic acid [3-((4R,5R)-2-amino-5-fluoro-4-methyl-5,6-dihydro-4H-[1,3]oxazin-4-yl)-4-fluoro-phenyl]-amide, 5-Cyclopropylmethoxy-pyridine-2-carboxylic acid [3-((4R,5R)-2-amino-5-fluoro-4-methyl-5,6-dihydro-4H-[1,3]oxazin-4-yl)-4-fluoro-phenyl]-amide, 2-Chloro-thiazole-5-carboxylic acid [3-((4R,5R)-2-amino-5-fluoro-4-methyl-5,6-dihydro-4H-[1,3]oxazin-4-yl)-4-fluoro-phenyl]-amide, 2-Methyl-5-trifluoromethyl-2H-pyrazole-3-carboxylic acid [3-((4R,5R)-2-amino-5-fluoro-4-methyl-5,6-dihydro-4H-[1,3]oxazin-4-yl)-4-fluoro-phenyl]-amide, 4-Chloro-1H-pyrazole-3-carboxylic acid [3-((4R,5R)-2-amino-5-fluoro-4-methyl-5,6-dihydro-4H-[1,3]oxazin-4-yl)-4-fluoro-phenyl]-amide Thiazole-5-carboxylic acid [3-((4R,5R)-2-amino-5-fluoro-4-methyl-5,6-dihydro-4H-[1,3]oxazin-4-yl)-4-fluoro-phenyl]-amide, and Cyano-cyclopropanecarboxylic acid [3-((4R,5R)-2-amino-5-fluoro-4-methyl-5,6-dihydro-4H-[1,3]oxazin-4-yl)-4-fluoro-phenyl]-amide, or a pharmaceutical acceptable salt thereof.

17. The compound of claim 1, selected from the group consisting of

Cyclopropanecarboxylic acid [3-((4R,5R)-2-amino-5-fluoro-4-methyl-5,6-dihydro-4H-[1,3]oxazin-4-yl)-4-fluoro-phenyl]-amide, 5-Cyano-pyridine-2-carboxylic acid [3-((4R,5S)-2-amino-5-fluoro-4-methyl-5,6-dihydro-4H-[1,3]oxazin-4-yl)-4-fluoro-phenyl]-amide, 5-Chloro-pyridine-2-carboxylic acid [3-((4R,5S)-2-amino-5-fluoro-4-methyl-5,6-dihydro-4H-[1,3]oxazin-4-yl)-4-fluoro-phenyl]-amide, 3-Chloro-5-cyano-pyridine-2-carboxylic acid [3-((4R,5S)-2-amino-5-fluoro-4-methyl-5,6-dihydro-4H-[1,3]oxazin-4-yl)-4-fluoro-phenyl]-amide, 3-Chloro-5-trifluoromethyl-pyridine-2-carboxylic acid [3-((4R,5S)-2-amino-5-fluoro-4-methyl-5,6-dihydro-4H-[1,3]oxazin-4-yl)-4-fluoro-phenyl]-amide, 5-Cyano-pyridine-2-carboxylic acid [3-((4R,5R)-2-amino-5-fluoro-4,5-dimethyl-5,6-dihydro-4H-[1,3]oxazin-4-yl)-4-fluoro-phenyl]-amide, 4-Chloro-1-difluoromethyl-1H-pyrazole-3-carboxylic acid [3-((4R,5R)-2-amino-5-fluoro-4,5-dimethyl-5,6-dihydro-4H-[1,3]oxazin-4-yl)-4-fluoro-phenyl]-amide, 5-Chloro-pyridine-2-carboxylic acid [3-((4R,5R)-2-amino-5-fluoro-4,5-dimethyl-5,6-dihydro-4H-[1,3]oxazin-4-yl)-4-fluoro-phenyl]-amide 5-Fluoro-pyridine-2-carboxylic acid [3-((4R,5R)-2-amino-5-fluoro-4,5-dimethyl-5,6-dihydro-4H-[1,3]oxazin-4-yl)-4-fluoro-phenyl]-amide, 5-Chloro-pyridine-2-carboxylic acid {3-[(4R,5R)-2-amino-4-methyl-5-(2,2,2-trifluoro-ethoxy)-5,6-dihydro-4H-[1,3]oxazin-4-yl]-4-fluoro-phenyl}-amide, and 5-Fluoro-pyridine-2-carboxylic acid {3-[(4R,5R)-2-amino-4-methyl-5-(2,2,2-trifluoro-ethoxy)-5,6-dihydro-4H-[1,3]oxazin-4-yl]-4-fluoro-phenyl}-amide, or a pharmaceutical acceptable salt thereof.

18. The compound of claim 1, selected from the group consisting of

5-Cyano-pyridine-2-carboxylic acid {3-[(4R,5R)-2-amino-4-methyl-5-(2,2,2-trifluoro-ethoxy)-5,6-dihydro-4H-[1,3]oxazin-4-yl]-4-fluoro-phenyl}-amide, 5-But-2-ynyloxy-pyrazine-2-carboxylic acid [3-((4R,5R)-2-amino-5-fluoro-4,5-dimethyl-5,6-dihydro-4H-[1,3]oxazin-4-yl)-4-fluoro-phenyl]-amide, 5-Cyano-pyridine-2-carboxylic acid [3-((4S,5R)-2-amino-5-fluoro-4-fluoromethyl-5,6-dihydro-4H-[1,3]oxazin-4-yl)-4-fluoro-phenyl]-amide, 5-Cyano-pyridine-2-carboxylic acid [3-((4S,5S)-2-amino-5-fluoro-4-fluoromethyl-5,6-dihydro-4H-[1,3]oxazin-4-yl)-4-fluoro-phenyl]-amide, 5-Cyano-pyridine-2-carboxylic acid [3-((4R,5R)- or (4R,5S)-2-amino-4-difluoromethyl-5-fluoro-5,6-dihydro-4H-[1,3]oxazin-4-yl)-4-fluoro-phenyl]-amide, 5-(2,2,2-Trifluoro-ethoxy)-pyridine-2-carboxylic acid [3-((4R,5R)-2-amino-5-fluoro-4-methyl-5,6-dihydro-4H-[1,3]oxazin-4-yl)-4-fluoro-phenyl]-amide, 3-(2,2,2-Trifluoro-ethoxy)-pyridine-2-carboxylic acid [3-((4R,5R)-2-amino-5-fluoro-4,5-dimethyl-5,6-dihydro-4H-[1,3]oxazin-4-yl)-4-fluoro-phenyl]-amide 5-(2,2,2-Trifluoro-ethoxy)-pyridine-2-carboxylic acid {3-[(4R,5R)-2-amino-4-methyl-5-(2,2,2-trifluoro-ethoxy)-5,6-dihydro-4H-[1,3]oxazin-4-yl]-4-fluoro-phenyl}-amide, and 5-(2,2,3,3-Tetrafluoro-propoxy)-pyridine-2-carboxylic acid [3-((4R,5R)-2-amino-5-fluoro-4-methyl-5,6-dihydro-4H-[1,3]oxazin-4-yl)-4-fluoro-phenyl]-amide, or a pharmaceutical acceptable salt thereof.

19. The compound of claim 1, selected from the group consisting of 5-(2,2,3,3,3-Pentafluoro-propoxy)-pyridine-2-carboxylic acid [3-((4R,5R)-2-amino-5-fluoro-4-methyl-5,6-dihydro-4H-[1,3]oxazin-4-yl)-4-fluoro-phenyl]-amide, 1,5-Dimethyl-1H-pyrazole-3-carboxylic acid [3-((4R,5R)-2-amino-5-fluoro-4-methyl-5,6-dihydro-4H-[1,3]oxazin-4-yl)-4-fluoro-phenyl]-amide, 5-(2,2-Difluoro-ethoxy)-pyrazine-2-carboxylic acid [3-((4R,5R)-2-amino-5-fluoro-4-methyl-5,6-dihydro-4H-[1,3]oxazin-4-yl)-4-fluoro-phenyl]-amide, 5-(2,2-Difluoro-ethoxy)-pyridine-2-carboxylic acid [3-((4R,5R)-2-amino-5-fluoro-4-methyl-5,6-dihydro-4H-[1,3]oxazin-4-yl)-4-fluoro-phenyl]-amide, 4-Chloro-1-(2,2-difluoro-ethyl)-1H-pyrazole-3-carboxylic acid [3-((4R,5R)-2-amino-5-fluoro-4,5-dimethyl-5,6-dihydro-4H-[1,3]oxazin-4-yl)-4-fluoro-phenyl]-amide, 2,2-Difluoro-cyclopropanecarboxylic acid [3-((4R,5R)-2-amino-5-fluoro-4,5-dimethyl-5,6-dihydro-4H-[1,3]oxazin-4-yl)-4-fluoro-phenyl]-amide, 2,5-Dimethyl-furan-3-carboxylic acid [3-((4R,5R)-2-amino-5-fluoro-4-methyl-5,6-dihydro-4H-[1,3]oxazin-4-yl)-4-fluoro-phenyl]-amide, 3,5-Dichloro-pyridine-2-carboxylic acid [3-((4R,5R)-2-amino-5-fluoro-4-methyl-5,6-dihydro-4H-[1,3]oxazin-4-yl)-4-fluoro-phenyl]-amide, 3,5-Difluoro-pyridine-2-carboxylic acid [3-((4R,5R)-2-amino-5-fluoro-4-methyl-5,6-dihydro-4H-[1,3]oxazin-4-yl)-4-fluoro-phenyl]-amide, 3,5-Dichloro-pyridine-2-carboxylic acid [3-((4R,5R)-2-amino-5-fluoro-4,5-dimethyl-5,6-dihydro-4H-[1,3]oxazin-4-yl)-4-fluoro-phenyl]-amide, and 3,5-Dichloro-pyridine-2-carboxylic acid {3-[(4R,5R)-2-amino-4-methyl-5-(2,2,2-trifluoro-ethoxy)-5,6-dihydro-4H-[1,3]oxazin-4-yl]-4-fluoro-phenyl}-amide, or a pharmaceutical acceptable salt thereof.

20. The compound of claim 1, selected from the group consisting of

5-Chloro-pyridine-2-carboxylic acid [3-((4R,5R)-2-amino-5-fluoro-4-methyl-5,6-dihydro-4H-[1,3]oxazin-4-yl)-4-fluoro-phenyl]-amide, 1,5-Dimethyl-1H-pyrazole-3-carboxylic acid [3-((4R,5R)-2-amino-5-fluoro-4-methyl-5,6-dihydro-4H-[1,3]oxazin-4-yl)-4-fluoro-phenyl]-amide, Cyano-cyclopropanecarboxylic acid [3-((4R,5R)-2-amino-5-fluoro-4-methyl-5,6-dihydro-4H-[1,3]oxazin-4-yl)-4-fluoro-phenyl]-amide, 2,2-Difluoro-cyclopropanecarboxylic acid [3-((4R,5R)-2-amino-5-fluoro-4,5-dimethyl-5,6-dihydro-4H-[1,3]oxazin-4-yl)-4-fluoro-phenyl]-amide, 2,5-Dimethyl-furan-3-carboxylic acid [3-((4R,5R)-2-amino-5-fluoro-4-methyl-5,6-dihydro-4H-[1,3]oxazin-4-yl)-4-fluoro-phenyl]-amide, 2-Chloro-thiazole-5-carboxylic acid [3-((4R,5R)-2-amino-5-fluoro-4-methyl-5,6-dihydro-4H-[1,3]oxazin-4-yl)-4-fluoro-phenyl]-amide, 2-Methyl-5-trifluoromethyl-2H-pyrazole-3-carboxylic acid [3-((4R,5R)-2-amino-5-fluoro-4-methyl-5,6-dihydro-4H-[1,3]oxazin-4-yl)-4-fluoro-phenyl]-amide, 3-(2,2,2-Trifluoro-ethoxy)-pyridine-2-carboxylic acid [3-((4R,5R)-2-amino-5-fluoro-4,5-dimethyl-5,6-dihydro-4H-[1,3]oxazin-4-yl)-4-fluoro-phenyl]-amide, 3,5-Dichloro-pyridine-2-carboxylic acid [3-((4R,5R)-2-amino-5-fluoro-4-methyl-5,6-dihydro-4H-[1,3]oxazin-4-yl)-4-fluoro-phenyl]-amide, and 3,5-Dichloro-pyridine-2-carboxylic acid [3-((4R,5R)-2-amino-5-fluoro-4,5-dimethyl-5,6-dihydro-4H-[1,3]oxazin-4-yl)-4-fluoro-phenyl]-amide, or a pharmaceutical acceptable salt thereof.

21. The compound of claim 1, selected from the group consisting of 3,5-Dichloro-pyridine-2-carboxylic acid [3-((4R,5R)-2-amino-5-fluoro-4,5-dimethyl-5,6-dihydro-4H-[1,3]oxazin-4-yl)-4-fluoro-phenyl]-amide, 3,5-Dichloro-pyridine-2-carboxylic acid {3-[(4R,5R)-2-amino-4-methyl-5-(2,2,2-trifluoro-ethoxy)-5,6-dihydro-4H-[1,3]oxazin-4-yl]-4-fluoro-phenyl}-amide, 3,5-Difluoro-pyridine-2-carboxylic acid [3-((4R,5R)-2-amino-5-fluoro-4-methyl-5,6-dihydro-4H-[1,3]oxazin-4-yl)-4-fluoro-phenyl]-amide, 3-Chloro-5-cyano-pyridine-2-carboxylic acid [3-((4R,5R)-2-amino-5-fluoro-4-methyl-5,6-dihydro-4H-[1,3]oxazin-4-yl)-4-fluoro-phenyl]-amide, 3-Chloro-5-cyano-pyridine-2-carboxylic acid [3-((4R,5S)-2-amino-5-fluoro-4-methyl-5,6-dihydro-4H-[1,3]oxazin-4-yl)-4-fluoro-phenyl]-amide, 3-Chloro-5-trifluoromethyl-pyridine-2-carboxylic acid [3-((4R,5R)-2-amino-5-fluoro-4-methyl-5,6-dihydro-4H-[1,3]oxazin-4-yl)-4-fluoro-phenyl]-amide, 3-Chloro-5-trifluoromethyl-pyridine-2-carboxylic acid [3-((4R,5S)-2-amino-5-fluoro-4-methyl-5,6-dihydro-4H-[1,3]oxazin-4-yl)-4-fluoro-phenyl]-amide, 3-Fluoro-5-trifluoromethyl-pyridine-2-carboxylic acid [3-((4R,5R)-2-amino-5-fluoro-4-methyl-5,6-dihydro-4H-[1,3]oxazin-4-yl)-4-fluoro-phenyl]-amide, 4-Chloro-1-(2,2-difluoro-ethyl)-1H-pyrazole-3-carboxylic acid [3-((4R,5R)-2-amino-5-fluoro-4,5-dimethyl-5,6-dihydro-4H-[1,3]oxazin-4-yl)-4-fluoro-phenyl]-amide, and 4-Chloro-1H-pyrazole-3-carboxylic acid [3-((4R,5R)-2-amino-5-fluoro-4-methyl-5,6-dihydro-4H-[1,3]oxazin-4-yl)-4-fluoro-phenyl]-amide, or a pharmaceutically acceptable salt thereof.

22. The compound of claim 1, selected from the group consisting of 5-(2,2,2-Trifluoro-ethoxy)-pyridine-2-carboxylic acid [3-((4R,5R)-2-amino-5-fluoro-4-methyl-5,6-dihydro-4H-[1,3]oxazin-4-yl)-4-fluoro-phenyl]-amide, 5-(2,2,2-Trifluoro-ethoxy)-pyridine-2-carboxylic acid {3-[(4R,5R)-2-amino-4-methyl-5-(2,2,2-trifluoro-ethoxy)-5,6-dihydro-4H-[1,3]oxazin-4-yl]-4-fluoro-phenyl}-amide, 5-(2,2,3,3,3-Pentafluoro-propoxy)-pyridine-2-carboxylic acid [3-((4R,5R)-2-amino-5-fluoro-4-methyl-5,6-dihydro-4H-[1,3]oxazin-4-yl)-4-fluoro-phenyl]-amide, 5-(2,2,3,3-Tetrafluoro-propoxy)-pyridine-2-carboxylic acid [3-((4R,5R)-2-amino-5-fluoro-4-methyl-5,6-dihydro-4H-[1,3]oxazin-4-yl)-4-fluoro-phenyl]-amide, 5-(2,2-Difluoro-ethoxy)-pyrazine-2-carboxylic acid [3-((4R,5R)-2-amino-5-fluoro-4-methyl-5,6-dihydro-4H-[1,3]oxazin-4-yl)-4-fluoro-phenyl]-amide, 5-(2,2-Difluoro-ethoxy)-pyridine-2-carboxylic acid [3-((4R,5R)-2-amino-5-fluoro-4-methyl-5,6-dihydro-4H-[1,3]oxazin-4-yl)-4-fluoro-phenyl]-amide, 5-Chloro-3-fluoro-pyridine-2-carboxylic acid [3-((4R,5R)-2-amino-5-fluoro-4-methyl-5,6-dihydro-4H-[1,3]oxazin-4-yl)-4-fluoro-phenyl]-amide, 5-Chloro-pyridine-2-carboxylic acid [3-((4R,5R)-2-amino-5-fluoro-4,5-dimethyl-5,6-dihydro-4H-[1,3]oxazin-4-yl)-4-fluoro-phenyl]-amide, 5-Chloro-pyridine-2-carboxylic acid [3-((4R,5S)-2-amino-5-fluoro-4-methyl-5,6-dihydro-4H-[1,3]oxazin-4-yl)-4-fluoro-phenyl]-amide, and 5-Chloro-pyridine-2-carboxylic acid {3-[(4R,5R)-2-amino-4-methyl-5-(2,2,2-trifluoro-ethoxy)-5,6-dihydro-4H-[1,3]oxazin-4-yl]-4-fluoro-phenyl}-amide, or a pharmaceutical acceptable salt thereof.

23. The compound of claim 1, selected from the group consisting of

5-Cyano-pyridine-2-carboxylic acid [3-((4R,5R)-2-amino-5-fluoro-4-methyl-5,6-dihydro-4H-[1,3]oxazin-4-yl)-4-fluoro-phenyl]-amide, 5-Cyano-pyridine-2-carboxylic acid [3-((4R,5R)-2-amino-5-fluoro-4,5-dimethyl-5,6-dihydro-4H-[1,3]oxazin-4-yl)-4-fluoro-phenyl]-amide,
5-Cyano-pyridine-2-carboxylic acid [3-((4R,5S)-2-amino-5-fluoro-4-methyl-5,6-dihydro-4H-[1,3]oxazin-4-yl)-4-fluoro-phenyl]-amide,
5-Cyano-pyridine-2-carboxylic acid {3-[(4R,5R)-2-amino-4-methyl-5-(2,2,2-trifluoro-ethoxy)-5,6-dihydro-4H-[1,3]oxazin-4-yl]-4-fluoro-phenyl}-amide,
5-Cyclopropylethynyl-pyridine-2-carboxylic acid [3-((4R,5R)-2-amino-5-fluoro-4-methyl-5,6-dihydro-4H-[1,3]oxazin-4-yl)-4-fluoro-phenyl]-amide,
5-Cyclopropylmethoxy-pyrazine-2-carboxylic acid [3-((4R,5R)-2-amino-5-fluoro-4-methyl-5,6-dihydro-4H-[1,3]oxazin-4-yl)-4-fluoro-phenyl]-amide,
5-Cyclopropylmethoxy-pyridine-2-carboxylic acid [3-((4R,5R)-2-amino-5-fluoro-4-methyl-5,6-dihydro-4H-[1,3]oxazin-4-yl)-4-fluoro-phenyl]-amide,
5-Cyclopropyl-pyridine-2-carboxylic acid [3-((4R,5R)-2-amino-5-fluoro-4-methyl-5,6-dihydro-4H-[1,3]oxazin-4-yl)-4-fluoro-phenyl]-amide,
5-Difluoromethoxy-pyridine-2-carboxylic acid [3-((4R,5R)-2-amino-5-fluoro-4-methyl-5,6-dihydro-4H-[1,3]oxazin-4-yl)-4-fluoro-phenyl]-amide, and
5-Difluoromethyl-pyrazine-2-carboxylic acid [3-((4R,5R)-2-amino-5-fluoro-4-methyl-5,6-dihydro-4H-[1,3]oxazin-4-yl)-4-fluoro-phenyl]-amide,
or a pharmaceutically acceptable salt thereof.

24. The compound of claim 1, selected from the group consisting of
5-Difluoromethyl-pyridine-2-carboxylic acid [3-((4R,5R)-2-amino-5-fluoro-4-methyl-5,6-dihydro-4H-[1,3]oxazin-4-yl)-4-fluoro-phenyl]-amide,
5-Fluoromethoxy-pyrazine-2-carboxylic acid [3-((4R,5R)-2-amino-5-fluoro-4-methyl-5,6-dihydro-4H-[1,3]oxazin-4-yl)-4-fluoro-phenyl]-amide,
5-Fluoromethoxy-pyridine-2-carboxylic acid [3-((4R,5R)-2-amino-5-fluoro-4-methyl-5,6-dihydro-4H-[1,3]oxazin-4-yl)-4-fluoro-phenyl]-amide,
5-Fluoro-pyridine-2-carboxylic acid [3-((4R,5R)-2-amino-5-fluoro-4-methyl-5,6-dihydro-4H-[1,3]oxazin-4-yl)-4-fluoro-phenyl]-amide,
5-Fluoro-pyridine-2-carboxylic acid [3-((4R,5R)-2-amino-5-fluoro-4,5-dimethyl-5,6-dihydro-4H-[1,3]oxazin-4-yl)-4-fluoro-phenyl]-amide,
5-Fluoro-pyridine-2-carboxylic acid {3-[(4R,5R)-2-amino-4-methyl-5-(2,2,2-trifluoro-ethoxy)-5,6-dihydro-4H-[1,3]oxazin-4-yl]-4-fluoro-phenyl}-amide,
5-Methoxy-pyridine-2-carboxylic acid [3-((4R,5R)-2-amino-5-fluoro-4-methyl-5,6-dihydro-4H-[1,3]oxazin-4-yl)-4-fluoro-phenyl]-amide,
Cyclopropanecarboxylic acid [3-((4R,5R)-2-amino-5-fluoro-4-methyl-5,6-dihydro-4H-[1,3]oxazin-4-yl)-4-fluoro-phenyl]-amide, and
Thiazole-5-carboxylic acid [3-((4R,5R)-2-amino-5-fluoro-4-methyl-5,6-dihydro-4H-[1,3]oxazin-4-yl)-4-fluoro-phenyl]-amide,
or a pharmaceutical acceptable salt thereof.

25. The compound of claim 1, selected from the group consisting of
5-Chloro-pyridine-2-carboxylic acid [3-((4R,5R)-2-amino-5-fluoro-4-methyl-5,6-dihydro-4H-[1,3]oxazin-4-yl)-4-fluoro-phenyl]-amide,
3,5-Dichloro-pyridine-2-carboxylic acid [3-((4R,5R)-2-amino-5-fluoro-4-methyl-5,6-dihydro-4H-[1,3]oxazin-4-yl)-4-fluoro-phenyl]-amide, 5-Cyano-pyridine-2-carboxylic acid [3-((4R,5R)-2-amino-5-fluoro-4-methyl-5,6-dihydro-4H-[1,3]oxazin-4-yl)-4-fluoro-phenyl]-amide,
5-Cyano-pyridine-2-carboxylic acid {3-[(4R,5R)-2-amino-4-methyl-5-(2,2,2-trifluoro-ethoxy)-5,6-dihydro-4H-[1,3]oxazin-4-yl]-4-fluoro-phenyl}-amide,
5-Cyclopropylethynyl-pyridine-2-carboxylic acid [3-((4R,5R)-2-amino-5-fluoro-4-methyl-5,6-dihydro-4H-[1,3]oxazin-4-yl)-4-fluoro-phenyl]-amide, and
5-But-2-ynyloxy-pyrazine-2-carboxylic acid [3-((4R,5R)-2-amino-5-fluoro-4,5-dimethyl-5,6-dihydro-4H-[1,3]oxazin-4-yl)-4-fluoro-phenyl]-amide,
or a pharmaceutical acceptable salt thereof.

26. A pharmaceutical composition comprising a therapeutically effective amount of a compound of formula I

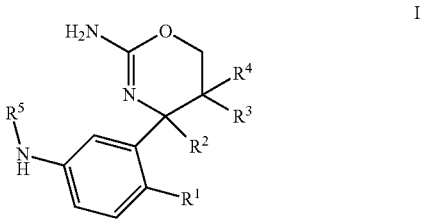

wherein
$R^1$ is selected from the group consisting of
hydrogen,
halogen, and
$C_{1-6}$-alkyl;
$R^2$ is selected from the group consisting of
hydrogen,
$C_{1-6}$-alkyl, and
halogen-$C_{1-3}$-alkyl;
$R^3$ is selected from the group consisting of
hydrogen and
$C_{1-6}$-alkyl;
$R^4$ is selected from the group consisting of
halogen,
$C_{1-6}$-alkyl, and
halogen-$C_{1-6}$-alkoxy;
$R^5$ is —C(=O)—$R^6$; and
$R^6$ is selected from the group consisting of
heteroaryl,
heteroaryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{3-6}$-cycloalkyl, $C_{3-6}$-cycloalkyl-$C_{1-6}$-alkoxy, $C_{3-6}$-cycloalkyl-$C_{1-6}$-alkyl, $C_{3-6}$-cycloalkyl-$C_{2-6}$-alkynyl, $C_{2-6}$-alkynyl-$C_{1-6}$-alkoxy and $C_{1-6}$-alkyl,
$C_{3-6}$-cycloalkyl,
$C_{3-6}$-cycloalkyl substituted by 1-4 substituents individually selected from cyano, cyano-$C_{1-6}$-alkyl, halogen, halogen-$C_{1-6}$-alkoxy, halogen-$C_{1-6}$-alkyl, hydroxy, $C_{1-6}$-alkoxy, $C_{1-6}$-alkoxy-$C_{1-6}$-alkyl and $C_{1-6}$-alkyl,
heterocyclyl, and
heterocyclyl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl and $C_{1-6}$-alkyl;
or a pharmaceutically acceptable salt thereof
and a pharmaceutically acceptable carrier.

* * * * *

UNITED STATES PATENT AND TRADEMARK OFFICE
CERTIFICATE OF CORRECTION

PATENT NO. : 9,115,098 B2  
APPLICATION NO. : 14/268085  
DATED : August 25, 2015  
INVENTOR(S) : Hans Hilpert et al.

Page 1 of 1

It is certified that error appears in the above-identified patent and that said Letters Patent is hereby corrected as shown below:

On the Title page, item (73) Assignees to read as follows:

-- HOFFMANN-LA ROCHE INC., Nutley, NJ (US) --

Signed and Sealed this  
Nineteenth Day of January, 2016

Michelle K. Lee  
*Director of the United States Patent and Trademark Office*